(12) United States Patent
Mamluk et al.

(10) Patent No.: US 9,566,246 B2
(45) Date of Patent: *Feb. 14, 2017

(54) PHARMACEUTICAL COMPOSITIONS AND RELATED METHODS OF DELIVERY

(71) Applicant: CHIASMA INC., Newton, MA (US)

(72) Inventors: Roni Mamluk, Mazkeret Batya (IL); Moshe Tzabari, Jerusalem (IL); Karen Marom, Mevaseret Zion (IL); Paul Salama, Ashdod (IL); Irina Weinstein, Maale Adummim (IL)

(73) Assignee: CHIASMA INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/044,949

(22) Filed: Feb. 16, 2016

(65) Prior Publication Data

US 2016/0158159 A1 Jun. 9, 2016

Related U.S. Application Data

(63) Continuation of application No. 14/188,139, filed on Feb. 24, 2014, now Pat. No. 9,265,812, which is a continuation of application No. 12/981,036, filed on Dec. 29, 2010, now abandoned, which is a continuation of application No. 12/561,738, filed on Sep. 17, 2009, now abandoned.

(60) Provisional application No. 61/161,387, filed on Mar. 18, 2009, provisional application No. 61/141,686, filed on Dec. 31, 2008, provisional application No. 61/097,716, filed on Sep. 17, 2008.

(51) Int. Cl.
| | |
|---|---|
| A61K 9/00 | (2006.01) |
| A61K 9/48 | (2006.01) |
| A61K 9/10 | (2006.01) |
| A61K 31/70 | (2006.01) |
| A61K 38/21 | (2006.01) |
| A61K 38/27 | (2006.01) |
| A61K 38/28 | (2006.01) |
| A61K 38/29 | (2006.01) |
| A61K 47/14 | (2006.01) |
| A61K 47/44 | (2006.01) |
| A61K 38/12 | (2006.01) |
| A61K 47/12 | (2006.01) |
| A61K 47/32 | (2006.01) |
| A61K 38/09 | (2006.01) |
| A61K 38/11 | (2006.01) |
| A61K 38/14 | (2006.01) |
| A61K 38/22 | (2006.01) |
| A61K 38/26 | (2006.01) |
| A61K 51/10 | (2006.01) |
| A61K 51/08 | (2006.01) |
| A61K 9/16 | (2006.01) |

(52) U.S. Cl.
CPC .......... *A61K 9/4891* (2013.01); *A61K 9/0031* (2013.01); *A61K 9/0053* (2013.01); *A61K 9/10* (2013.01); *A61K 9/4858* (2013.01); *A61K 9/4866* (2013.01); *A61K 31/70* (2013.01); *A61K 38/09* (2013.01); *A61K 38/11* (2013.01); *A61K 38/12* (2013.01); *A61K 38/14* (2013.01); *A61K 38/212* (2013.01); *A61K 38/22* (2013.01); *A61K 38/26* (2013.01); *A61K 38/27* (2013.01); *A61K 38/28* (2013.01); *A61K 38/29* (2013.01); *A61K 47/12* (2013.01); *A61K 47/14* (2013.01); *A61K 47/32* (2013.01); *A61K 47/44* (2013.01); *A61K 9/1623* (2013.01); *A61K 51/083* (2013.01); *A61K 51/1021* (2013.01); *A61K 51/1024* (2013.01); *A61K 51/1045* (2013.01)

(58) Field of Classification Search
None
See application file for complete search history.

(56) References Cited

U.S. PATENT DOCUMENTS

| | | | |
|---|---|---|---|
| 3,869,549 | A | 3/1975 | Geller |
| 4,156,719 | A | 5/1979 | Sezaki et al. |
| 4,234,437 | A | 11/1980 | Friberg et al. |
| 4,338,306 | A | 7/1982 | Kitao et al. |
| 4,485,033 | A | 11/1984 | Kitao et al. |
| 4,489,097 | A | 12/1984 | Stone |
| 4,508,828 | A | 4/1985 | Lindall et al. |
| 4,572,915 | A | 2/1986 | Crooks |
| 4,650,665 | A | 3/1987 | Kronenthal et al. |

(Continued)

FOREIGN PATENT DOCUMENTS

| | | |
|---|---|---|
| CA | 2003340 A1 | 5/1990 |
| CA | 2069760 A1 | 3/1992 |

(Continued)

OTHER PUBLICATIONS

Armstrong, Physiology of the Gastrointestinal Tract, 2nd Ed., Johnson, ed., Raven Press, New York, Chapter 45,2:1251-1265 (1987).

(Continued)

*Primary Examiner* — James Rogers
(74) *Attorney, Agent, or Firm* — Lando & Anastasi, LLP

(57) ABSTRACT

The pharmaceutical compositions described herein include a suspension which comprises an admixture in solid form of a therapeutically effective amount of a therapeutic agent and at least one salt of a medium chain fatty acid and a hydrophobic medium, e.g. castor oil or glyceryl tricaprylate or a mixture thereof. The pharmaceutical compositions described herein contain medium chain fatty acid salts and are substantially free of alcohols. The pharmaceutical compositions may be encapsulated in a capsule. Methods of treating or preventing diseases by administering such compositions to affected subjects are also disclosed.

30 Claims, 10 Drawing Sheets

(56) References Cited

U.S. PATENT DOCUMENTS

| | | |
|---|---|---|
| 4,871,777 A | 10/1989 | Breitzke |
| 4,895,726 A | 1/1990 | Curtet et al. |
| 4,985,404 A | 1/1991 | Mitchell |
| 5,200,192 A | 4/1993 | Wimmer |
| 5,206,219 A | 4/1993 | Desai |
| 5,246,716 A | 9/1993 | Sedun et al. |
| 5,254,331 A | 10/1993 | Mausner |
| 5,288,492 A | 2/1994 | Morris |
| 5,318,781 A | 6/1994 | Shah et al. |
| 5,393,738 A | 2/1995 | Vonderscher et al. |
| 5,443,842 A | 8/1995 | Seghizzi et al. |
| 5,462,726 A | 10/1995 | Lodge |
| 5,491,171 A | 2/1996 | Nishimura et al. |
| 5,506,203 A | 4/1996 | Backstrom et al. |
| 5,561,115 A | 10/1996 | Tenold |
| 5,656,289 A | 8/1997 | Cho et al. |
| 5,658,878 A | 8/1997 | Backstrom et al. |
| 5,665,384 A | 9/1997 | Courteille et al. |
| 5,665,711 A | 9/1997 | Sakai et al. |
| 5,686,488 A | 11/1997 | Gamache et al. |
| 5,714,477 A | 2/1998 | Einarsson |
| 5,726,154 A | 3/1998 | Baudys et al. |
| 5,738,871 A | 4/1998 | Story |
| 5,760,096 A | 6/1998 | Thornfeldt et al. |
| 5,804,573 A | 9/1998 | Silver |
| 5,827,534 A | 10/1998 | Fasano |
| 5,840,685 A | 11/1998 | Fujii et al. |
| 5,853,748 A | 12/1998 | New |
| 5,858,401 A | 1/1999 | Bhalani et al. |
| 5,859,048 A | 1/1999 | Oohashi et al. |
| 5,929,030 A | 7/1999 | Hamied et al. |
| 5,942,237 A | 8/1999 | Gizurarson et al. |
| 6,013,657 A | 1/2000 | Lavon et al. |
| 6,096,338 A | 8/2000 | Lacy et al. |
| 6,114,319 A | 9/2000 | Kimura et al. |
| 6,120,801 A | 9/2000 | Parekh et al. |
| 6,136,336 A | 10/2000 | Tanaka et al. |
| 6,190,702 B1 | 2/2001 | Takada et al. |
| 6,193,986 B1 | 2/2001 | Sakurada |
| 6,200,602 B1 | 3/2001 | Watts et al. |
| 6,214,380 B1 | 4/2001 | Parekh et al. |
| 6,255,502 B1 | 7/2001 | Penkler et al. |
| 6,284,223 B1 | 9/2001 | Luiken |
| 6,322,550 B2 | 11/2001 | Iga et al. |
| 6,326,026 B1 | 12/2001 | Parekh et al. |
| 6,326,360 B1 | 12/2001 | Kanazawa et al. |
| 6,333,046 B1 | 12/2001 | Sakai et al. |
| 6,365,596 B1 | 4/2002 | Valenti |
| 6,368,622 B2 | 4/2002 | Chen et al. |
| 6,383,527 B1 | 5/2002 | Artman et al. |
| 6,419,949 B1 | 7/2002 | Gasco |
| 6,428,813 B1 | 8/2002 | Akiyama et al. |
| 6,632,443 B2 | 10/2003 | Borowy-Borowski et al. |
| 6,664,234 B1 | 12/2003 | Heintz et al. |
| 6,696,413 B2 | 2/2004 | Fischer et al. |
| 6,710,195 B2 | 3/2004 | Joshi-Hangal et al. |
| 6,720,002 B2 | 4/2004 | Lin et al. |
| 6,770,292 B2 | 8/2004 | Guinez et al. |
| 6,835,396 B2 | 12/2004 | Brynjelsen et al. |
| 6,890,961 B2 | 5/2005 | Li et al. |
| 7,141,547 B2 | 11/2006 | Rosen et al. |
| 7,217,431 B2 | 5/2007 | Holm et al. |
| 7,288,520 B2 | 10/2007 | Chang et al. |
| 7,411,039 B2 | 8/2008 | Thim et al. |
| 7,759,312 B2 | 7/2010 | Kuzma et al. |
| 8,241,670 B2 | 8/2012 | Ben-Sasson |
| 8,329,198 B2 | 12/2012 | Salama et al. |
| 8,535,695 B2 | 9/2013 | Salama et al. |
| 2001/0055569 A1 | 12/2001 | Davis et al. |
| 2002/0091623 A1 | 7/2002 | Daniels |
| 2002/0151495 A1 | 10/2002 | Wolfe et al. |
| 2002/0188148 A1 | 12/2002 | O'Lenick et al. |
| 2003/0091623 A1 | 5/2003 | Cumming et al. |
| 2003/0095928 A1 | 5/2003 | McGurk et al. |
| 2003/0108610 A1 | 6/2003 | Flore et al. |
| 2003/0125528 A1 | 7/2003 | Hay et al. |
| 2003/0153614 A1 | 8/2003 | Joshi-Hangal et al. |
| 2003/0162695 A1 | 8/2003 | Schatzberg et al. |
| 2003/0166508 A1 | 9/2003 | Zhang |
| 2003/0176379 A1 | 9/2003 | Raoof et al. |
| 2004/0009231 A1 | 1/2004 | Jackson et al. |
| 2004/0147599 A1 | 7/2004 | Gagnon et al. |
| 2004/0167205 A1 | 8/2004 | Joshi-Hangal et al. |
| 2004/0248901 A1 | 12/2004 | Lee et al. |
| 2005/0004002 A1 | 1/2005 | Desai et al. |
| 2005/0112191 A1 | 5/2005 | Lipari et al. |
| 2005/0142225 A1 | 6/2005 | Kysilka et al. |
| 2005/0186277 A1 | 8/2005 | Gale et al. |
| 2005/0209441 A1 | 9/2005 | Lile |
| 2005/0232981 A1 | 10/2005 | Ben-Sasson |
| 2005/0256097 A1 | 11/2005 | Zhong et al. |
| 2005/0287203 A1 | 12/2005 | Nijs De et al. |
| 2006/0002989 A1 | 1/2006 | Ahmed et al. |
| 2006/0014712 A1 | 1/2006 | Neuman |
| 2006/0052404 A1 | 3/2006 | Rudolph et al. |
| 2006/0057185 A1 | 3/2006 | Akimoto et al. |
| 2006/0069055 A1 | 3/2006 | Dajee et al. |
| 2006/0078618 A1 | 4/2006 | Constantinides et al. |
| 2006/0128800 A1 | 6/2006 | Penney et al. |
| 2006/0165809 A1 | 7/2006 | Guimberteau et al. |
| 2006/0188566 A1 | 8/2006 | Liversidge et al. |
| 2006/0189662 A1 | 8/2006 | Goto et al. |
| 2006/0275253 A1 | 12/2006 | Ushida et al. |
| 2007/0004668 A1 | 1/2007 | Raoof et al. |
| 2007/0015694 A1 | 1/2007 | Chang et al. |
| 2007/0021325 A1 | 1/2007 | Byun et al. |
| 2007/0104741 A1 | 5/2007 | Murty et al. |
| 2007/0134319 A1 | 6/2007 | Zannou et al. |
| 2007/0148228 A1 | 6/2007 | Cumming et al. |
| 2007/0185194 A1 | 8/2007 | Mehta et al. |
| 2007/0190139 A1 | 8/2007 | Zerbe et al. |
| 2007/0196464 A1 | 8/2007 | Cumming et al. |
| 2007/0207214 A1 | 9/2007 | Castan et al. |
| 2007/0219131 A1 | 9/2007 | Ben-Sasson |
| 2007/0224142 A1 | 9/2007 | Swaile et al. |
| 2007/0237832 A1 | 10/2007 | Sackler et al. |
| 2007/0237833 A1 | 10/2007 | Sackler et al. |
| 2007/0238707 A1 | 10/2007 | Leonard |
| 2007/0248549 A1 | 10/2007 | Kuhrts |
| 2007/0248668 A1 | 10/2007 | Michaelis et al. |
| 2007/0254954 A1 | 11/2007 | Sakakibara et al. |
| 2007/0259098 A1 | 11/2007 | Gulian et al. |
| 2007/0292512 A1 | 12/2007 | Leonard et al. |
| 2008/0275001 A1 | 11/2008 | Cumming et al. |
| 2009/0280169 A1 | 11/2009 | Leonard |
| 2010/0028421 A1 | 2/2010 | Cumming et al. |
| 2010/0105627 A1 | 4/2010 | Salama et al. |
| 2010/0285143 A1 | 11/2010 | Khedkar et al. |
| 2011/0257095 A1 | 10/2011 | Salama et al. |
| 2015/0031631 A1 | 1/2015 | Mamluk et al. |

FOREIGN PATENT DOCUMENTS

| | | | |
|---|---|---|---|
| CA | 2363123 | A1 | 8/2000 |
| CA | 2563533 | A1 | 9/2006 |
| CN | 1960746 | A | 5/2007 |
| CN | 101084016 | A | 12/2007 |
| EP | 0366277 | A2 | 5/1990 |
| EP | 370481 | A2 | 5/1990 |
| EP | 0480189 | A1 | 4/1992 |
| EP | 000554767 | A1 | 8/1993 |
| EP | 1154761 | A1 | 11/2001 |
| EP | 1424077 | A1 | 6/2004 |
| EP | 2343982 | A2 | 7/2011 |
| IE | 63119 | B1 | 3/1995 |
| JP | 2007528388 | A | 10/2007 |
| JP | 2010-510206 | A | 4/2010 |
| JP | 2011503160 | A | 1/2011 |
| JP | 2011113487 | A | 6/2011 |
| WO | 96/31213 | A1 | 10/1996 |
| WO | 9705903 | A2 | 2/1997 |
| WO | 00/47203 | A1 | 8/2000 |
| WO | 0101960 | A1 | 1/2001 |
| WO | 03/004001 | A1 | 1/2003 |

(56) References Cited

FOREIGN PATENT DOCUMENTS

| WO | 03013589 | A1 | 2/2003 |
|---|---|---|---|
| WO | 03/037345 | A1 | 5/2003 |
| WO | 03/060071 | A2 | 7/2003 |
| WO | 2005000012 | A1 | 1/2005 |
| WO | 2005/087194 | A1 | 9/2005 |
| WO | 2005094785 | A2 | 10/2005 |
| WO | 2005/115333 | A2 | 12/2005 |
| WO | 2006097793 | A2 | 9/2006 |
| WO | 2006123360 | A2 | 11/2006 |
| WO | 2007071395 | A1 | 6/2007 |
| WO | 2008/066279 | A1 | 6/2008 |
| WO | 2010032140 | A2 | 3/2010 |

OTHER PUBLICATIONS

Aungst et al., "Enhancement of intestinal absorption of peptides and non-peptides" J. of Controlled Release, vol. 41, pp. 19-31, 1996.
Bernkop-Schniirch, "The use of inhibitory agents to overcome the enzymatic barrier to perorally administered therapeutic peptides and proteins." J., Control. Release, 52:1-16 (1998).
Citi, "Protein kinase inhibitors prevent junction dissociation induced by low extracellular calcium in MDCK epithelial cells." J. Cell Bioi., 117(1):169-178 (1992).
Constantinides, et. al., "Formulation and intestinal absorption enhancement evaluation of water-in-oil microemulsions incorporating medium-chain glycerides." Pharm. Res., 11(10):1385-1390 (1994).
Delie, "Evaluation of nano- and microparticle uptake by the gastrointestinal tract." Adv. Drug Del. Rev., 34(1):221-233 (1998).
European Office Action dated Dec. 16, 2011 for application No. 05 857 653.9-1219.
Fasano, et. al., "Fasano, et. al., Proc. Nat. Acad. Sci. USA, 88:5242-5246" Proc. Nat. Acad. Sci. USA, 88:5242-5246 (1991).
Filikov, et. al., "Structure-based design of ligands for protein basic domains: application to the HIV-1 Tat protein." J. Comput. Aided Mol. Des., 12(3):229-240 (1998).
Fiorentini, et. al., "Clostridium difficile toxin A and its effects on cells." Toxicon, 29(6):543-567 (1991).
Fox, "Developments in parathyroid hormone and related peptides as bone-formation agents." Curr. Opin. Pharmacol., 2:338-344 (2002).
Gumbiner, "Structure, biochemistry, and assembly of epithelial tight junctions." Am. J. Physiol., 253:C749-C758 (1987).
Hecht, et. al., "Clostridium difficile toxin A perturbs cytoskeletal structure and tight junction permeability of cultured human intestinal epithelial monolayers." J. Clin. Invest., 82:1516-1524 (1988).
Hsi-U I Ho et al., "Preperation of microemulsions using polyglcerol fatty acid esthers as surfactant for the delivery of protein drugs". Journal of Pharmaceutcal Sciences, American Pharmaceutical Association, Washington, US, vol. 85, No. 2, pp. 138-143, Feb. 1, 1996.
Hsiu-I Ho et al. "Preparation of Microemulsions Using Polyglycerol Fatty Acid Esters as Surfactant for the Delivery of Protein Drugs". Journal of Pharmaceutical Sciences, American Pharmaceutical Association. Washington, US, vol. 85 No. 2, Feb. 1, 1996, pp. 138-143.

International Preliminary Report on Patentability from International Application Serial No. PCT/IB07/04569 mailed Oct. 20, 2009.
International Search Report dated Mar. 18, 2010 in related WO application—PCT/IB 09/07155.
International Search Report from corresponding international patent application No. PCT/IB07/04569, dated Oct. 20, 2009.
International Search Report from corresponding international patent application No. PCT/IB2005/004183, dated Oct. 19, 2006.
Jackson, "Drug Transport Across Gastrointestinal Epithelia", Physiology of the Gastrointestinal Tract, 2nd Ed., Johnson, ed., Raven Press, New York, Chapter 59,2:1597-1621 (1987).
Jiao, et. al., "In vitro and in vivo evaluation of oral heparin-loaded polymeric nanoparticles in rabbits." Circulation, 105:230-235 (2002).
Kohler, et. al., "Absorption of an Aqueous Solution of a New Synthetic Somatostian Analogue Administered to Man by Gavage" Eur. J. Clin Pharamacol, (1987) 33: 167-171.
Madara, "In vitro and in vivo evaluation of oral heparin-loaded polymeric nanoparticles in rabbits." J. Clin. Invest., 83:1089-1094 (1989).
Nir et al, "Fear of injections in young adults; prevalence and associations", Am. J. Trop. Med. Hyg., 68(3), pp. 341-344, 2003.
Ouyang, et. al., "Structure-activity relationship for enhancement of paracellular permeability across Caco-2 cell monolayers by 3-alkylamido-2-alkoxypropylphosphocholines." J. Med. Chem., 45(13):2857-2866 (2002).
Prescribing information for Sandostatin LAR.
Rebouche, "Carnitine absorption: effects of sodium valproate and sodium actanoate in the caco-2 cell culture model of human intenstinal epithelium", L. Nutr. Biochem., vol. 9, pp. 228-235, Apr. 1998.
Schilfgaarde, et. al., "Cloning of genes of nontypeable Haemophilus influenzae involved in penetration between human lung epithelial cells." Infect. Immun., 68(8):4616-4623 (2000).
Search Report for CN 200980140593.9 dated Mar. 12, 2013.
Wang, et. al., "Increasing epithelial junction permeability enhances gene transfer to airway epithelia in vivo." Am. J. Respir. Cell Mol. Biol., 22:129-138 (2000).
Watnasirichaikul S. et al, "Preperation of biodegradable insulin nanocapsules from biocompatible microemulsions", PharmaceuticalResearch, vol. 17, No. 6, p. 684-689, 2000.
Watnasirichaikul, et. al., "In-vitro release and oral bioactivity of insulin in diabetic rats using nanocapsules dispersed in biocompatible microemulsion." J. Pharm. Pharmacal., 54(4):473-480 (2002).
Wright et al., "Fear of needles—nature and prevalence in general practice", Australian family physician, 38(3), Mar. 2003.
Written Opinion in related WO application—PCT/IB 09/07155, dated Mar. 18, 2010.
Written Opinion of the International Searching Authority for corresponding international patent application PCT/IB2005/004183, dated Oct. 19, 2006.
Yowell, et. al., "Novel Effects with Polyethylene glycol modified pharmaceuticals", Cancer Treat. Rev., 28(Suppl. A):3-6 (2002).
Zavoico, et. al., "Perturbation of egg phosphatidylcholine and dipalmitoylphosphatidylcholine multilamellar vesicles by n-alkanols. A fluorescent probe study." Biochimica et Biophysica Acta, 812(2)299-312 (1985).

PHARMACEUTICAL COMPOSITIONS AND RELATED METHODS OF DELIVERY

CLAIM OF PRIORITY

The present application is a continuation of U.S. application Ser. No. 14/188,139, filed Feb. 24, 2014, which is a continuation of U.S. application Ser. No. 12/981,036, filed Dec. 29, 2010, which is a continuation of U.S. application Ser. No. 12/561,738, filed Sep. 17, 2009 which claims priority from U.S. Ser. No. 61/097,716, filed Sep. 17, 2008, U.S. Ser. No. 61/141,686, filed Dec. 31, 2008, and U.S. Ser. No. 61/161,387, filed Mar. 18, 2009, each of which is incorporated by reference in its entirety.

FIELD OF THE TECHNOLOGY

The present invention relates generally to pharmaceutical compositions enabling improved delivery e.g. oral delivery and methods of using such compositions.

BACKGROUND

Techniques enabling efficient transfer of a substance of interest across a biological barrier are of considerable interest in the fields of biotechnology and medicine. For example, such techniques may be used for the transport of a variety of different substances across a biological barrier regulated by tight junctions (i.e., the mucosal epithelia, which include the intestinal and respiratory epithelia, and the vascular endothelia, which include the blood-brain barrier, nasal membrane, cornea and other eye membranes, and genito-urinary membranes). In particular there is great interest in oral delivery of therapeutic agents to avoid the use of more invasive means of administration and hence improve patient convenience and compliance.

Diverse drug delivery vehicles have been employed, among them liposomes, lipidic or polymeric nanoparticles, and microemulsions. These have improved the oral bioavailability of certain drugs, mostly by the protective effect they offer. However, for most relevant drugs, bioavailability remains very low and fails to achieve the minimal therapeutic goals.

Hence, a need exists for an efficient, specific, non-invasive, low-risk means to target various biological barriers for the non invasive delivery of various therapeutic agents such as peptides and polypeptides, macromolecule drugs and other therapeutic agents which include small molecules with low bioavailability.

SUMMARY

The inventors of the present invention have discovered that the absorption of certain therapeutic agents in a subject can be improved when administered in a composition described herein. For example, a therapeutic agent administered in a formulation in accordance with one or more embodiments exhibits an improved bioavailability (BA) relative to the same therapeutic agent administered via a similar route but in a composition substantially free of the medium chain fatty acid salt component described herein or having a lower amount of the medium chain fatty acid salt component described herein. Such improvement in relative BA may be on the order of at least about 1.5-, 2-, 3-, 5-, 10-, 50- or 100-fold. In some aspects, a composition described herein improves the absorption in the gastrointestinal (GI) tract of a therapeutic agent that is generally characterized by low or zero oral bioavailability and/or absorption. These therapeutic agents may have low or zero bioavailability, e.g., in aqueous solution, and in other oral formulations known in the art. In at least one aspect, a composition described herein improves bioavailability by enhancing the GI wall/barrier permeability to the drug molecules. For example, a composition described herein may facilitate absorption by permeating the GI wall/barrier primarily via unsealing of the tight junctions between GI epithelial cells, although it may also work by transcellular absorption.

The present inventors have devised a process for producing a pharmaceutical composition (bulk drug product) which involves preparing a water soluble composition comprising a therapeutically effective amount of at least one therapeutic agent and a medium chain fatty acid salt (and other ingredients—see below), drying (e.g. by lyophilization) the water soluble composition to obtain a solid powder, and suspending the lyophilized material (the solid powder) in a hydrophobic (oily) medium, preferably castor oil or glyceryl tricaprylate (including other ingredients e.g. PVP and surfactants and viscosity modifiers—see below), to produce a suspension containing in solid form the therapeutic agent and the medium chain fatty acid salt, thereby producing the bulk drug product, which must contain at least 10% by weight of medium chain fatty acid salt. The solid form may comprise a particle (e.g., consists essentially of particles, or consists of particles. The particle may be produced by lyophilization or by granulation. The bulk drug product may then be encapsulated in capsules which will be coated by a pH sensitive coating and may be used for oral delivery. A typical process for producing the claimed formulation is shown in FIG. 1, where insulin is exemplified as the active pharmaceutical ingredient (API) and the medium chain fatty acid salt is sodium octanoate (Na—C8), also termed sodium caprylate.

The present invention demonstrates delivery of the product to the intestine, which is a model for oral delivery, and from there to the bloodstream with high bioavailability.

Thus in one aspect the invention features a composition. The composition includes a therapeutic agent and a medium chain fatty acid salt associated with a substantially hydrophobic medium, preferably castor oil, wherein the therapeutic agent and the medium chain fatty acid salt thereof are in solid form, e.g. in the same solid form such as a particle, obtained by drying from an aqueous medium, e.g. by lyophilizing the aqueous medium, and wherein the medium chain fatty acid salt is present at 10% by weight or more, preferably 12-15%, e.g., about 12%, about 13%, about 14%, or about 15% or about 16%, or about 17%, and wherein the composition contains other ingredients (as described herein) but is substantially free of a "membrane fluidizing agent". "Membrane fluidizing agents" are defined as various linear, branched, aromatic and cyclic medium chain alcohols, in particular geraniol and octanol.

The present compositions of the invention are not emulsions. Almost all of the present compositions are oily suspensions and the amount of water in the compositions is very low; a few of the present compositions which are not suspensions incorporate a high amount (about 78% octanoic acid) and are solutions.

In the compositions of the invention, the therapeutic agent and medium chain fatty acid salt are in intimate contact with the substantially hydrophobic medium. For example, a powder comprising the therapeutic agent and medium chain fatty acid salt is coated, immersed or suspended in the substantially hydrophobic medium.

During the production process the aqueous medium which contains the therapeutic agent and the medium chain fatty acid salt and the other ingredients is dried (e.g. by lyophilization) to obtain the hydrophilic fraction which is a powder (e.g., a solid form comprising a plurality of particles), and a particle in that powder contains all the ingredients i.e. the therapeutic agent and medium chain fatty acid salt are together in a single particle. The solid form may be, for example, a granulated particle or a lyophilized particle.

In some embodiments, the therapeutic agent is selected from the group consisting of peptides, polysaccharides, polynucleotides, and small molecules. The therapeutic agent may be a protein. For example, the therapeutic agent may be insulin. In other embodiments, the therapeutic agent is a polynucleotide e.g. DNA or RNA compound. In some embodiments, the therapeutic agent is a small molecule, a poorly soluble drug, or a highly crystalline drug. The therapeutic agent may be a growth hormone. In at least one embodiment, the therapeutic agent is teriparatide. In some embodiments, the therapeutic agent may be leuprolide or alendronate or octreotide.

In some embodiments, the composition includes a plurality of medium chain fatty acid salts and derivatives thereof. For example, the solid particle may further include a plurality of medium chain fatty acid salts and derivatives thereof.

In some embodiments, the medium chain fatty acid salt is selected from the group consisting of sodium hexanoate, sodium heptanoate, sodium octanoate, sodium nonanoate, sodium decanoate, sodium undecanoate, sodium dodecanoate, sodium tridecanoate, and sodium tetradecanoate or a combination thereof. In accordance with one or more embodiments, the composition is substantially free of sodium dodecanoate, sodium tridecanoate, and sodium tetradecanoate. In some embodiments, the medium chain fatty acid is sodium octanoate and the sodium octanoate is present at a concentration of above 10% e.g. about 11% to about 50% weight/weight (wt/wt).

In some embodiments, the substantially hydrophobic medium comprises a triglyceride. For example, the triglyceride may be selected from the group consisting of glyceryl tributyrate, glyceryl monooleate, glyceryl monocaprylate and glyceryl tricaprylate.

In some embodiments, the substantially hydrophobic medium comprises mineral oil, castor oil, olive oil, corn oil, coconut oil, peanut oil, soybean oil, cotton seed oil, sesame oil or canola oil, or combinations thereof.

In some embodiments the water-soluble composition contains a medium chain fatty acid salt and the hydrophobic medium contains the corresponding medium chain fatty acid; in some particular embodiments the medium chain fatty acid salt is a salt of octanoic acid such as sodium octanoate and the medium chain fatty acid is octanoic acid.

In some embodiments the water-soluble composition contains a medium chain fatty acid salt and the hydrophobic medium contains the corresponding medium chain monoglyceride or the corresponding medium chain triglyceride or a combination thereof; in some particular embodiments the medium chain fatty acid salt is sodium octanoate and the monoglyceride is glyceryl monocaprylate and the triglyceride is glyceryl tricaprylate.

In some embodiments, the composition further includes one or more excipients. The excipients may be a salt e.g $MgCl_2$ or an amine containing compound or mannitol. In some embodiments, the excipient is in the same solid form as the therapeutic agent.

In some embodiments the excipient is a stabilizer. The inventors unexpectedly found that although polyvinylpyrolidine (PVP) in particular PVP-12 is known in the art as a stabilizer, in formulations of the invention it serves to increase the effect of the permeability enhancer on absorbance of the therapeutic agent.

In some embodiments, the composition further includes one or more surfactants. For example, the surfactant may be selected from the group consisting of sorbitan monopalmitate (Span-40®), polyoxyethylenesorbitan monooleate (Tween80), lecithin, and glyceryl monooleate (GMO). In one or more embodiments, the surfactant comprises from about 0.1% to about 6% by weight of the composition.

In preferred embodiments, the composition is an oral dosage form. For example, the composition may be filled in a hard or soft capsule. In some embodiments, the composition is in the form of a suppository. In accordance with one or more embodiments, the composition may be in the form of an enema fleet.

In some embodiments, the bioavailability of the therapeutic agent, when administered to a subject, is at least 1.5-2% relative to parenteral (subcutaneous or intravenous) administration. In some embodiments, the composition, when administered to a subject, provides above 2%, above 3%, above 5%, above 10%, or above 20% or above 30% absorption of the therapeutic agent across a biological barrier. The levels of absorption achieved produce the therapeutic levels needed for the indication concerned.

In one aspect, the invention features a method of treating a disorder in a subject. The method includes administering to the subject any one of the compositions described herein.

In some embodiments, the composition is administered orally. In other embodiments, the composition is administered rectally, sublingually or via buccal administration.

In some embodiments, the disorder may be anemia. In accordance with one or more embodiments, the disorder is osteoporosis. The disorder may be female infertility. In other embodiments, the disorder is growth failure or growth hormone deficiency. In at least one embodiment, the disorder is HIV-related weight loss or wasting, acromegaly or diabetes.

In some embodiments the therapeutic agent is octreotide and the disorder is acromegaly, abnormal GI motility, gastroparesis, diarrhea or portal hypertension.

In some embodiments, the method may include encapsulating the suspension to form a capsule. The method may further include coating the capsule.

In some embodiments, the method may include providing instructions to administer the capsule to a subject. The instructions may relate to administering the capsule to a subject for any indication described herein. In one aspect, the invention features capsules provided with instructions relating to administering the capsule to a subject for any indication described herein.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

Throughout this application, various publications, including United States patents, are referenced by author and year and patents and applications by number. The disclosures of these publications and patents and patent applications in their entireties are hereby incorporated by reference into this application in order to more fully describe the state of the art to which this invention pertains.

BRIEF DESCRIPTION OF THE DRAWINGS

Various aspects of at least one embodiment are discussed below with reference to the accompanying Figures. In the Figures, which are not intended to be drawn to scale, each identical or nearly identical component that is illustrated in various figures is represented by a like numeral. For purposes of clarity, not every component may be labeled in every drawing. The Figures are provided for the purposes of illustration and explanation and are not intended as a definition of the limits of the invention. In the Figures.

DETAILED DESCRIPTION

Figure 1:
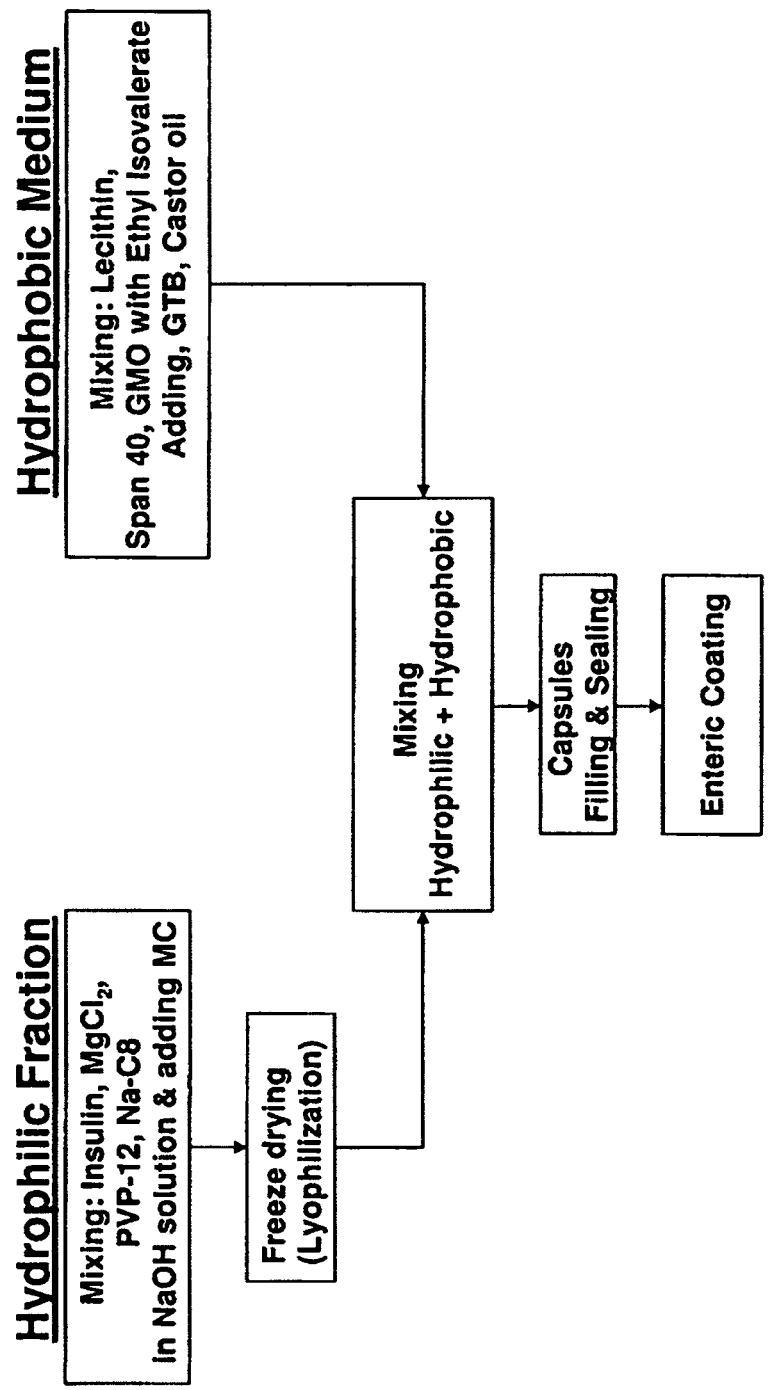
FIG. 1 presents a process for production of an insulin formulation of a composition in accordance with one or more embodiments as referenced in the accompanying Examples.

The compositions described herein can be administered to a subject to provide for improved bioavailability of a therapeutic agent.

Pharmaceutical Compositions:

The pharmaceutical compositions described herein include a therapeutic agent and a medium chain fatty acid salt in intimate contact or association with a substantially hydrophobic medium. For example, the therapeutic agent and the medium chain fatty acid or derivative thereof may be coated, suspended, sprayed by or immersed in a substantially hydrophobic medium forming a suspension. The compositions of the invention are not emulsions. Almost all of the compositions are oily suspensions and the amount of water in the compositions is very low; a few of the present compositions which are not suspensions incorporate a high amount (about 78% octanoic acid) and are solutions by visual analysis. The suspension may be a liquid suspension incorporating solid material, or a semi-solid suspension incorporating solid material (an ointment).

Many of the compositions described herein comprise a suspension which comprises an admixture of a hydrophobic medium and a solid form wherein the solid form comprises a therapeutically effective amount of a therapeutic agent and at least one salt of a medium chain fatty acid, and wherein the medium chain fatty acid salt is present in the composition at an amount of 10% or more by weight. The solid form may comprise a particle (e.g., consist essentially of particles, or consist of particles). The particle may be produced by lyophilization or by granulation. In some embodiments, preferably after milling, 90% (v/v) of the particles are below 130 microns, and 50% (v/v) of the particles are below 45 microns.

A cargo compound is a therapeutic agent (e.g. insulin) or a test compound (e.g. high molecular weight dextran) which is formulated as described herein within the compositions of the invention.

The inventors were particular to include in many of the compositions of the invention only excipients which are generally recognized as safe, based on available data on human use, animal safety and regulatory guidelines (e.g. GRAS excipients). Some compositions of the invention may have other types of excipients (e.g. non-GRAS). In some embodiments the compositions of the invention have amounts of excipients that are within the maximum daily doses as noted in such available data for each specific excipient.

The medium chain fatty acid salt may generally facilitate or enhance permeability and/or absorption of the therapeutic agent. In some embodiments the medium chain fatty acid salts include derivatives of medium chain fatty acid salts. The therapeutic agent and the medium chain fatty acid salt are in solid form, for example, a solid particle such as a lyophilized particle, granulated particle, pellet or microsphere. In preferred embodiments, the therapeutic agent and the medium chain fatty acid salt are both in the same solid form, e.g., both in the same particle. In other embodiments, the therapeutic agent and the medium chain fatty acid salt may each be in a different solid form, e.g. each in a distinct particle. The compositions described herein are substantially free of any "membrane fluidizing agents" defined as linear, branched, aromatic and cyclic medium chain alcohols, in particular geraniol and octanol. For example the compositions preferably include no membrane fluidizing agents but certain embodiments may include for example less than 1% or less than 0.5% or less than 0.1% by weight of membrane fluidizing agents.

Unlike emulsions, where water is an essential constituent of the formulation, the compositions described herein provide a solid form such as a particle containing the therapeutic agent, which is then associated with the hydrophobic (oily) medium. The amount of water in the compositions is generally less than 3% by weight, usually less than about 2% or about 1% or less by weight.

The compositions described herein are suspensions which comprise an admixture of a hydrophobic medium and a solid form wherein the solid form comprises a therapeutically effective amount of a therapeutic agent and at least one salt of a medium chain fatty acid. The solid form may be a particle (e.g., consist essentially of particles, or consist of particles). The particle may be produced by lyophilization or by granulation. The medium chain fatty acid salt is generally present in the compositions described herein at an amount of 10% or more by weight. In certain embodiments the medium chain fatty acid salt is present in the composition at an amount of 10%-50%, preferably 11%-18% or about 11%-17% or 12%-16% or 12%-15% or 13%-16% or 13%-15% or 14%-16% or 14%-15% or 15%-16% or most preferably 15% or 16% by weight, and the medium chain fatty acid has a chain length from about 6 to about 14 carbon atoms preferably 8, 9 or 10 carbon atoms.

In some embodiments in the compositions described above, the solid form including the therapeutic agent also includes a stabilizer (e.g., a stabilizer of protein structure). Stabilizers of protein structure are compounds that stabilize protein structure under aqueous or non-aqueous conditions or can reduce or prevent aggregation of the therapeutic agent, for example during a drying process such as lyophilization or other processing step. Stabilizers of structure can be polyanionic molecules, such as phytic acid, polyvalent ions such as Ca, Zn or Mg, saccharides such as a disaccharide (e.g., trehalose, maltose) or an oligo or polysaccharide such as dextrin or dextran, or a sugar alcohol such as mannitol, or an amino acid such as glycine, or polycationic molecules, such as spermine, or surfactants such as polyoxyethylene sorbitan monooleate (Tween 80) or pluronic acid. Uncharged polymers, such as mannitol, methyl cellulose and polyvinyl alcohol, are also suitable stabilizers.

Although polyvinylpyrrolidone (PVP) is known in the art as a stabilizer, the inventors unexpectedly found that, in the compositions of the invention described herein, PVP, in particular PVP-12, serves to increase the effect of the permeability enhancer in a synergistic manner; furthermore, increasing the level of PVP-12 to 10% increased the absorption of the therapeutic agent into the blood due to the improved activity of the formulations. The inventors demonstrated that dextran had a similar (but lower) effect as PVP did. Other matrix forming polymers have a similar effect.

In some embodiments, such as when the therapeutic agent is a small molecule, a bulking agent may be added, for example, mannitol or glycin.

In certain embodiments of the compositions described herein the therapeutic agent is a protein, a polypeptide, a peptide, a glycosaminoglycan, a small molecule, a polysaccharide or a polynucleotide inter alia, such as octreotide, growth hormone, parathyroid hormone, parathyroid hormone amino acids 1-34 [PTH(1-34) termed teriparatide], a low molecular weight heparin or fondaparinux inter alia. Low molecular weight heparins are defined as heparin salts having an average molecular weight of less than 8000 Da and for which at least 60% of all chains have a molecular weight less than 8000 Da.

In a particular embodiment of the compositions described herein the salt of the fatty acid is sodium octanoate and the hydrophobic medium is castor oil; in another particular embodiment the composition further comprises glyceryl monooleate and sorbitan monopalmitate or glyceryl monocaprylate and glyceryl tricaprylate and polyoxyethylenesorbitan monooleate; in another particular embodiment the composition further comprises glyceryl tributyrate, lecithin, ethylisovalerate and at least one stabilizer. In particular embodiments the therapeutic agent is octreotide, growth hormone, parathyroid hormone, teriparatide, interferon-alfa (IFN-α), a low molecular weight heparin, fondaparinux, siRNA, somatostatin and analogs (agonists) thereof including peptidomimetics, exenatide, vancomycin or gentamicin inter alia.

Therapeutic Agents:

The pharmaceutical compositions described herein can be used with a variety of therapeutic agents (also termed active pharmaceutical ingredient=API). In some embodiments, the pharmaceutical composition includes a plurality of therapeutic agents (effectors). The therapeutic agents can either be in the same solid form (e.g., in the same particle), or the therapeutic agents can each be in an independent solid form (e.g., each in different particles). In some embodiments, the therapeutic agent is in the form of a particle, for example, a granulated or solid particle. The particle is associated with or is in intimate contact with a substantially hydrophobic medium, for example, a hydrophobic medium described herein.

Therapeutic agents that can be used in the compositions described herein include any molecule or compound serving as, for example, a biological, therapeutic, pharmaceutical, or diagnostic agent including an imaging agent. The therapeutic agents include drugs and other agents including, but not limited to, those listed in the United States Pharmacopeia and in other known pharmacopeias. Therapeutic agents are incorporated into the formulations of the invention without any chemical modification. Therapeutic agents include proteins, polypeptides, peptides, polynucleotides, polysaccharides and small molecules.

The term "small molecule" is understood to refer to a low molecular weight organic compound which may be synthetically produced or obtained from natural sources and typically has a molecular weight of less than 2000 Da, or less than 1000 Da or even less than 600 Da e.g. less than or about 550 Da or less than or about 500 Da or less than or about 400 Da; or about 400 Da to about 2000 Da; or about 400 Da to about 1700 Da. Examples of small molecules are ergotamine (molecular weight=582 Da), fondaparinux (molecular weight=1727 Da), leuprolide (molecular weight=1209 Da), vancomycin (molecular weight=1449 Da), gentamicin (molecular weight=478 Da) and doxorubicin (molecular weight=544).

The term "polynucleotide" refers to any molecule composed of DNA nucleotides, RNA nucleotides or a combination of both types which comprises two or more of the bases guanidine, citosine, timidine, adenine, uracil or inosine, inter alia. A polynucleotide may include natural nucleotides, chemically modified nucleotides and synthetic nucleotides, or chemical analogs thereof and may be single-stranded or double-stranded. The term includes "oligonucleotides" and encompasses "nucleic acids".

By "small interfering RNA" (siRNA) is meant an RNA molecule (ribonucleotide) which decreases or silences (prevents) the expression of a gene/mRNA of its endogenous or cellular counterpart. The term is understood to encompass "RNA interference" (RNAi), and "double-stranded RNA" (dsRNA).

By "polypeptide" is meant a molecule composed of covalently linked amino acids and the term includes peptides, polypeptides, proteins and peptidomimetics. A peptidomimetic is a compound containing non-peptidic structural elements that is capable of mimicking the biological action(s) of a natural parent peptide. Some of the classical peptide characteristics such as enzymatically scissile peptidic bonds are normally not present in a peptidomimetic.

The term "amino acid" refers to a molecule which consists of any one of the 20 naturally occurring amino acids, amino acids which have been chemically modified or synthetic amino acids.

By "polysaccharide" is meant a linear or branched polymer composed of covalently linked monosaccharides; glucose is the most common monosaccharide and there are normally at least eight monosaccharide units in a polysaccharide and usually many more. Polysaccharides have a general formula of $C_x(H_2O)_y$ where x is usually a large number between 200 and 2500. Considering that the repeating units in the polymer backbone are often six-carbon monosaccharides, the general formula can also be represented as $(C_6H_{10}O_5)_n$ where $40 \leq n \leq 3000$ i.e. there are normally between 40 and 3000 monosaccharide units in a polysaccharide.

A "glycosaminoglycan" is a polysaccharide that contains amino containing sugars.

Exemplary anionic therapeutic agents include polynucleotides from various origins, and particularly from human, viral, animal, eukaryotic or prokaryotic, plant, or synthetic origin, etc including systems for therapeutic gene delivery. A polynucleotide of interest may be of a variety of sizes, ranging from, for example, a simple trace nucleotide to a gene fragment, or an entire gene. It may be a viral gene or a plasmid. Exemplary polynucleotides serving as therapeutic agents include specific DNA sequences (e.g., coding genes), specific RNA sequences (e.g., RNA aptamers, antisense RNA, short interfering RNA (siRNA) or a specific inhibitory RNA (RNAi)), poly CPG, or poly I:C synthetic polymers of polynucleotides.

Alternatively, the therapeutic agent can be a protein, such as, for example, an enzyme, a hormone, an incretin, a proteoglycan, a ribozyme, a cytokine, a peptide, an apolipoprotein, a growth factor, a bioactive molecule, an antigen, or an antibody or fragment(s) thereof, etc. The peptide can be a small peptide e.g. from about 2 to about 40 amino acids, examples include fibrinogen-receptor antagonists (RGD-containing peptides which are tetrapeptides having an average molecular weight of about 600. Exemplary peptides are somatostatin and analogs thereof e.g. octreotide and lanreotide (Somatuline) which are both cyclic octapeptides and pasireotide (SOM-230) which is a cyclic hexapeptide (Weckbecker et al, 2002, Endocrinology 143(10) 4123-4130; Schmid, 2007, Molecular and Cellular Endocrinology 286, 69-74). Other exemplary peptides are glatiramer acetate (Copaxone®) which is a tetrapeptide, terlipressin which is a 12 amino acid peptide analog (agonist) of lysine vasopressin (ADH) and exenatide, a 39 amino acid peptide which is an incretin mimetic agent, and other analogs of glucagon-like peptide-1(GLP-1). (Byetta® is the trade name for exenatide (Eli Lilly and Company/Amylin Pharmaceuticals, Inc.). Other peptides include dalargin which is a hexapeptide, and kyotorphin which is a dipeptide. Peptides include growth hormone releasing peptides which are peptides of about 12 amino acids or less; see for example peptides disclosed in U.S. Pat. No. 4,411,890 (Momany) and U.S. Pat. No. 4,839,344 (Bowers et al)

Examples of other peptides which can be used in the practice of this invention are those disclosed in U.S. Pat. No. 4,589,881 (30 or more amino acid residues) of Pierschbacher et al; U.S. Pat. No. 4,544,500 (20-30 residues) of Bittle et al; and EP0204480 (>34 residues) of Dimarchi et al and teriparatide. In some embodiments, the therapeutic agent can include a polysaccharide, such as a glycosaminoglycan. Exemplary glycosaminoglycans include heparin, heparin derivatives, heparan sulfate, chondroitin sulfate, dermatan sulfate, and hyaluronic acid. Examples of heparin derivatives include, but are not limited to, low molecular weight heparins such as enoxaparin, dalteparin and tinzaparin. A therapeutic agent with a heparin-like effect is fondaparinux.

Other examples of therapeutic agents include, but are not limited to hormones such as insulin, erythropoietin (EPO), glucagon-like peptide 1 (GLP-1), melanocyte stimulating hormone (alfa-MSH), parathyroid hormone (PTH), teriparatide, growth hormone (GH), leuprolide, leuprolide acetate, factor VIII, growth hormone releasing hormone (GHRH), peptide YY amino acids 3-36 ($PYY_{(3-36)}$), calcitonin, somatotropin, somatostatin, somatomedin, interleukins such as interleukin-2 (IL-2), alfa-1-antirypsin, granulocyte/monocyte colony stimulating factor (GM-CSF), granulocyte colony stimulating factor (G-CSF), T20, testosterone, interferons such as interferon-alfa (IFN-α) IFN-β and IFN-γ, luteinizing hormone (LH), follicle-stimulating hormone (FSH), human chorionic gonadotropin (hCG), enkephalin, dalargin, kyotorphin, basic fibroblast growth factor (bFGF), hirudin, hirulog, luteinizing hormone releasing hormone (LHRH), gonadotropin releasing hormone (GnRH) analog, brain-derived natriuretic peptide (BNP), tissue plasminogen activator (TPA), oxytocin, and analogs and combinations thereof.

Other examples of therapeutic agents include, but are not limited to analgesic agents, anti-migraine agents, anti-coagulant agents, anti-emetic agents, cardiovascular, anti-hypertensive and vasodilator agents, sedatives, narcotic antagonists, chelating agents, anti-diuretic agents and antineoplastic agents.

Analgesics include, but are not limited to, fentanyl, sufentanil, butorphanol, buprenorphine, levorphanol, morphine, hydromorphone, hydrocodeine, oxymorphone, methadone, lidocaine, bupivacaine, diclofenac, naproxen, paverin, and analogs thereof. Anti-migraine agents include, but are not limited to naratriptan, naproxen, almotriptan, butalbital, frovatriptan, sumatriptan, rizatriptan, acetaminophen, isomethepene, butorphanol, dichloralphenazone, ergot alkaloids such as dihydroergotamine and ergotamine, nonsteroidal anti-inflammatory drugs (NSAIDs) such as ketoprofen and ketorolac, eletriptan, butorphanol, topiramate, zolmitriptan, caffeine, aspirin and codeine, and analogs and combinations thereof.

Anti-coagulant agents include, but are not limited to heparin, hirudin, low molecular weight heparins and analogs thereof and fondaparinux. Anti-emetic agents include but are not limited to scopolamine, ondansetron, domperidone, etoclopramide, and analogs thereof. Cardiovascular, anti-hypertensive and vasodilator agents include, but are not limited to, diltiazem, clonidine, nifedipine, verapamil, isosorbide-5-mononitrate, organic nitrates, nitroglycerine and analogs thereof. Sedatives include, but are not limited to, benzodiazeines, phenothiozines and analogs thereof. Narcotic antagonists include, but are not limited to, naltrexone, naloxone and analogs thereof. Chelating agents include, but are not limited to deferoxamine and analogs thereof. Anti-diuretic agents include, but are not limited to, desmopressin, vasopressin and analogs (agonists) thereof such as terlipressin; the trade name of terlipressin is Glypressin®. Antineoplastic agents include, but are not limited to, 5-fluorouracil, bleomycin, vincristine, procarbazine, temezolamide, 6-thioguanine, hydroxyurea, cytarabine, cyclophosphamide, doxorubicin, vinca alkaloid, epirubicin, etoposide, ifosfamide, carboplatin and other platinum based antineoplastic drugs (such as carboplatin (Paraplatin®, tetraplatin, oxaliplatin, aroplatin and transplatin), vinblastine, vinorelbine, chlorambucil, busulfan, mechlorethamine, mitomycin, dacarbazine, thiotepa, daunorubicin, idarubicin, mitoxantrone, esperamicin A1, dactinomycin, plicamycin, carmustine, lomustine (CCNU), tauromustine, streptozocin, melphalan, dactinomycin, procarbazine, dexamethasone, prednisone, 2-chlorodeoxyadenosine, cytarabine, docetaxel, fludarabine, gemcitabine, herceptin, hydroxyurea, irinotecan, methotrexate, rituxin, semustine, tomudex and topotecan, taxol and taxol-like compounds and analogs and combinations thereof.

Additional examples of therapeutic agents include, but are not limited to coagulation factors and neurotrophic factors, anti-TNF antibodies and fragments of TNF receptors.

Therapeutic agents also include pharmaceutically active agents selected from the group consisting of vitamin B12, a bisphosphonate (e.g., disodium pamidronate, alendronate, etidronate, tiludronate, risedronate, zoledronic acid, sodium clodronate, or ibandronic acid), taxol, caspofungin, or an aminoglycoside antibiotic. Additional therapeutic agents include a toxin, or an antipathogenic agent, such as an antibiotic (e.g. vancomycin), an antiviral, an antifungal, or an anti-parasitic agent. The therapeutic agent can itself be directly active or can be activated in situ by the composition, by a distinct substance, or by environmental conditions.

In some embodiments, the composition can include a plurality of therapeutic agents (combination drugs). For example, the composition can include Factor VIII and vWF, GLP-1 and PYY, IFN-α and nucleotide analogues (i.e. ribavirin), and alendronate or insulin and GLP-1.

In some embodiments, the composition can include a small molecule and a peptide or protein. Exemplary combinations include a combination of IFN-α and nucleotide analogues (i.e. ribavirin) for the treatment of hepatitis C, teriparatide and alendronate for treatment of bone disorders, a combination of GH plus the medications for HIV therapy (e.g., HAART) to simultaneously treat the viral infection and the accompanying HIV lipodystrophy or AIDS wasting side effects. Combinations of two small molecules can be used when one of them generally has poor absorption or bioavailability even if the other generally has effective absorption or bioavailability, such as some antibiotics (e.g., a combination of vancomycin and an aminoglycoside such as gentamicin. Exemplary combinations for the treatment and prevention of metabolic disorders such as diabetes and obesity also include combination of insulin and metformin, insulin and rosiglitazone, GLP-1 (or exenatide) and metformin, and GLP-1 (or exenatide) and rosiglitazone.

Indications and conditions which may be treated by fondaparinux formulated as described herein include deep vein thrombosis, hip or knee replacement, and bed-bound patients.

In some embodiments of the compositions described herein, the composition includes a combination of a protein or peptide with small molecules that either do or do not have good absorption or bioavailability. For example, a composition can include at least one therapeutic agent that may generally be characterized as poorly absorbable or poorly bioavailable. The composition can also be used for the administration of therapeutic agents that are absorbed in the stomach and/or intestine, but cause irritation to the stomach and/or intestine and therefore are difficult to tolerate. In such a situation, a subject could benefit if the bioavailability of the therapeutic agent were enhanced or if more of the therapeutic agent were absorbed directly into the blood stream; if less therapeutic agent is administered there will clearly be less chance of causing irritation to the stomach and/or intestine. Thus compositions of the invention are envisaged which comprises therein two or more therapeutic agents.

In general, the composition may include from about 0.01% to about 50% by weight of the therapeutic agent e.g. about 0.01, 0.02 0.05, 1, 2, 3, 4, 5, 6, 7, 8, 9, 10, 15, 20, 25, 30, 35, 40, 45, or 50% by weight. The maximum included in the composition is often in the range of about 6%-33% by weight of the therapeutic agent.

In some embodiments of the compositions described herein, the solid form including the therapeutic agent also includes a stabilizer (e.g., a stabilizer of protein structure). Stabilizers of protein structure are compounds that stabilize protein structure under aqueous or non-aqueous conditions or can reduce or prevent aggregation of the therapeutic agent, for example during a drying process such as lyophilization or other processing step. Stabilizers of structure can be polyanionic molecules, such as phytic acid, polyvalent ions such as Ca, Zn or Mg, saccharides such as a disaccharide (e.g., trehalose, maltose) or an oligo or polysaccharide such as dextrin or dextran, or a sugar alcohol such as mannitol, or an amino acid such as glycine, or polycationic molecules, such as spermine, or surfactants such as Tween 80 or Span 40 or pluronic acid. Uncharged polymers, such as methyl cellulose and polyvinyl alcohol, are also suitable stabilizers.

Medium Chain Fatty Acid Salt:

The compositions described herein include the salt of a medium chain fatty acid or a derivative thereof in a solid form. For example, the salt of the medium chain fatty acid is in the form of a particle such as a solid particle. In some embodiments, the particle may be characterized as a granulated particle. In at least some embodiments, the solid form may generally result from a spray drying or evaporation process. In preferred embodiments, the salt of the medium chain fatty acid is in the same particle as the therapeutic agent. For example, the therapeutic agent and the salt of the medium chain fatty acid can be prepared together by first preparing a solution such as an aqueous solution comprising both the therapeutic agent and the salt of the medium chain fatty acid and co-lyophilizing the solution to provide a solid form or particle that comprises both the therapeutic agent and the salt of the medium chain fatty acid (and other ingredients). As described above, the resulting solid particles are associated with a hydrophobic medium. For example, the solid particles may be suspended or immersed in a hydrophobic medium In different embodiments of the compositions described herein the medium chain fatty acid salt may be in the same particle or in a different particle than that of the API. It was found that bioavailability of a cargo compound was lower if the medium chain fatty acid was in a different particle than the therapeutic agent i.e. there was improved bioavailability if the medium chain fatty acid salt and the cargo compound were dried after solubilization together in the hydrophilic fraction. It is believed that if the medium chain fatty acid salt and the cargo compound are dried after solubilization together in the hydrophilic fraction then they are in the same particle in the final powder.

Medium chain fatty acid salts include those having a carbon chain length of from about 6 to about 14 carbon atoms. Examples of fatty acid salts are sodium hexanoate, sodium heptanoate, sodium octanoate (also termed sodium caprylate), sodium nonanoate, sodium decanoate, sodium undecanoate, sodium dodecanoate, sodium tridecanoate, and sodium tetradecanoate. In some embodiments, the medium chain fatty acid salt contains a cation selected from the group consisting of potassium, lithium, ammonium and other monovalent cations e.g. the medium chain fatty acid salt is selected from lithium octanoate or potassium octanoate or arginine octanoate or other monovalent salts of the medium chain fatty acids. The inventors found that raising the amount of medium chain fatty acid salt increased the bioavailability of the resulting formulation. In particular, raising the amount of medium chain fatty acid salt, in particular sodium octanoate, above 10% to a range of about 12% to 15% increased the bioavailability of the therapeutic agents in the pharmaceutical compositions described herein.

In general, the amount of medium chain fatty acid salt in the compositions described herein may be from 10% up to about 50% by weight of the bulk pharmaceutical composition. For example, the medium chain fatty acid salt may be present at an amount of about 10%-50%, preferably about 11%-40% most preferably about 11%-28% by weight for example at about 12%-13%, 13%-14%, 14%-15%, 15%-16%, 16%-17%, 17%-18%, 18%-19%, 19%-20%, 20%-21%, 21%-22%, 22%-23%, 23%-24%, 24%-25%, 25%-26%, 26%-27%, or 27%-28% by weight of the bulk pharmaceutical composition. In other embodiments the medium chain fatty acid salt may be present at an amount of at least about 11%, at least about 12%, at least about 13%, at least about 14%, at least about 15% at least about 16%, at least about 17%, at least about 18%, at least about 19%, at least about 20%, at least about 21%, at least about 22%, at least about 23%, at least about 24%, at least about 25%, at least about 26%, at least about 27% or at least about 28% by weight of the bulk pharmaceutical composition. In specific embodiments the medium chain fatty acid salt (sodium, potassium, lithium or ammonium salt or a mixture thereof) is present at about 12%-21% by weight of the bulk pharmaceutical composition preferably 11%-18% or about 11%-17% or 12%-16% or 12%-15% or 13%-16% or 13%-15% or 14%-16% or 14%-15% or 15%-16% or most preferably 15% or 16%. In specific embodiments the medium chain fatty acid salt (having a carbon chain length of from about 6 to about 14 carbon atoms particularly 8, 9 or 10 carbon atoms) is present at about 12%-21% by weight of the bulk pharmaceutical composition preferably 11%-18% about 11%-17% or 12%-16% or 12%-15% or 13%-16% or 13%-15% or 14%-16% or 14%-15% or 15%-16% or most preferably 15% or 16%. In specific embodiments the medium chain fatty acid salt (for example salts of octanoic acid, salts of suberic acid, salts of geranic acid) is present at about 12%-21% by weight of the bulk pharmaceutical composition preferably 11%-18% about 11%-17% or 12%-16% or 12%-15% or 13%-16% or 13%-15% or 14%-16% or 14%-15% or 15%-16% or most preferably 15% or 16%. In certain embodiments the medium chain fatty acid salt is present in the solid powder at an amount of 50% to 90%, preferably at an amount of 70% to 80%.

One embodiment of the invention comprises a composition comprising a suspension which consists essentially of an admixture of a hydrophobic medium and a solid form wherein the solid form comprises a therapeutically effective amount of a therapeutic agent and at least one salt of a medium chain fatty acid, and wherein the medium chain fatty acid salt is not a sodium salt. The salt may be the salt of another cation e.g. lithium, potassium or ammonium; an ammonium salt is preferred.

Matrix Forming Polymer:

In certain embodiments the composition of the invention comprises a suspension which comprises an admixture of a hydrophobic medium and a solid form wherein the solid form comprises a therapeutically effective amount of a therapeutic agent, at least one salt of a medium chain fatty acid and a matrix forming polymer, and wherein the matrix forming polymer is present in the composition at an amount of 3% or more by weight. In certain embodiments the composition comprises a suspension which consists essentially of an admixture of a hydrophobic medium and a solid form wherein the solid form comprises a therapeutically effective amount of a therapeutic agent, at least one salt of a medium chain fatty acid and a matrix forming polymer, and wherein the matrix forming polymer is present in the composition at an amount of 3% or more by weight. In particular embodiments the matrix forming polymer is dextran or polyvinylpyrrolidone (PVP). In particular embodiments the polyvinylpyrrolidone is present in the composition at an amount of about 2% to about 20% by weight, preferably at an amount of about 3% to about 18% by weight, more preferably at an amount of about 5% to about 15% by weight, most preferably at an amount of about 10% by weight. In certain particular embodiments the polyvinylpyrrolidone is PVP-12 and/or has a molecular weight of about 3000. Other matrix forming polymers have a similar effect in the compositions of the invention; such matrix forming polymers include ionic polysaccharides (for example alginic acid and alginates) or neutral polysaccharides (for example dextran and HPMC), polyacrylic acid and poly methacrylic acid derivatives and high molecular weight organic alcohols (for example polyvinyl alcohol).

Protease Inhibitors:

It is generally accepted in the art of delivery of proteins, polypeptides and peptides that protease inhibitors normally have to be added to the formulation to prevent degradation of the API. However in the formulations of the instant invention it is not necessary to add protease inhibitors. The formulations of the invention appear to confer stability of the therapeutic agent to protease degradation within the time-frame of activity i.e. the formulations of the invention are apparently environment inhibitory for enzyme activity. Additionally, the inventors performed an experiment wherein the protease inhibitor aprotinin was added to a formulation and this had no beneficial effect on activity. A similar experiment was performed where the protease inhibitor ϵ-aminocaproic acid was added to a formulation and this too had no beneficial effect on activity. Therefore, in some embodiments, a pharmaceutical composition described herein is substantially free of a protease inhibitor.

Hydrophilic Fraction:

In embodiments of the invention, the above compounds, including the therapeutic agent and the medium chain fatty acid salt are solubilized in an aqueous medium and then dried to produce a powder. The drying process may be achieved for example by lyophilization or granulation. The powder obtained is termed the "hydrophilic fraction". In the hydrophilic fraction water is normally present at an amount of less than 6%.

Lyophilization may be carried out as shown in the Examples herein and by methods known in the art e.g. as described in *Lyophilization: Introduction and Basic Principles*, Thomas Jennings, published by Interpharm/CRC Press Ltd (1999, 2002) The lyophilizate may optionally be milled (e.g. below 150 micron) or ground in a mortar. During industrial production the lyophilizate is preferably milled before mixing of the hydrophilic fraction and the hydrophobic medium in order to produce batch-to-batch reproducibility.

Granulation may be carried out as shown in the Examples herein and by methods known in the art e.g. as described in *Granulation*, Salman et al, eds, Elsevier (2006) and in *Handbook of Pharmaceutical Granulation Technology*, $2^{nd}$ edition, Dilip M. Parikh, ed., (2005

Various binders may be used in the granulation process such as celluloses (including microcrystalline celluloses), lactoses (e.g. lactose monohydrate), dextroses, starch and mannitol and other binders as described in the previous two references.

Hydrophobic Medium:

Oil:

As described above, in the compositions of the invention described herein the therapeutic agent and the medium chain fatty acid salt are in intimate contact or association with a hydrophobic medium. For example, one or both may be coated, suspended, immersed or otherwise in association with a hydrophobic medium. Suitable hydrophobic mediums can contain, for example, aliphatic, cyclic or aromatic molecules. Examples of a suitable aliphatic hydrophobic medium include, but are not limited to, mineral oil, fatty acid monoglycerides, diglycerides, triglycerides, ethers, esters, and combinations thereof. Examples of a suitable fatty acid are octanoic acid, decanoic acid and dodecanoic acid, also C7 and C9 fatty acids and di-acidic acids such as sebacic acid and suberic acid, and derivatives thereof. Examples of triglycerides include, but are not limited to, long chain triglycerides, medium chain triglycerides, and short chain triglycerides. For example, the long chain triglyceride can be castor oil or coconut oil or olive oil, and the short chain triglyceride can be glyceryl tributyrate and the medium chain triglyceride can be glyceryl tricaprylate. Monoglycerides are considered to be surfactants and are described below. Exemplary esters include ethyl isovalerate and butyl acetate. Examples of a suitable cyclic hydrophobic medium include, but are not limited to, terpenoids, cholesterol, cholesterol derivatives (e.g., cholesterol sulfate), and cholesterol esters of fatty acids. A non-limiting example of an aromatic hydrophobic medium includes benzyl benzoate.

In some embodiments of the compositions described herein, it is desirable that the hydrophobic medium include a plurality of hydrophobic molecules. In some embodiments of the compositions described herein the hydrophobic medium also includes one or more surfactants (see below).

In some embodiments of the compositions described herein, the hydrophobic medium also includes one or more adhesive polymers such as methylcellulose, ethylcellulose, hydroxypropylmethylcellulose (HPMC), or poly(acrylate) derivative Carbopol®934P (C934P). Such adhesive polymers may assist in the consolidation of the formulation and/or help its adherence to mucosal surfaces.

Surface Active Agents (Surfactants):

The compositions of this invention described herein can further include a surface active agent. For example, the surface active agent can be a component of the hydrophobic medium as described above, and/or the surface active agent can be a component of a solid form as described above, for example in the solid form or particle that includes the therapeutic agent.

Suitable surface active agents include ionic and non-ionic surfactants. Examples of ionic surfactants are lecithin (phosphatidyl choline), bile salts and detergents. Examples of non-ionic surfactants include monoglycerides, cremophore, a polyethylene glycol fatty alcohol ether, a sorbitan fatty acid ester, a polyoxyethylene sorbitan fatty acid ester, Solutol HS15, or a poloxamer or a combination thereof. Examples of monoglycerides are glyceryl monocaprylate (also termed glyceryl monooctanoate), glyceryl monodecanoate, glyceryl monolaurate, glyceryl monomyristate, glyceryl monostearate, glyceryl monopalmitate, and glyceryl monooleate. Examples of sorbitan fatty acid esters include sorbitan monolaurate, sorbitan monooleate, and sorbitan monopalmitate (Span 40), or a combination thereof. Examples of polyoxyethylene sorbitan fatty acid esters include polyoxyethylene sorbitan monooleate (Tween 80), polyoxyethylene sorbitan monostearate, polyoxyethylene sorbitan monopalmitate or a combination thereof. The commercial preparations of monoglycerides that were used also contain various amounts of diglycerides and triglycerides.

Compositions described herein including a surface active agent generally include less than about 12% by weight of total surface active agent (e.g., less than about 10%, less than about 8%, less than about 6%, less than about 4%, less than about 2%, or less than about 1%). In particular embodiments of the invention the total sum of all the surfactants is about 6%.

Methods of Making Pharmaceutical Compositions and the Compositions Produced:

Also included in the invention are methods of producing the compositions described herein. Thus one embodiment of the invention is a process for producing a pharmaceutical composition which comprises preparing a water-soluble composition comprising a therapeutically effective amount of at least one therapeutic agent and a medium chain fatty acid salt (as described above), drying the water soluble composition to obtain a solid powder, and suspending the solid powder in a hydrophobic medium, to produce a suspension containing in solid form the therapeutic agent and the medium chain fatty acid salt, thereby producing the pharmaceutical composition, wherein the pharmaceutical composition contains 10% or more by weight of medium chain fatty acid salt.

One embodiment is a process for producing a pharmaceutical composition which comprises providing a solid powder of a therapeutically effective amount of at least one therapeutic agent and a solid powder comprising a medium chain fatty acid salt, and suspending the solid powders in a hydrophobic medium, to produce a suspension containing in solid form the therapeutic agent and the medium chain fatty acid salt, thereby producing the pharmaceutical composition, wherein the pharmaceutical composition contains 10% or more by weight of medium chain fatty acid salt.

In one embodiment of the processes and compositions described herein, the water-soluble composition is an aqueous solution. In certain embodiments the drying of the water-soluble composition is achieved by lyophilization or by granulation. In the granulation process a binder may be added to the water soluble composition before drying. In certain embodiments the drying step removes sufficient water so that the water content in the pharmaceutical composition is lower than about 6% by weight, about 5% by weight, about 4% by weight, about 3% or about 2% or about 1% by weight. In certain embodiments of the processes and compositions described herein the drying step removes an amount of water so that the water content in the solid powder is lower than 6% or 5% or 4% or 3% or preferably lower than 2% by weight. The water content is normally low and the water may be adsorbed to the solid phase during lyophilization i.e. the water may be retained by intermolecular bonds. In certain embodiments the water soluble composition additionally comprises a stabilizer for example methyl cellulose. In preferred embodiments of the of the processes and compositions described herein the hydrophobic medium is castor oil or glyceryl tricaprylate or glyceryl tributyrate or a combination thereof and may additionally contain octanoic acid; in certain embodiments the hydrophobic medium comprises an aliphatic, olefinic, cyclic or aromatic compound, a mineral oil, a paraffin, a fatty acid such as octanoic acid, a monoglyceride, a diglyceride, a triglyceride, an ether or an ester, or a combination thereof. In certain embodiments of the processes and compositions described herein the triglyceride is a long chain triglyceride, a medium chain triglyceride preferably glyceryl tricaprylate or a short chain triglyceride preferably glyceryl tributyrate, and the long chain triglyceride is castor oil or coconut oil or a combination thereof. In certain embodiments of the processes and compositions described herein the hydrophobic medium comprises castor oil or glyceryl tricaprylate or glyceryl tributyrate or a combination or mixture thereof, and may additionally comprise octanoic acid. In certain embodiments of the processes and compositions described herein the hydrophobic medium comprises glyceryl tricaprylate or a low molecular weight ester for example ethyl isovalerate or butyl acetate. In certain embodiments of the processes and compositions described herein the main component by weight of the hydrophobic medium is castor oil and may additionally comprise glyceryl tricaprylate. In certain embodiments of the processes and compositions described herein the main component by weight of the hydrophobic medium is glyceryl tricaprylate and may additionally comprise castor oil.

A basic formulation is provided as an embodiment wherein the hydrophobic medium consists essentially of castor oil, glyceryl monooleate and glyceryl tributyrate; in a further embodiment of the basic formulation the hydrophilic fraction consists essentially of therapeutic agent, PVP-12 and sodium octanoate.

A particular formulation is provided as an embodiment wherein the hydrophobic medium consists essentially of glyceryl tricaprylate, castor oil, glyceryl monocaprylate, and Tween 80, and the hydrophilic fraction consists essentially of therapeutic agent (e.g. octreotide), PVP-12 and sodium octanoate. Another particular formulation is provided as an embodiment wherein the hydrophobic medium comprises glyceryl tricaprylate, castor oil, glyceryl monocaprylate, and Tween 80, and the hydrophilic fraction comprises therapeutic agent (e.g. octreotide), PVP-12 and sodium octanoate. In certain embodiments the hydrophobic medium consists essentially of glyceryl tricaprylate and in certain embodiments additionally contains castor oil and/or glyceryl monocaprylate.

In certain embodiments the composition comprises a suspension which consists essentially of an admixture of a hydrophobic medium and a solid form wherein the solid form comprises a therapeutically effective amount of a therapeutic agent and at least one salt of a medium chain fatty acid, and wherein the medium chain fatty acid salt is present in the composition at an amount of 10% or more by weight. In certain embodiments the hydrophobic medium consists essentially of castor oil, glyceryl monooleate and glyceryl tributyrate; or the hydrophobic medium consists essentially of glyceryl tricaprylate and glyceryl monocaprylate; or the hydrophobic medium consists essentially of castor oil, glyceryl tricaprylate and glyceryl monocaprylate. In certain embodiments the hydrophobic medium comprises a triglyceride and a monoglyceride and in certain particular embodiments the monoglyceride has the same fatty acid radical as the triglyceride. In certain of these embodiments the triglyceride is glyceryl tricaprylate and the monoglyceride is glyceryl monocaprylate. In certain embodiments the medium chain fatty acid salt in the water-soluble composition has the same fatty acid radical as the medium chain monoglyceride or as the medium chain triglyceride or a combination thereof. In certain of these embodiments the medium chain fatty acid salt is sodium caprylate (sodium octanoate) and the monoglyceride is glyceryl monocaprylate and the triglyceride is glyceryl tricaprylate.

Many of the compositions described herein comprise a suspension which comprises an admixture of a hydrophobic medium and a solid form wherein the solid form comprises a therapeutically effective amount of a therapeutic agent and at least one salt of a medium chain fatty acid, and wherein the medium chain fatty acid salt is present in the composition at an amount of 10% or more by weight. The solid form may be a particle (e.g., consist essentially of particles, or consists of particles). The particle may be produced by lyophilization or by granulation.

In a particular embodiment the formulation consists essentially of a suspension which comprises an admixture of a hydrophobic medium and a solid form wherein the solid form comprises a therapeutically effective amount of a therapeutic agent and about 10-20% preferably 15% medium chain fatty acid salt preferably sodium octanoate, and about 5-10% preferably 10% PVP-12; and wherein the hydrophobic medium comprises about 20-80%, preferably 30-70% triglyceride preferably glyceryl tricaprylate or glyceryl tributyrate or castor oil or a mixture thereof, about 3-10% surfactants, preferably about 6%, preferably glyceryl monocaprylate and Tween 80 and about 1% water; in particular embodiments the therapeutic agent is present at an amount of less than 33%, or less than 25%, or less than 10%, or less than 1% or less than 0.1%. The solid form may be a particle (e.g., consist essentially of particles, or consists of particles). The particle may be produced by lyophilization or by granulation. In a particular embodiment the solid form may be a particle and may be produced by lyophilization or by granulation.

In a further embodiment the formulation consists essentially of a suspension which comprises an admixture of a hydrophobic medium and a solid form wherein the solid form comprises a therapeutically effective amount of a therapeutic agent and about 10-20% preferably 15% medium chain fatty acid salt preferably sodium octanoate and about 5-10% preferably 10% PVP-12; and wherein the hydrophobic medium comprises about 20-80%, preferably 30-70% medium or short chain triglyceride preferably glyceryl tricaprylate or glyceryl tributyrate, about 0-50% preferably 0-30% castor oil, about 3-10% surfactants, preferably about 6%, preferably glyceryl monocaprylate and Tween 80, and about 1% water; in particular embodiments the therapeutic agent is present at an amount of less than 33%, or less than 25%, or less than 10%, or less than 1% or less than 0.1%.

In a particular embodiment the formulation consists essentially of a suspension which comprises an admixture of a hydrophobic medium and a solid form wherein the solid form comprises a therapeutically effective amount of a therapeutic agent and about 15% sodium octanoate and about 10% PVP-12; and wherein the hydrophobic medium comprises about 41% glyceryl tricaprylate, about 27% castor oil, about 4% glyceryl monocaprylate, about 2% Tween 80, about 1% water and 1% or less therapeutic agent; when the therapeutic agent is octreotide it is present at about 0.058%.

In another particular embodiment the formulation consists essentially a suspension which comprises an admixture of a hydrophobic medium and a solid form wherein the solid form comprises a therapeutically effective amount of a therapeutic agent and about 15% sodium octanoate and about 10% PVP-12; and wherein the hydrophobic medium comprises about 68% glyceryl tricaprylate, about 4% glyceryl monocaprylate, about 2% Tween 80, about 15% sodium octanoate, about 10% PVP-12, about 1% water and less than 1% therapeutic agent; when the therapeutic agent is octreotide it is present at about 0.058%.

One embodiment is a composition comprising a suspension which comprises an admixture of a hydrophobic medium and a solid form wherein the solid form comprises a therapeutically effective amount of octreotide and at least one salt of a medium chain fatty acid; in a further embodiment the medium chain fatty acid salt is present in the composition at an amount of 10% or more by weight, preferably 15% by weight; in a further embodiment the solid form additionally comprises a matrix-forming polymer. In a further embodiment the matrix forming polymer is dextran or polyvinylpyrrolidone (PVP). In a specific embodiment the matrix forming polymer is polyvinylpyrrolidone and the polyvinylpyrrolidone is present in the composition at an amount of about 2% to about 20% by weight, preferably about 10% by weight. In a specific embodiment the polyvinylpyrrolidone is PVP-12 and/or the polyvinylpyrrolidone has a molecular weight of about 3000. In specific embodiments the hydrophobic medium consists essentially of glyceryl tricaprylate and the solid form additionally consists of PVP-12 and sodium octanoate. In more specific embodiments the hydrophobic medium additionally consists of castor oil or glyceryl monocaprylate or a combination thereof and a surfactant. In further specific embodiments the hydrophobic medium consists of glyceryl tricaprylate, glyceryl monocaprylate, and polyoxyethylene sorbitan monooleate (Tween 80). In a further embodiment the solid form consists essentially of octreotide, PVP-12 and sodium octanoate. In a particular embodiment the composition contains about 41% of glyceryl tricaprylate, about 27% castor oil, about 4% glyceryl monocaprylate, about 2% Tween 80, about 15% sodium octanoate, about 10% PVP-12, about 1% water and about 0.058% octreotide. In another particular embodiment the composition contains about 68% of glyceryl tricaprylate, about 4% glyceryl monocaprylate, about 2% Tween 80, about 15% sodium octanoate, about 10% PVP-12, about 1% water and about 0.058% octreotide.

In all the above formulations, the percentages recited are weight/weight and the solid form may be a particle (e.g., consist essentially of particles, or consists of particles). The particles may be produced by lyophilization or by granulation.

Under normal storage conditions, the therapeutic agent within the formulations of the invention is stable over an extended period of time. The chemical and physical state of the formulation is stable. Once administered to the intestine the therapeutic agent is protected from damage by the GI environment since the formulations are oil-based and therefore a separate local environment is created in the intestine where the therapeutic agent is contained in oil droplets, which confers stability in vivo.

In certain embodiments the process produces a composition which consists essentially of a therapeutic agent and a medium chain fatty acid salt and a hydrophobic medium. In embodiments of the invention the solid powder (solid form) consists essentially of a therapeutic agent and a medium chain fatty acid salt. Further embodiments of the invention are pharmaceutical compositions produced by the process describe herein. In certain pharmaceutical compositions the therapeutic agent is a protein, a polypeptide, a peptide, a glycosaminoglycan, a polysaccharide, a small molecule or a polynucleotide and in particular embodiments the therapeutic agent is insulin, growth hormone, parathyroid hormone, teriparatide, interferon-alfa (IFN-α), a low molecular weight heparin, leuprolide, fondaparinux, octreotide, exenatide, terlipressin, vancomycin or gentamicin. Particular embodiments of the invention comprise an oral dosage form comprising the pharmaceutical composition, in particular an oral dosage form which is enteric coated. Further embodiments of the invention comprise a capsule containing the compositions of the invention, and in various embodiments the capsule is a hard gel or a soft gel capsule, and generally the capsule is enteric-coated. Other embodiments of the invention comprise a rectal dosage form comprising the pharmaceutical composition, in particular a suppository, or a buccal dosage form. A kit comprising instructions and the dosage form is also envisaged.

The therapeutic agent or medium chain fatty acid salt, or any combination of therapeutic agent and other components, such as protein stabilizers, can be prepared in a solution of a mixture (e.g., forming an aqueous solution or mixture) which can be lyophilized together and then suspended in a hydrophobic medium. Other components of the composition can also be optionally lyophilized or added during reconstitution of the solid materials.

In some embodiments, the therapeutic agent is solubilized in a mixture, for example, including one or more additional components such as a medium chain fatty acid salt, a stabilizer and/or a surface active agent, and the solvent is removed to provide a resulting solid powder (solid form), which is suspended in a hydrophobic medium. In some embodiments, the therapeutic agent and/or the medium chain fatty acid salt may be formed into a granulated particle that is then associated with the hydrophobic medium (for example suspended in the hydrophobic medium or coated with the hydrophobic medium). In general, the compositions described herein are substantially free of "membrane fluidizing agents" such as medium chain alcohols.

"Membrane fluidizing agents" are defined as medium chain alcohols which have a carbon chain length of from 4 to 15 carbon atoms (e.g., including 5 to 15, 5 to 12, 6, 7, 8, 9, 10, or 11 carbon atoms). For example, a membrane fluidizing agent can be a linear (e.g., saturated or unsaturated), branched (e.g., saturated or unsaturated), cyclical (e.g., saturated or unsaturated), or aromatic alcohol. Examples of suitable linear alcohols include, but are not limited to, butanol, pentanol, hexanol, heptanol, octanol, nonanol, decanol, undecanol, dodecanol, tridecanol, tetradecanol, and pentadecanol. Examples of branched alcohols include, but are not limited to, geraniol, farnesol, rhodinol, citronellol. An example of a cyclical alcohol includes, but is not limited to, menthol, terpineol, myrtenol, perillyl and alcohol. Examples of suitable aromatic alcohols include, but are not limited to, benzyl alcohol, 4-hydroxycinnamic acid, thymol, styrene glycol, and phenolic compounds. Examples of phenolic compounds include, but are not limited to, phenol, m-cresol, and m-chlorocresol.

If desired, the pharmaceutical composition may also contain minor amounts of non-toxic auxiliary substances such pH buffering agents, and other substances such as for example, sodium acetate and triethanolamine oleate.

In at least one embodiment, a therapeutic agent, such as a protein, may be chemically modified to enhance its half-life in circulation. For example, the therapeutic agent may undergo a process such as pegylation.

In some embodiments the process for producing a pharmaceutical composition comprises preparing a water-soluble composition comprising a therapeutically effective amount of at least one therapeutic agent and a medium chain fatty acid salt, drying the water soluble composition to obtain a solid powder, and dissolving the solid powder in a solution consisting essentially of octanoic acid, thereby producing the pharmaceutical composition, which is a solution. In some embodiments, the solid form may be a particle (e.g., consist essentially of particles, or consists of particles). In some embodiments, the particle may be produced by lyophilization or by granulation. In some embodiments of this process the octanoic acid is present in the composition at a level of about 60% to about 90% or at a level of about 70 to about 85% preferably about 78%. In some embodiments of this process the fatty acid salt is sodium octanoate; in further embodiments of this process the medium chain fatty acid salt is present in the composition at an amount of about 11% to about 40% by weight or at an amount of about 11% to about 28% by weight or at an amount of about 15% by weight. In some embodiments of this process the composition additionally comprises a matrix forming polymer and in particular embodiments of this process the matrix forming polymer is dextran or polyvinylpyrrolidone (PVP); in further embodiments of this process the polyvinylpyrrolidone is present in the composition at an amount of about 2% to about 20% by weight or at an amount of about 5% to about 15% by weight, preferably at an amount of about 10% by weight. In certain embodiments of this process the polyvinylpyrrolidone is PVP-12 and/or has a molecular weight of about 3000. The composition may in addition include surfactants as described above. The pharmaceutical products of these processes are further embodiments of the invention e.g. a composition containing octanoic acid at a level of about 60% to about 90% or at a level of about 70 to about 85% preferably about 78%; fatty acid salt, preferably sodium octanoate, present in the composition at an amount of about 11% to about 40% by weight or at an amount of about 11% to about 28% by weight or at an amount of about 15% by weight; matrix forming polymer e.g. polyvinylpyrrolidone, preferably PVP-12, present in the composition at an amount of about 2% to about 20% by weight or preferably an amount of about 5% to about 15% by weight, preferably at an amount of about 10% by weight; and surfactants as described above. There also may be small quantities of other hydrophobic constituents as described above.

Capsules:

Preferred pharmaceutical compositions are oral dosage forms or suppositories. Exemplary dosage forms include gelatin or vegetarian capsules like starch hydroxylpropyl-methylcellulose ("HPMC") capsules, enteric coated, containing the bulk drug product. Capsules which may be used to encapsulate the compositions of this invention are known in the art and are described for example in *Pharmaceutical Capsules* edited by Podczech and Jones, Pharmaceutical Press (2004) and in *Hard gelatin capsules today—and tomorrow,* 2nd edition, Steggeman ed published by Capsugel Library (2002).

Additional Formulations:

The compositions of the invention may be formulated using additional methods known in the art, for example as described in the following publications: *Pharmaceutical Dosage Forms* Vols 1-3 ed. Lieberman, Lachman and Schwartz, published by Marcel Dekker Inc, New York (1989); *Water-insoluble Drug Formulation* $2^{nd}$ edition, Liu, editor, published by CRC Press, Taylor and Francis Group (2008); *Therapeutic Peptides and Proteins: Formulation, Processing and Delivery Systems,* $2^{nd}$ edition by Ajay K. Banga (author) published by CRC Press, Taylor and Francis Group (2006); *Protein Formulation and Delivery,* $2^{nd}$ edition, McNally and Hasted eds, published by Informa Healthcare USA Inc(2008); and *Advanced Drug Formulation to Optimize Therapeutic Outcomes,* Williams et al eds, published by Informa Healthcare USA (2008).

The compositions of the invention may be formulated using microparticulate technology for example as described in *Microparticulate Oral Drug Delivery*, Gerbre-Selassie ed., published by Marcel Dekker Inc (1994) and in Dey et al, *Multiparticulate Drug Delivery Systems for Controlled Release*, Tropical Journal of Pharmaceutical Research, September 2008; 7 (3): 1067-1075.

Methods of Treatment:

The compositions described herein exhibit effective, enteral delivery of an unaltered biologically active substance (i.e. a therapeutic agent) and thus, have many uses. For example, the compositions described herein can be used in the treatment of diabetes.

In particular, insulin to treat and prevent subjects (patients) suffering from Type II diabetes (prophylaxis of diabetes), and to treat patients suffering from dysglycemia, pre-diabetes and metabolic syndrome and other conditions, may be administered in accordance with one or more embodiments of the invention. Metabolic syndrome is a combination of medical disorders that increase the risk of developing cardiovascular disease and diabetes. Metabolic syndrome is a composite of different symptoms: (1) fasting hyperglycemia (insulin resistance, type II diabetes, etc); (2) decreased HDL cholesterol; (3) elevated triglycerides; (4) high blood pressure; (5) central obesity; and (6) proinflammatory state.

One embodiment of the invention is a method of treatment or prevention of a subject suffering from the above conditions where the amount of insulin sufficient to treat the condition is a low dose of insulin formulated within the compositions of the invention. Low dose insulin is provided by less than 300 or less than 200 Units per capsule e.g. 40-200 Units per capsule.

Terlipressin (or other vasopressin analogs) to treat subjects (patients) suffering from hepato-renal syndrome (HRS), including HRS I and II, bleeding esophageal varices, portal hypertension and other conditions may be administered in accordance with one or more embodiments of the invention. Such terlipressin formulations may also be used for primary and secondary prophylaxis of variceal bleeding. A composition of the invention comprises a suspension which comprises an admixture of a hydrophobic medium and a solid form wherein the solid form comprises a therapeutically effective amount of terlipressin (or other vasopressin analogues) and at least one salt of a medium chain fatty acid.

Exenatide to improve glycemic control in subjects suffering from Type II diabetes and to treat other conditions such as obesity and for use in weight management may be administered in accordance with one or more embodiments of the invention.

Interferon-alfa for the treatment of subjects suffering from chronic hepatitis C and chronic hepatitis B and to treat other conditions including cancer may be administered in accordance with one or more embodiments of the invention.

Copaxone to treat subjects suffering from multiple sclerosis and to treat other conditions including inflammatory diseases may be administered in accordance with one or more embodiments of the invention.

Desmopressin to treat subjects suffering from primary nocturnal enuresis, central diabetes insipidus (DI) or bleeding disorders (Von Willebrand Disease and Hemopilia A) may be administered in accordance with one or more embodiments of the invention. Oral desmopressin preparations known in the art suffer from extremely low oral bioavailability.

Octreotide was first synthesized in 1979, and is an octapeptide that mimics natural somatostatin pharmacologically, though it is a more potent inhibitor of growth hormone, glucagon and insulin than the natural hormone. Octreotide or other analogs of somatostatin may be administered in accordance with one or more embodiments of the invention for use in treating or preventing a disease or disorder in a subject suffering from a disorder such as acromegaly, abnormal GI motility, flushing episodes associated with carcinoid syndrome, portal hypertension, an endocrine tumor (such as carcinoids, VIPoma), gastroparesis, diarrhea, pancreatic leak or a pancreatic pseudo-cyst. The diarrhea may result from radiotherapy or may occur for example in subjects with vasoactive intestinal peptide-secreting tumors (VIPomas). In addition, patients that undergo pancreatic surgery may suffer from secretion of extrinsic pancreas and are vulnerable to developing pancreatic leak or pseudo-cysts which may be treated by octreotide products of the invention. Some preferred embodiments are directed to a method of treating a subject having a disorder such as acromegaly, abnormal GI motility, flushing episodes associated with carcinoid syndrome, portal hypertension, an endocrine tumor (such as carcinoids, VIPoma), gastroparesis, diarrhea, pancreatic leak or a pancreatic pseudo-cyst, which comprises administering to the subject a composition of the invention, wherein the therapeutic agent is octreotide, in an amount sufficient to treat the disorder. Octreotide formulations of the invention may also be used for primary and secondary prophylaxis of variceal bleeding, which may be caused by portal hypertension; the varices may be gastric or esophageal. Other uses of octreotide formulations of the invention are in treatment of shock of hypovolemic (e.g. hemorrhagic) or vasodilatory (e.g. septic) origin, hepatorenal syndrome (HRS), cardiopulmonary resuscitation and anesthesia-induced hypotension. Other analogs of somatostatin may be used in the methods and compositions in which octreotide is used.

Vancomycin (molecular weight 1449 Da) is a glycopeptide antibiotic used in the prophylaxis and treatment of infections caused by Gram-positive bacteria. The original indication for vancomycin was for the treatment of methycilin-resistant *Staphylococcus aureus* (MRSA). Vancomycin never became first line treatment for *Staphylococcus aureus*, one reason being that vancomycin must be given intravenously. The prior art preparations of vancomycin need to be given intravenously for systemic therapy, since vancomycin does not cross through the intestinal lining. It is a large hydrophilic molecule which partitions poorly across the gastrointestinal mucosa. The only indication for oral vancomycin therapy is in the treatment of pseudomembranous colitis where it must be given orally to reach the site of infection in the colon. Vancomycin for use in treating or preventing infection in a subject may be administered orally to the subject in accordance with one or more embodiments of the invention. Some preferred embodiments of the invention are directed to a method of treating or preventing an infection in a subject which comprises administering to the subject a composition of the invention, wherein the therapeutic agent is vancomycin, in an amount sufficient to treat or prevent the infection.

Gentamicin (molecular weight=478) is an aminoglycoside antibiotic, used to treat many types of bacterial infections, particularly those caused by gram-negative bacteria. When gentamicin is given orally in the prior art formulations, it is not systemically active. This is because it is not absorbed to any appreciable extent from the small intestine.

In addition, compositions of the invention also can be used to treat conditions resulting from atherosclerosis and the formation of thrombi and emboli such as myocardial infarction and cerebrovascular accidents. Specifically, the compositions can be used to deliver heparin or low molecular weight heparin or fondaparinux across the mucosal epithelia.

The compositions of this invention can also be used to treat hematological diseases and deficiency states such as anemia and hypoxia that are amenable to administration of hematological growth factors. The compositions of the invention can be used to deliver vitamin B12 in a subject at high bioavailability wherein the mucosal epithelia of the subject lacks sufficient intrinsic factor. G-CSF may also be administered in accordance with various embodiments. Additionally, the compositions of this invention can be used to treat osteoporosis, such as through enteral administration of PTH, teriparatide or calcitonin once or twice or more daily.

Human growth hormone (hGH) to treat growth hormone deficiency in particular in children may be administered in accordance with one or more embodiments. In some preferred embodiments, a composition described herein comprising growth hormone can be administered to a subject to treat or prevent metabolic and lipid-related disorders, e.g., obesity, abdominal obesity, hyperlipidemia or hypercholestrolemia. For example a composition of the invention comprising growth hormone can be administered orally to a subject thereby treating obesity (e.g., abdominal obesity). In some preferred embodiments, a composition described herein comprising growth hormone is administered to a subject to treat or prevent HIV lipodystrophy (AIDS wasting) or to treat Prader-Willi syndrome, growth disturbance due to insufficient secretion of growth hormone (e.g. associated with gonadal dysgenesis or Turner syndrome), growth disturbance in prepubertal children with chronic renal insufficiency, and as replacement therapy in adults with pronounced growth hormone deficiency. Compositions of the invention comprising growth hormone can be administered orally to a subject to promote wound healing and attenuate catabolic responses in severe burns, sepsis, multiple trauma, major operations, acute pancreatitis and intestinal fistula. Many other conditions besides GH deficiency cause poor growth, but growth benefits (height gains) are often poorer than when GH deficiency is treated. Examples of other causes of shortness which may be treated with compositions of the invention comprising growth hormone are intrauterine growth retardation, and severe idiopathic short stature. Other potential uses of compositions of the invention comprising growth hormone include treatment to reverse or prevent effects of aging in older adults, to aid muscle-building and as treatment for fibromyalgia.

Some preferred embodiments are directed to a method of treating a disorder such as obesity, HIV lipodystrophy, metabolic disorder, or growth deficiency in a subject which comprises administering to the subject a composition of the invention wherein the therapeutic agent (the effector) is growth hormone, in an amount sufficient to treat the disorder.

Some preferred embodiments are directed to a method of treating a bone disorder in a subject which comprises administering to the subject a composition of the invention, wherein the therapeutic agent is teriparatide or parathyroid hormone, in an amount sufficient to treat the bone disorder.

Some preferred embodiments are directed to a method of treating or preventing a blood coagulative disorder in a subject which comprises administering to the subject a composition of the invention wherein the therapeutic agent is heparin or a heparin derivative or fondaparinux, in an amount sufficient to treat or prevent the blood coagulative disorder.

Leuprolide (GnRH agonist) formulated in an embodiment of the invention may be delivered for treatment of female infertility (e.g. once or twice daily dosage), prostate cancer and Alzheimer's disease.

One embodiment of the invention relates to a method of treating a subject suffering from a disease or disorder which comprises administering to the subject a composition of the invention in an amount sufficient to treat the condition. Another embodiment of the invention relates to compositions of the invention for use in treating a disease or disorder in a subject. Another embodiment of the invention relates to the use of a therapeutic agent in the manufacture of a medicament by the process of the invention for the treatment of a disorder.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition. Oral dosages of the present invention, when used for the indicated effects, may be provided in the form of capsules containing 0.001, 0.0025, 0.005, 0.01, 0.025, 0.05, 0.1, 0.25, 0.5, 1.0, 2.5, 5.0, 10.0, 15.0, 25.0, 50.0 or 100, 200, 300, 400, 500, 600, 700, 800 or 1000 mg of therapeutic agent.

Compounds of the present invention may be administered in a single daily dose, or the total daily dosage may be administered in divided doses of two, three, four, five or six times daily. In some embodiments, the composition is administered at a daily dose of from about 0.01 to about 5000 mg/day, e.g., administered once daily (e.g., in the morning or before bedtime) or twice or more daily (e.g. in the morning and before bedtime).

A representative product of the invention is an API-based formulation orally administered as enteric coated-capsules: each capsule contains API co-lyophilized with PVP-12 and sodium octanoate, and suspended in a hydrophobic (lipophilic) medium containing: glyceryl tricaprylate, glyceryl monocaprylate, and Tween 80; in another representative product of the invention castor oil is additionally present. The compositions described herein can be administered to a subject i.e. a human or an animal, in order to treat the subject with a pharmacologically or therapeutically effective amount of a therapeutic agent described herein. The animal may be a mammal e.g. a mouse, rat, pig horse, cow or sheep. As used herein the term "pharmacologically or therapeutically effective amount" means that amount of a drug or pharmaceutical agent (the therapeutic agent) that will elicit the biological or medical response of a tissue, system, animal or human that is being sought by a researcher or clinician.

The formulations of the invention allow incorporation of the therapeutic agent into the formulation without any chemical modification of the therapeutic agent. Additionally, as shown above, many different therapeutic agents have been successfully formulated within the formulations of the invention, including polypeptides, nucleotides, small molecules and even medium size proteins. Furthermore, the formulations of the invention allow for high flexibility in loading of the therapeutic agent. Loading capacity is dependent on the therapeutic agent. To date, loading capacity limits have not been reached; however loading of up to 1.5% wt/wt (polypeptides) and 6% wt/wt (small molecules) has been achieved and higher loading up to 33% is envisaged. Finally, the formulations of the invention protect the cargo compounds from inactivation in the GI environment due to for example proteolytic degradation and oxidation.

The function and advantages of these and other embodiments will be more fully understood from the following examples. These examples are intended to be illustrative in nature and are not to be considered as limiting the scope of the systems and methods discussed herein.

EXAMPLES

Example 1

Formulations

A. Composition of an Insulin Formulation

Table 1A presents an example of a composition in accordance with one or more embodiments. More specifically, this composition is an insulin formulation. Insulin was obtained from Diosynth Biotechnology; sodium octanoate and NaOH from Merck; MgCl$_2$, MC400, Span40, lecithin and castor oil from Spectrum; PVP-12 from BASF; ethyl isovalerate from Merck/Sigma; glyceryl tributyrate from Acros/Penta; and glycerol monooleate from Abitec Corp.

TABLE 1A

|  | Ingredient | % w/w |
|---|---|---|
| Hydrophilic Fraction | Insulin | 0.417 |
|  | NaOH | 0.029 |
|  | MgCl$_2$ | 0.104 |
|  | PVP-12 | 2.083 |
|  | Sodium octanoate | 3.125 |
|  | Methyl cellulose | 0.104 |
| Hydrophobic Medium | Castor oil | 52.858 |
|  | Glyceryl tributyrate | 28.466 |
|  | Ethyl isovalerate | 8.195 |
|  | Glycerol monooleate | 1.779 |
|  | Lecithin | 1.893 |
|  | Span-40 | 0.946 |

B. A Formulation for Leuprolide:

Table 1B presents an example of a composition for an API (Active Pharmaceutical Ingredient) in accordance with one or more embodiments. More specifically, this composition is a leuprolide formulation.

TABLE 1B

|  | Ingredient | % w/w |
|---|---|---|
| Hydrophilic Fraction | Leuprolide | 0.072 |
|  | NaOH | 0.038 |
|  | MgCl$_2$ | 0.137 |

TABLE 1B-continued

| | Ingredient | % w/w |
|---|---|---|
| | PVP-12 | 2.740 |
| | Sodium octanoate | 12.002 |
| | Methyl cellulose | 0.137 |
| | Water | 0.605 |
| Hydrophobic Medium | Span-40 | 1.21 |
| | Lecithin | 2.43 |
| | Ethyl-isovalerate | 10.52 |
| | Glycerol monooleate | 2.28 |
| | Glyceryl tributyrate | 23.74 |
| | Castor Oil | 44.09 |

C. A Formulation with Decreased Amount of Hydrophobic Medium (50% of Hydrophobic Medium)

Table 1C presents an example of a composition for an API in accordance with one or more embodiments. More specifically, this composition is a formulation for dextran (FD4). The FD4 is FITC-labeled dextran with a MW of 4.4 kDa (Sigma, FD4) and this is the dextran which was used throughout the Examples unless stated otherwise. This particular formulation contains coconut oil (Sigma) instead of GTB.

TABLE 1C

| | Ingredient | % w/w |
|---|---|---|
| Hydrophilic Fraction | Dextran | 0.939 |
| | NaOH | 0.001 |
| | $MgCl_2$ | 0.235 |
| | PVP-12 | 4.693 |
| | Sodium octanoate | 20.662 |
| | Methyl cellulose | 0.235 |
| | Water | 1.071 |
| Hydrophobic Medium | Span-40 | 1.04 |
| | Lecithin | 2.08 |
| | Ethyl-isovalerate | 9.01 |
| | Glycerol-monooleate | 1.95 |
| | Coconut oil | 20.33 |
| | Castor oil | 37.75 |

The above formulations are used for a wide variety of therapeutic agents and give good bioavailability to the cargo compound in the animal models described below. Note that the net amount of therapeutic agent may vary as appropriate in any of the formulations and there may be minor variations in the formulations; for example NaOH is not always used; coconut oil may be used instead of glyceryl tributyrate; $MgCl_2$ is not always used (e.g. with hGH it is not used); all ingredients may be substituted as described above in the specification.

Example 2

Schematic Representation of Insulin Formulation Production

FIG. 1 illustrates a method of producing a composition in accordance with one or more embodiments. For example, this method may be implemented to make the compositions presented above in Example 1.

Example 3

Figure 2:
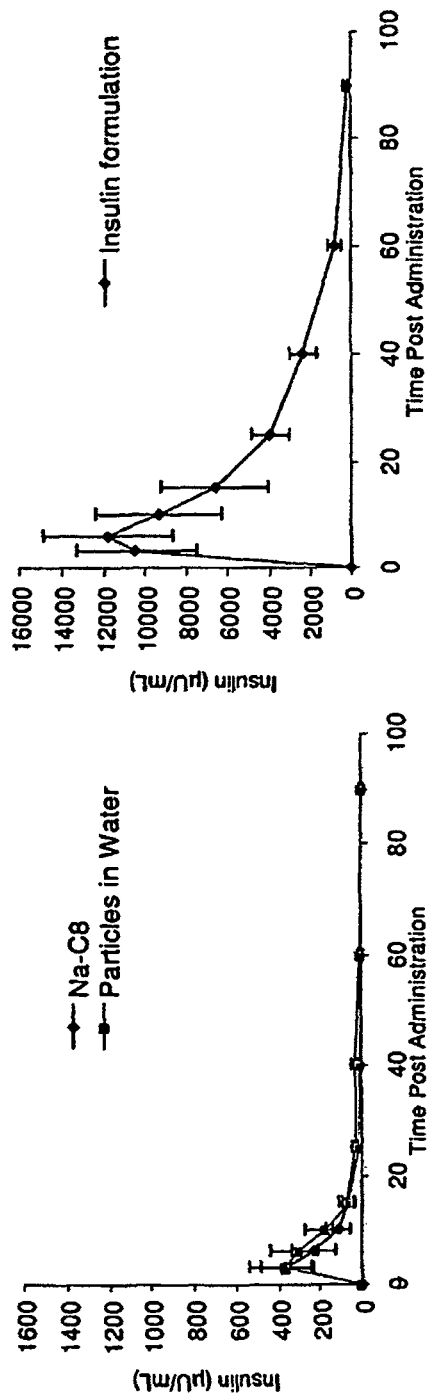
FIGS. 2-5 present data referenced in accompanying Examples 3 through 6.

The Combination of Solid Particles Containing Sodium Octanoate and Hydrophobic Medium is Critical for Permeation Activity FIG. 2 presents data relating to serum insulin levels after rectal administration to rats. Rats were anesthetized and were administered 100 μL of bulk drug formulation containing an insulin dose of 328 μg/rat (9 IU/rat). Blood samples were collected at 0, 3, 6, 10, 15, 25, 30, 40, 60 and 90 minutes post administration and serum was prepared for determination of human insulin by an immunoassay kit with no cross reactivity between rat and human insulin.

Data is presented as MEAN±SD, n=5. The left panel of FIG. 2 relates to administration of human insulin with sodium octanoate (Na—C8) or solid hydrophilic fraction suspended in water (solid particles in water). The right panel of FIG. 2 relates to administration of full insulin formulation (solid particles in hydrophobic medium). Table 2 below presents a summary of AUC values calculated from the concentration vs. time curves.

TABLE 2

| Test compound | $AUC_{(0-\infty)}$ |
|---|---|
| Na—C8 | 5753 ± 3569 |
| Solid particles in water | 4083 ± 2569 |
| Insulin in formulation (Solid particles in hydrophobic medium) | 280933 ± 78692 |

Data are MEAN ± SD

The average exposure (expressed by AUC values) to insulin after rectal administration of insulin-SCD was about 50-fold higher than the exposure after administration without a hydrophobic medium. Minimal exposure was detected in rats administered insulin with sodium octanoate alone or as part of the solid particles of the hydrophilic fraction (as listed in Example 1) suspended in water. These data demonstrate synergy between solid sodium octanoate and a hydrophobic medium.

Example 4

Intestinal Absorption of Insulin after GI Administration of Insulin to Rats

Figure 3:
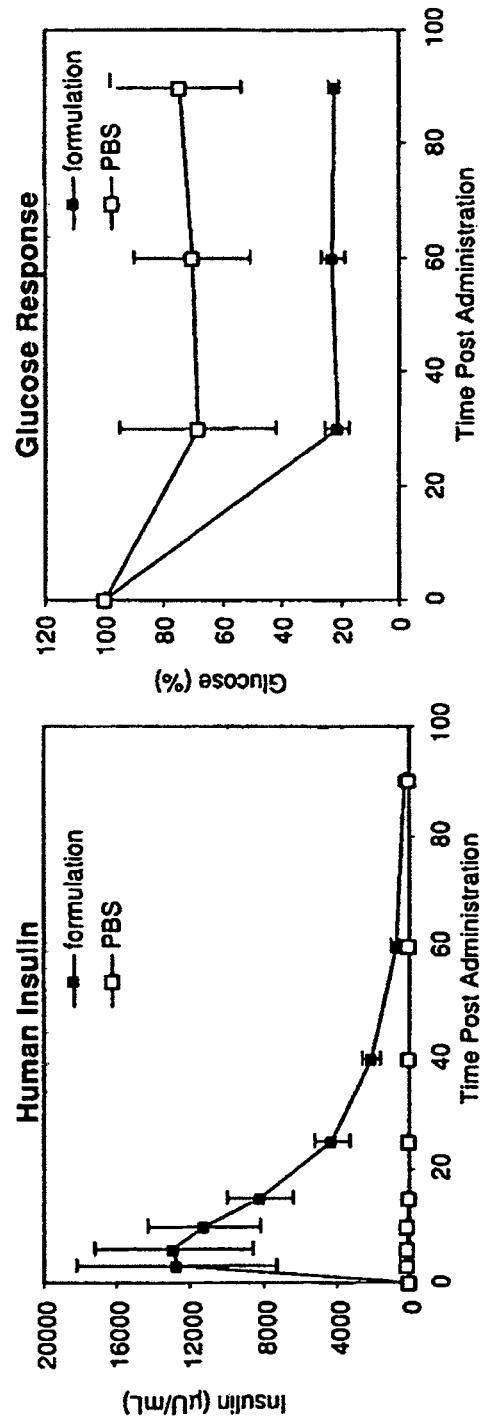

FIG. 3 presents data relating to serum insulin levels and blood glucose levels after rectal administration of insulin solution and insulin in formulation to rats. Rats were anesthetized and administered 100 μL of test article (insulin in formulation or insulin in PBS) containing an insulin dose of 328 μg/rat (9 IU/rat). Blood samples were collected at 0, 3, 6, 10, 15, 25, 30, 40, 60 and 90 minutes post administration. Glucose level was immediately determined with a glucometer and serum was prepared for determination of human insulin by an immunoassay kit with no cross reactivity between rat and human insulin.

Glucose levels are presented as the percentage form basal levels measured before administration (time 0). The data of FIG. 3 is presented as MEAN±SD, n=5.

Levels of insulin (left panel on FIG. 3) and glucose (right panel of FIG. 3) after rectal administration of human insulin solubilized in PBS (insulin solution) or incorporated in the formulation are presented. Insulin levels rose rapidly in rat serum after rectal administration of insulin in formulation. Maximal levels were measured within 6 minutes post administration and a gradual drop detected until reaching basal levels at about 90 min post administration. This sharp and significant rise in insulin was accompanied by a significant drop in glucose levels reaching an average of 20% of the initial levels already at 30 min post administration. By contrast, rectal administration of insulin in PBS caused only a very slight glucose reduction, which is identical to that observed following treatment with the PBS control alone.

Example 5

Figure 4:
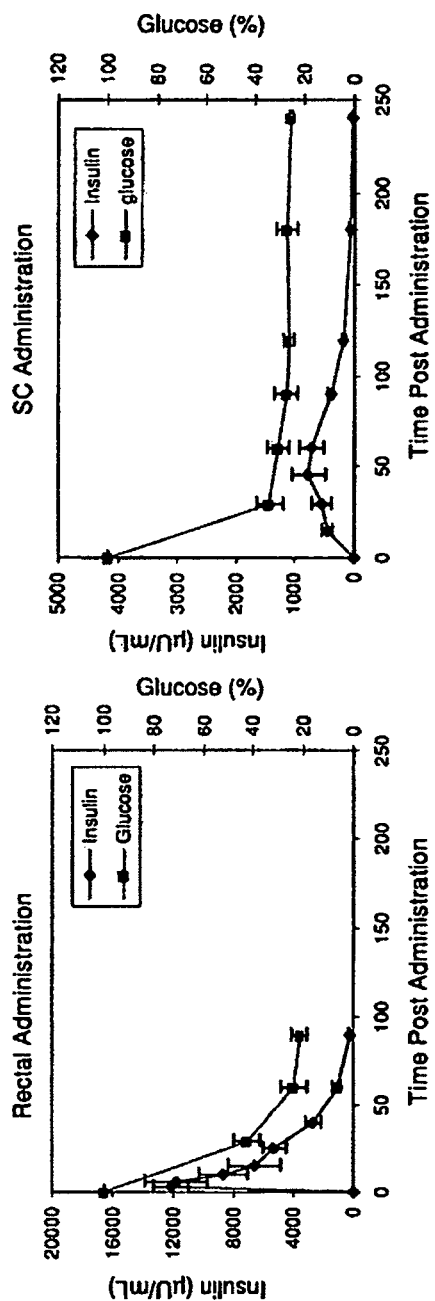

Insulin Absorption after Rectal Administration of Insulin in Formulation to Rats FIG. 4 presents data relating to changes in blood glucose and serum insulin concentrations following SC (subcutaneous) administration of insulin solution (at 20 μg/rat) and rectal administration of insulin in formulation (at 328 μg/rat). Blood samples were collected at 0, 3, 6, 10, 15, 25, 30, 40, 60 and 90 minutes post rectal administration and at 0, 15, 30, 45, 60, 90 min, 2, 3, and 4 hours post SC administration. Glucose was immediately determined with a glucometer and insulin by an immunoassay kit. Glucose levels are presented as the percentage form basal levels measured before administration (time 0). The data of FIG. 4 is presented as MEAN±SD, n=5.

The levels of insulin absorption from rat colon after insulin in formulation administration were compared to the levels of insulin absorbed after SC administration. Insulin exposure was calculated from the area under the serum concentration versus time curve (AUC) and the activity calculated as the relative bioavailability (rBA) according to the following equation:

$$rBA = (rectal\ AUC_{(0-\infty)}/SC\ AUC_{(0-\infty)})*(SC\ dose/rectal\ dose)$$

Insulin penetration into the bloodstream occurs during a narrow window of time, generally within about 10 minutes of rectal insulin in formulation administration. The rise in serum insulin is paralleled by a fall in blood glucose levels.

In order to derive information about insulin bioavailability when formulated insulin is presented into the colon, $AUC_{(0-\infty)}$ was determined for rectal and SC administration and the rBA value of human insulin was 29.4±3.4% with coefficient of variance (CV)=11.4%.

Rectal administration of various insulin-containing formulations was carried out on hundreds of animals. The assay was further developed and qualified as a bioassay to support platform development and batch release tests with a linear range of 10-200 μg/rat, repeatability of 39% and intermediate precision of 33%.

The insulin formulation described herein was tested in five different studies using a total of 25 rats. The rBA was 34.1±12.6% with CV of 28.9%.

Example 6

Insulin Absorption after Intra-Jejunal Administration of Insulin in Formulation to Rats The absorption target site of the orally administered platform of the invention is generally the small intestine. To test the activity of insulin formulation in rat intestine, two major obstacles were addressed: 1. Enteric-coated capsules for rats are not available and therefore stomach bypass enabling direct intra-jejunal administration is needed. 2. Insulin is extensively metabolized by the liver; in humans 50-80% of endogenous insulin, secreted by pancreatic β-cells, is sequestered by the liver and therefore can not be detected in the systemic circulation. Insulin administered via the intestinal route (by way of insulin formulation) mimics the endogenous route of insulin as the intestinal blood flow is drained into the portal vein which leads directly to the liver. Therefore to determine insulin absorbance, blood samples must be drawn from the portal vein (portal circulation, prior to the liver) as well as the jugular vein (systemic circulation, after the liver).

Figure 5:
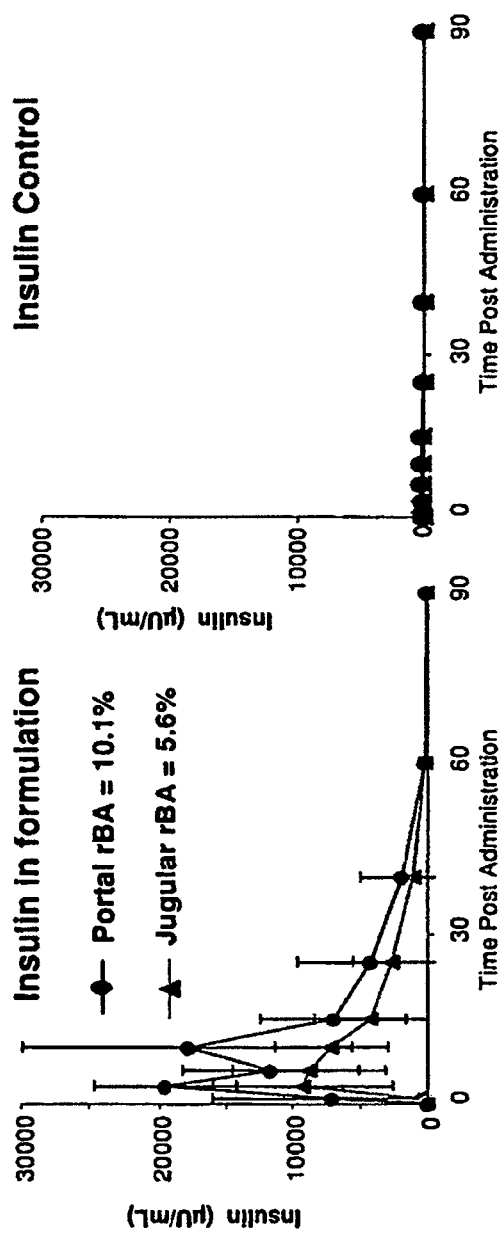

A specialized rat model in which three different cannulas are surgically implanted in anesthetized rats was developed: 1. Jejunal cannula—stomach bypass, enables insulin formulation administration, 2. Portal vein cannula—blood sampling prior to the liver, determine insulin that cross the GI wall into the blood, and 3. Jugular vein cannula—to determine the systemic levels of insulin. Using this model, the bioavailability of insulin in formulation (rBA) was determined FIG. 5 presents data from a representative study relating to insulin levels in the portal and systemic circulations after intra-jejunal administration of insulin control and insulin formulation to rats. Rats (8 rats per group) were anesthetized and their jejunum exposed by abdominal surgery. The jejunum containing intestinal loop was placed on gauze and kept moist and fully intact throughout the entire study. A temporary cannula was inserted into the jejunum and formulated insulin was administered. Blood was collected from both portal and jugular veins at the same time points, with approximately 4 time points per rat. The MEAN±SD value of each time point was used to create a plasma concentration vs. time curve. AUC was determined and rBA was calculated.

Insulin levels in both the portal and systemic circulation rose dramatically after intra-jejunum administration of insulin in formulation. This is in contrast to the minimal insulin absorbance detected when insulin control was administered. The window of absorption was short and insulin levels peaked by 6 minutes. This profile is similar to that seen after rectal administration of formulated insulin (see above). Higher insulin levels were detected in the portal compared to the systemic circulation, with rBA of 10.1% compared to 5.6%, respectively.

Example 7

Additional Formulations Comprising Various Cargo Compounds

Table 3A details the components of a range of dextran formulations which were prepared as described in the following Examples. The sodium caprate was obtained from Fluka/Sigma, the olive oil from Fluka, the octanoic acid from Sigma and the mineral oil from Acros.

TABLE 3A

| | | Cargo Dextran Formulation | | | | | | | |
|---|---|---|---|---|---|---|---|---|---|
| | Ingredient | A (% w/w) | B (% w/w) | C (% w/w) | D (% w/w) | E (% w/w) | F (% w/w) | G (% w/w) | H (% w/w) |
| Hydrophilic fraction | Cargo | 0.545 | 0.939 | 0.565 | 0.546 | 0.565 | 0.565 | 0.565 | 0.551 |
| | NaOH | 0.001 | 0.001 | 0.001 | 0.001 | 0.001 | 0.001 | 0.001 | 0.001 |
| | MgCl$_2$ | 0.136 | 0.235 | 0.141 | 0.156 | 0.141 | 0.141 | 0.141 | 0.138 |
| | PVP-12 | 2.726 | 4.693 | 2.823 | 3.117 | 2.823 | 2.823 | 2.823 | 2.754 |
| | Sodium octanoate | 12.001 | 20.662 | — | — | 9.002 | 9.002 | 9.002 | 12.125 |
| | Sodium caprate | — | — | 9.002 | — | — | — | — | — |
| | MC 400 | 0.136 | 0.235 | 0.141 | 0.156 | 0.141 | 0.141 | 0.141 | 0.138 |
| | Water | 0.622 | 1.071 | 0.507 | 0.159 | 0.507 | 0.507 | 0.507 | 0.661 |
| Hydrophobic medium | Span40 | 1.21 | 1.04 | 1.25 | 1.38 | 1.25 | 1.25 | 1.25 | — |
| | Lecithin | 2.42 | 2.08 | 2.50 | 2.76 | 2.50 | 2.50 | 2.50 | — |
| | Ethylisovalerate | 10.46 | 9.01 | 10.83 | 11.96 | 10.83 | 10.83 | 10.83 | 11.23 |
| | Glyceryl monooleate | 2.27 | 1.95 | 2.35 | 2.60 | 2.35 | 2.35 | 2.35 | — |
| | Glyceryl tributyrate | 23.62 | 20.33 | 24.46 | 24.29 | 24.46 | 24.46 | 24.46 | 25.35 |
| | Coconut oil | — | — | — | — | — | — | — | — |
| | Castor oil | 43.86 | 37.75 | 45.42 | 45.07 | 45.42 | — | — | 47.08 |
| | Octanoic acid | — | — | — | 7.80 | — | — | — | — |
| | Mineral oil | — | — | — | — | — | 45.42 | — | — |
| | Olive oil | — | — | — | — | — | — | 45.42 | — |

Table 3B details the components of a range of teriparatide acetate and leuprolide formulations which were prepared as described in the following Examples. Teriparatide was obtained from Novetide, and leuprolide was obtained from Bambio.

TABLE 3B

| | | Cargo | | | |
|---|---|---|---|---|---|
| | | Teriparatide | | Leuprolide | |
| | | Formulation | | | |
| | Ingredient | I (% w/w) | J (% w/w) | K (% w/w) | L (% w/w) |
| Hydrophilic fraction | Cargo | 0.118 | 0.118 | 0.050 | 0.050 |
| | NaOH | — | — | 0.040 | 0.04 |
| | MgCl$_2$ | 0.137 | 0.137 | 0.142 | 0.15 |
| | PVP-12 | 2.740 | 2.740 | 2.838 | 2.99 |
| | Sodium octanoate | 12.001 | 12.001 | 9.012 | — |
| | Sodium caprate | — | — | — | 4.48 |
| | MC 400 | 0.137 | 0.137 | 0.142 | 0.15 |
| | Water | 0.605 | 0.605 | 0.489 | 0.33 |
| Hydrophobic medium | Span40 | 1.214 | 1.214 | 1.26 | 1.32 |
| | Lecithin | 2.428 | 2.428 | 2.52 | 2.65 |
| | Ethyl-iso-valerate | 10.515 | 10.515 | 10.89 | 11.46 |
| | Glyceryl monooleate | 2.283 | 2.283 | 2.36 | 2.49 |
| | Glyceryl tributyrate | 23.740 | — | 24.59 | 25.87 |
| | Coconut oil | — | 23.740 | — | — |
| | Castor oil | 44.082 | 44.082 | 45.66 | 48.04 |

Table 3C details the components of hGH formulations which were prepared as described and the following Examples. The hGH was obtained from PLR, Israel (GHP-24).

TABLE 3C

| | | Cargo hGH Formulation | |
|---|---|---|---|
| | Ingredient | O (% w/w) | P (% w/w) |
| Hydrophilic fraction | Cargo | 0.298 | 0.303 |
| | NaOH | — | — |
| | MgCl$_2$ | — | — |
| | PVP-12 | 2.836 | 2.738 |
| | Sodium octanoate | 9.006 | 12.007 |
| | Sodium caprate | — | — |
| | MC 400 | 0.142 | 0.137 |
| | Water | 0.492 | 0.607 |
| Hydrophobic medium | Span40 | 1.257 | 1.213 |
| | Lecithin | 2.514 | 2.427 |
| | Ethyl-isovalerate | 10.885 | 10.508 |
| | Glyceryl monooleate | 2.363 | 2.281 |
| | Glyceryl tributyrate | 24.575 | 23.725 |
| | Coconut oil | — | — |
| | Castor oil | 45.633 | 44.054 |

The production process for all these above formulations is essentially as described in FIG. 1 and in Example 11.

Example 8

Effect of Dose of Sodium Octanoate Incorporated in Formulation on Formulation Activity The effect of increasing the amount of sodium octanoate (Na—C8) in the formulation on the activity of the formulation was tested using formulations containing dextran (average MW=4.4 kDa, FITC labeled) as cargo compound and different doses of Na—C8 namely, formulation A in Table 3A (which contains 12% sodium octanoate by weight) and similar dextran formulations containing different Na—C8 doses: 9%, 6% and 3% respectively.

To test the activity of these formulations in the jejunum of non-anesthetized rats, a rat model was established in which two different cannulas are surgically implanted in male Sprague-Dowley rats
1—Jejunal cannula to bypass the stomach and enable direct formulation administration to the jejunum.
2—Jugular vein cannula to determine the systematic levels of the administered dextran following jejunal administration. Rats are allowed to recover for 4 days before the study and are deprived of food for 18 hours before the start of the study.

Figure 6:
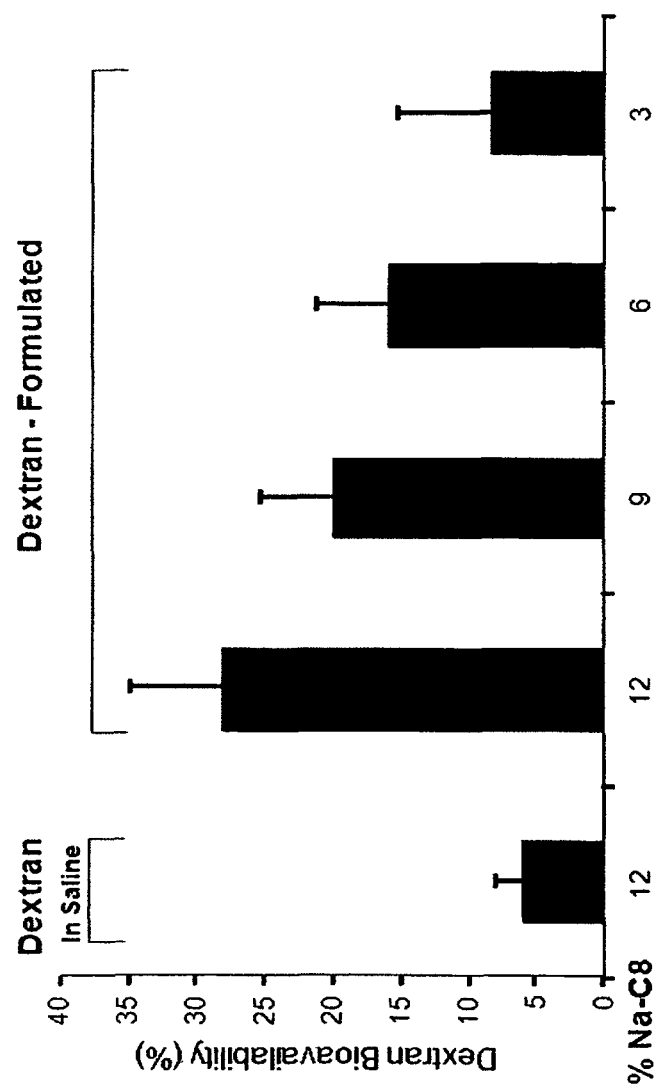
FIG. 6 presents data referenced in accompanying Example 8.

FIG. 6 presents data from a study which determines FITC-labeled dextran (4.4 kDa) bioavailability in non-anesthetized rats following intra-jejunal administration of formulations containing different amounts of Na—C8 or FITC-labeled dextran solubilized with the Na—C8 in saline solution (control).

The bioavailability of the different dextran formulations and the control was evaluated by administrating the different formulations directly to the jejunum of non-anesthetized rats and measuring plasma dextran levels at 3, 6, 10, 25, 60 and 90 minutes post administration. Levels of plasma dextran following administration of dextran in formulation or in saline were compared to the levels of plasma dextran after intravenous administration. Exposure values, AUC (0-90), were determined for jejunal and intravenous administration and the absolute bioavailability (aBA) was calculated according to the following equation:

$$aBA=(\text{jejunal } AUC(0\text{-}90))/(iv\ AUC(0\text{-}90))*(iv\ \text{dose}/\text{jejunal dose}).$$

Data are presented as Mean±SD (n≥5 rats per group).

The results show that increasing the amount of Na—C8 incorporated in the formulation improves the bioavailability of the dextran in a dose-responsive manner, reaching almost 30% aBA at the 12% (w/w) dose. Dextran administered with Na—C8 at similar doses and suspended in a saline solution (i.e. not formulated) showed much lower bioavailability (~6% aBA). Further results dose-response results are shown in Example 26.

Example 9

Effect of the Ratio of Hydrophilic Fraction/Hydrophobic Medium on Formulation Activity The effect on formulation activity of changing the ratio (weight/weight) between the hydrophilic fraction and the hydrophobic medium was tested using formulations containing dextran (average MW=4.4 kDa, FITC labeled) as cargo (formulations A and B in Table 3A). The in vivo non-anesthetized rat model described in Example 8 was used in order to compare the activity of the described formulations.

Table 4 presents bioavailability data following intra-jejunal administration of formulations comprising a different ratio of hydrophilic fraction to hydrophobic medium.

TABLE 4

| Cargo | Formulation | Weight ratio between hydrophilic/hydrophobic medium | Animal model | Route of administration | N | % aBA ± SD |
|---|---|---|---|---|---|---|
| Dextran | A | 1/5.2 | Rat Non-anesthetized | Jejunal | 17 | 28.0 ± 6.8 |
| | B | 1/2.6 | | | 19 | 24.8 ± 25 |

Formulations A and B were administered directly to the jejunum of non-anesthetized rats and plasma dextran levels were measured at 3, 6, 10, 25, 60 and 90 minutes post formulation administration. The levels of dextran absorption from rat jejunum after administration of dextran in formulation were compared to the levels of dextran absorbed after intravenous administration. Exposure values, AUC (0-90), were determined for jejunal and intravenous administration and the absolute bioavailability (aBA) determined according to the following equation:

$$aBA=(\text{jejunal } AUC(0\text{-}90))/(iv\ AUC(0\text{-}90))*(iv\ \text{dose}/\text{jejunal dose}).$$

Data are presented as Mean±SD (n≥5 rats per group).

The results show that changing the ratio between the hydrophilic fraction and the hydrophobic medium in these formulations with a low % weight of therapeutic agent had no significant effect on the bioavailability of the cargo which gives a loading flexibility in devising additional formulations.

Example 10

Activity of Formulations Containing Different Cargo Compounds

In order to test the capability of the formulation platform, the activity of formulations containing three different cargo compounds (APIs) was tested in three different animal models: jejunal administration to non-anesthetized rats, rectal administration to anesthetized rats and jejunal administration to non-anesthetized pigs. Table 5 summarizes the results of representative experiments testing the bioavailability of formulations containing different APIs in the three different animal models described above.

TABLE 5

|   | API | Formulation | Animal model | Route of Administration | N | % BA | ±SD |
|---|-----|-------------|--------------|------------------------|---|------|-----|
| I | Teriparatide | I | Rat non-anesthetized | Jejunal | 5 | 14.0** | ±10.8 |
| II |  | I | Pig non-anesthetized | Jejunal | 5 | 15.0** | ±9.3 |
| III | Leuprolide | K | Rat non-anesthetized | Jejunal | 4 | 10.1* | ±7.5 |
| IV | hGH | P | Rat anesthetized | Rectal | 5 | 17.9** | ±3.9 |

*Absolute BA (compared to IV)
**Relative BA (compared to SC)

A. Leuprolide Absorption after Jejunal Administration of Leuprolide in Formulation to Rats Table 5-III presents data from a representative study relating to leuprolide aBA following IV (intravenous) administration of leuprolide solution (at 75 µg/Kg) and jejunal administration of leuprolide in formulation (at 450 µg/Kg; formulation K, Table 3B) to non-anesthetized rats, as previously described in Example 8.

Blood samples were drawn from the jugular vein at 3, 6, 10, 15, 25, 40, 60 and 90 minutes post jejunal administration and at 3, 10, 25, 40, 90 min, 2, 3.3 and 5 hours post IV administration, plasma was prepared and leuprolide levels were determined in each sample. Leuprolide levels in systemic circulation rose dramatically after jejunal administration of leuprolide in formulation. Leuprolide blood levels peaked by 3 minutes post administration. The average aBA achieved after jejunal administration of leuprolide in formulation was calculated as described in the above Examples and was 10.1%. In a control experiment, jejunal administration of leuprolide in PBS demonstrated negligible penetration to the bloodstream.

A similar leuprolide formulation containing 12% sodium octanoate as described in Table 1B was prepared; it was tested in the above model and showed bioavailability as follows:

rBA(compared to SC)=21.1%±12.0(CV=57%).

B. Teriparatide Absorption after Jejunal Administration of Teriparatide in Formulation to Rats Table 5-I presents data from a representative study relating to plasma teriparatide concentration-time profiles following SC administration of teriparatide solution (at 85 µg/formulation and jejunal administration of teriparatide (teriparatide) in formulation (at 550 µg/Kg; formulation I, Table 3B) to non-anesthetized rats, as previously described in Example 8. Blood samples were drawn from the jugular vein at 3, 6, 10, 25, 60 and 90 minutes post jejunal administration and at 3, 10, 30, 60, 90 min, 2 and 3 hours post SC administration, plasma was prepared and teriparatide levels were determined in each sample. Teriparatide levels in systemic circulation rose dramatically after jejunal administration of teriparatide in formulation. Teriparatide levels peaked by 3 minutes post-administration. The average rBA achieved after jejunal administration of teriparatide in formulation was calculated as described in the above Examples, and was 14.0%. In a control experiment, jejunal administration of teriparatide in saline demonstrated no penetration to the bloodstream.

C. Teriparatide Absorption after Jejunal Administration of Teriparatide in Formulation to Pigs Table 5-II presents data from a representative study relating to plasma teriparatide concentration-time profiles following SC administration of teriparatide solution (at 10.65 µg/Kg) and jejunal administration of teriparatide in formulation (at 100 µg/Kg; formulation I, Table 3B) to non-anesthetized pigs.

A pig model was established in which two different cannulas were surgically permanently implanted in female domestic pigs:

1—jejunal cannula to bypass the stomach and enable direct formulation administration to the jejunum.

2—jugular vein catheterization to determine the systematic levels of the administered cargo following jejunal administration.

Pigs were allowed to recover for 7 days before the experiment and deprived of food 18-20 hours before the start of the experiment.

Blood samples were drawn from the jugular vein at 0, 3, 6, 10, 15, 25, 40, 60, 90 minutes, 2, 2.5 and 3 hours post jejunal administration and at 0, 3, 6, 10, 15, 20, 30, 45, 60, 90 min, 2, 2.5, 3 and 4 hours post SC administration, plasma was prepared and teriparatide levels were determined in each sample. Teriparatide levels in systemic circulation rose dramatically after jejunal administration of teriparatide in formulation. Teriparatide levels peaked by 10 minutes post administration. The average rBA achieved after jejunal administration of teriparatide in formulation was calculated as described in the above Examples, and was 15.0%.

A similar pig experiment was performed using dextran (FD4, formulation A in Table 3A) and it was determined that the average bioavailability of dextran was 20% in pigs as compared to IV.

D. hGH Absorption after Rectal Administration of hGH in Formulation to Rats

Table 5-IV presents data from a representative study relating to plasma hGH concentration-time profiles following SC administration of hGH solution (at 81 μg/Kg) and rectal administration of hGH in formulation (at 800 μg/Kg; formulation P, Table 3C), to anesthetized rats.

Male Sprague-Dowley rats were deprived of food for 18 hours before the start of the experiment. Rats were anesthetized by a solution of ketamine: xylazine. The formulation (100 μL/rat) was administered rectally using a 14 G venflon. Blood samples were drawn from the jugular vein at 3, 6, 10, 15, 40, 60 and 90 minutes post rectal administration and at 15, 30, 45, 60, 90 min, 2, 3, and 4 hours post SC administration, plasma was prepared and hGH levels were determined in each sample. hGH levels in systemic circulation rose dramatically after rectal administration of hGH in formulation. hGH levels peaked by 15 minutes. The average rBA achieved after rectal administration of hGH in formulation was calculated as described in the above Examples and was 17.9%. In a separate experiment hGH was administered to the jejunum and the aBA was lower. In a control experiment, rectal administration of hGH in PBS demonstrated no penetration to the bloodstream.

Thus the results presented in Table 5 demonstrate that substantial exposure was obtained for all cargo compounds tested in all animal models tested.

The above results demonstrate that the formulations described herein enable delivery of a wide range of different macromolecules through the intestinal epithelium in different animal models.

Example 11

Detailed Production Process of a Formulation of Teriparatide

Production of the Hydrophilic Fraction:

To 200 mL water the following ingredients were slowly added one by one (with 2-3 minutes mixing between each ingredient): 172 mg of teriparatide, 200 mg of MgCl$_2$, 4.0 g of PVP-12, 17.52 g of sodium octanoate and 10.0 g of 2% MC-400 aqueous solution, prepared as follows: 1 g of MC-400 powder was added to 50 mL water at 60±2° C. while mixing. After 5 min of mixing, the beaker was transferred to ice until a clear solution was obtained.

After addition of the MC-400 solution, the solution was mixed for another 5 min and then lyophilized for about 24 h. This procedure produced about 22 g of hydrophilic fraction.

Production of the Hydrophobic Medium:

2 g of Span 40, 4 g of lecithin and 3.8 g of GMO were dissolved in 17.3 g of ethyl isovalerate while mixing. To this solution were added 39.1 g of GTB and 72.6 g of castor oil. This procedure produced about 136-138 g of hydrophobic medium.

Production of the Bulk Drug Product:

Mixing of the hydrophilic fraction and the hydrophobic medium was performed at 20±2° C.

15.7 g of the hydrophilic fraction was slowly added during mixing to 84.3 g of hydrophobic medium at 600±50 RPM. After addition of all the hydrophilic fraction, the mixing speed was increased to 2000±200 RPM for 2-10 min followed by 4-8 cycles of 15 min mixing at 600±50 RPM and 2 min mixing at 2000±200 RPM.

Degassing by vacuum was then applied as follows: 5 min at 600 mBar, 5 min at 500 mBar and 30-120 min at 400 mBar. The resulting suspension was poured into a 100 mL dark bottle and stored at 2-8° C. This is the teriparatide formulation designated "I" described in Table 3B.

All other formulations described herein were produced by this method, varying ingredients and quantities according to the details given in the relevant Tables (see e.g. Example 29). A diagram of this method (with insulin as cargo) is shown in FIG. 1.

Example 12

Effect of the Oil Incorporated in the Formulation on Formulation Activity

The effect of the type of oil incorporated in the formulation (in the hydrophobic medium) on formulation activity was tested. Formulations containing dextran (average MW=4.4 kDa, FITC labeled) as cargo compound and different types of oils in the hydrophobic medium (formulations E, F and G in Table 3A). were tested in rats.

To test the activity of these formulations in the jejunum of non-anesthetized rats, a rat model was established in which two different cannulas are surgically implanted in male Sprague-Dowley rats:

1—Jejunal cannula to bypass the stomach and enable direct formulation administration to the jejunum.

2—Jugular vein cannula to determine the systematic levels of the administered dextran following jejunal administration.

Rats are allowed to recover for 4 days before the study and are deprived of food for 18 hours before the start of the study.

Table 6 presents data from a study in non-anesthetized rats following intra-jejunal administration of formulations containing different oils in the hydrophobic medium.

TABLE 6

| Cargo | Formulation | Oil | N | % aBA ± SD |
|---|---|---|---|---|
| Dextran | E | Castor oil + GTB | 14 | 19.8 ± 5.5 |
| | F | Mineral oil + GTB | 5 | 12.2 ± 5.0 |
| | G | Olive oil + GTB | 5 | 12.0 ± 9.9 |

Formulations containing different oils were administered directly to the jejunum of non-anesthetized rats and plasma dextran levels were measured at 3, 6, 10, 25, 60 and 90 minutes post formulation administration. The levels of dextran absorption from rat jejunum after administration of dextran in formulation were compared to the levels of dextran absorbed after intravenous administration. Exposure values, AUC (0-90), were determined for jejunal and intravenous administration and the absolute Bioavailability (aBA) was determined according to the following equation:

$$aBA=(\text{jejunal }AUC(0\text{-}90))/(iv\ AUC(0\text{-}90))*(iv\text{ dose}/\text{jejunal dose}).$$

Data are presented as Mean±SD (n≥5 rats per group).

Similar bioavailability was achieved when dextran was incorporated into formulations containing castor oil or coconut oil. Good bioavailability was also obtained in rat jejunum when teriparatide was used as cargo compound using formulations I and J; these formulations contain castor oil and GTB, and castor oil and coconut oil, respectively.

The results showed that formulations containing different kinds of oils in their hydrophobic medium are active, enabling penetration of the cargo (dextran, teriparatide) carried by the formulation. Thus the data demonstrated that all tested oils enable bioavailability of the cargo carried by the formulation. Castor oil and coconut oil might be superior to the other tested oils.

Example 13

Preparation of a Formulation Using Granulation Instead of Lyophilization

Production of the Hydrophilic Fraction:

To a plastic bag, the following ingredients were added: 1.00 g of PVP-30, 6.70 g of sodium octanoate and 13.00 g of lactose monohydrate as binder. After 5 min of mixing, all of the powder was transferred into a mortar and pestle.

A dextran FD4 aqueous solution was prepared as followed: 0.42 g dextran was dissolved in 1.2 g of WFI. All of the dextran solution was then added slowly to the powder while using a low shear agitation in a mortar & pestle; the agitation took around 45 min. The mixture was then transferred into a lyophilization tray and was oven-dried for about 20 h at 50° C. This procedure produced about 20 g of hydrophilic fraction, which was a fine granulate.

Production of the Hydrophobic Medium:

2 g of Span 40, 4 g of lecithin and 3.8 g of GMO were dissolved in 17.3 g of ethyl isovalerate while mixing. To this solution were added 39.1 g of GTB and 72.6 g of castor oil. This procedure produced about 136-138 g of hydrophobic medium.

Production of the Bulk Drug Product:

Mixing of the hydrophilic fraction and the hydrophobic medium was performed at 20±2° C.

19.00 g (29.58% of the final BDP) of the hydrophilic fraction was slowly added during mixing to 45.23 g (70.42% of the final BDP) of hydrophobic medium at 600±50 RPM. After addition of all the hydrophilic fraction, the mixing speed was increased to 2000±200 RPM for 2-10 min followed by 4-8 cycles of 15 min mixing at 600±50 RPM and 2 min mixing at 2000±200 RPM.

Degassing by vacuum was then applied as follows: 5 min at 600 mBar, 5 min at 500 mBar and 30-120 min at 400 mBar. The resulting suspension was poured into a 100 mL dark bottle and stored at 2-8° C.

Rat Study:

The above suspension was administered rectally to rats as described above in the Examples and the results were as follows: 35% BA, 12.9% SD. Another batch of suspension prepared by granulation as described above was prepared and was administered to the jejunum of rats as described above in the Examples, and the results were as follows: 21.8% BA, 4.0% SD. A range of formulations are prepared in a similar manner using granulation and incorporating a selection of therapeutic agents and varying the amount of sodium octanoate.

Example 14

Selection of Capsules

In vitro experiments were carried out using separately three types of solutions: the hydrophobic medium as described in the above Examples, ethyl isovalerate alone, and ethyl isovalerate containing 5% of each of the following surfactants: lecithin, span 40 and glyceryl mono-oleate. 3 types of unsealed capsules, gelatin, starch and HPMC, were each filled with each of these solutions. The filled capsules were then maintained in vitro for 29 days at 22±2° C., 30-50% relative humidity. Gelatin and HPMC capsules gave the best results, namely no deformation of the capsule.

Similar experiments were carried out using the same three solutions, and gelatin and HPMC capsules. The capsules were filled with the solutions, sealed (bonded) and then were maintained for 8 days at 22±2° C., 30-50% relative humidity. Both types of capsules showed stability to the solutions tested i.e. there was no leakage and no deformation of the capsules.

Example 15

Effect of Varying the Cation in the Medium Chain Fatty Acid Salt

Formulations were prepared with dextran (FD4) similar to Formulation A of Table 3A except that 12% sodium octanoate (0.722M) was replaced by an equal molarity of lithium octanoate or potassium octanoate or arginine octanoate (the last as a model for an ammonium salt). These formulations are shown below in Table 7A.

TABLE 7A

| | | Formulation, cargo = dextran | | |
|---|---|---|---|---|
| | Ingredient | K-octanoate (% w/w) | Li-octanoate (% w/w) | Arg-octanoate (% w/w) |
| Hydrophilic fraction | API | 0.545 | 0.546 | 0.546 |
| | MgCl2 | 0.134 | 0.136 | 0.124 |
| | PVP-12 | 2.673 | 2.722 | 2.475 |
| | Potassium octanoate | 13.617 | 0.00 | 0.00 |
| | Lithium octanoate | 0.00 | 10.826 | 0.00 |
| | Arginine octanoate | 0.00 | 0.00 | 22.989 |
| | MC 400 | 0.134 | 0.136 | 0.124 |
| | Water | 0.684 | 0.627 | 0.919 |
| Hydrophobic medium | Span40 | 1.185 | 1.206 | 1.097 |
| | Lecithin | 2.369 | 2.412 | 2.193 |
| | Ethyl isovalerate | 10.26 | 10.45 | 9.50 |
| | Glyceryl monooleate | 2.227 | 2.268 | 2.062 |
| | Glyceryl tributyrate | 23.16 | 23.58 | 21.44 |
| | Castor oil | 43.01 | 43.79 | 39.82 |

These formulations were each tested in the rat jejunal model described in Example 8. The results were obtained and bioavailability was calculated. The results are shown below in Table 7B.

TABLE 7B

| Medium chain fatty acid salt in formulation tested | N | % BA ± SD |
|---|---|---|
| Sodium octanoate (Formulation A) | 18 | 22.2 ± 10.8 |
| Lithium octanoate | 11 | 8.4 ± 3.8 |
| Potassium octanoate | 10 | 7.9 ± 6.4 |
| Arginine octanoate | 12 | 17.5 ± 7.4 |

The formulation A used in the above experiment was a different batch to that used in Example 8, and so the BA results given here for formulation A differ slightly from those recited in Table 4.

The above results show that when 12% sodium octanoate was replaced in the formulation by an equivalent molarity of lithium octanoate or potassium octanoate, the formulation still had bioavailability but at a lower level. The arginine octanoate formulation had similar activity to the 12% sodium octanoate formulation.

Example 16

Effect of Addition of Medium Chain Alcohols (Geraniol and Octanol) to the Hydrophobic Medium Formulations containing geraniol (BASF) and octanol (Spectrum/MP) were prepared as described above, using the ingredients shown in Table 8. The sodium dodecanoate was obtained from Spectrum/Acros.

Formulation Q—low % Medium Chain Fatty Acid Salt:

A dextran (FD4) formulation was prepared essentially as described in Example 11, containing a total of 2.9% medium chain fatty acid salt—(sodium octanoate 1.042%+sodium dodecanoate 1.869%)—and also containing geraniol and octanol in the hydrophobic medium, all as shown in Table 8 below.

Formulation R—Over 10% Medium Chain Fatty Acid Salt:

A dextran formulation was prepared essentially as described for Formulation A except that geraniol and octanol were added to the hydrophobic medium, all as shown in Table 8.

TABLE 8

| | | Formulation, cargo | |
|---|---|---|---|
| | Ingredient | Dextran Q (% w/w) | Dextran R (% w/w) |
| Hydrophilic fraction | API | 0.545 | 0.456 |
| | NaOH | 0.029 | 0.000 |
| | MgCl$_2$ | 0.104 | 0.114 |
| | PVP-12 | 2.083 | 2.282 |
| | Sodium octanoate | 1.042 | 10.046 |
| | Sodium dodecanoate | 1.869 | — |
| | MC 400 | 0.104 | 0.114 |
| | Water | 0.231 | 0.521 |
| Hydrophobic medium | Geraniol | 9.148 | 8.39 |
| | Octanol | 8.627 | 7.92 |
| | Span40 | 1.041 | 0.96 |
| | Lecithin | 2.081 | 1.91 |
| | Ethyl isovalerate | 9.012 | 8.27 |
| | Glyceryl monooleate | 1.956 | 1.80 |
| | Glyceryl tributyrate | 21.825 | 20.03 |
| | Castor oil | 40.532 | 37.20 |

Formulation Q (low % MCFA salt) was tested in the intra-jejunal rat model described above and the bioavailability was calculated: aBA=4.4%, SD=3.8 (n=12). Formulation R (over 10% MCFA salt) was tested in the intra-jejunal rat model described above and the bioavailability was calculated: aBA=22.7%. SD=1.6 (n=6). The BA of these formulations do not differ significantly from similar formulations, described in the above Examples, which do not contain geraniol.

Example 17

Formulations for Gentamicin and for RNA

Formulations were prepared for gentamicin and for RNA essentially as described in Example 11, with the ingredients of the bulk drug product as shown below in Table 9. The gentamicin was obtained from Applichem and the RNA was polyinosinic-polycytidylic acid sodium salt (Sigma).

TABLE 9A

| | | Formulation, API | |
|---|---|---|---|
| | Ingredient | Gentamicin (% w/w) | RNA (% w/w) |
| Hydrophilic fraction | API | 6.000 | 0.100 |
| | NaOH | 0.670 | — |
| | MgCl$_2$ | 0.127 | 0.137 |
| | PVP-12 | 2.545 | 2.741 |
| | Sodium octanoate | 12.026 | 12.001 |
| | MC 400 | 0.127 | 0.137 |
| | Water | 0.860 | 0.605 |
| Hydrophobic medium | Span40 | 1.119 | 1.214 |
| | Lecithin | 2.238 | 2.429 |
| | Ethyl isovalerate | 9.69 | 10.52 |
| | Glyceryl monooleate | 2.103 | 2.283 |
| | Glyceryl tributyrate | 21.88 | 23.74 |
| | Castor oil | 40.62 | 44.09 |

The gentamicin formulation was tested in the rat jejunal model described above and in the rat rectal model described above (e.g. Examples 4 and 5). The gentamicin was assayed using an immunoassay (ELISA). The results are shown in Table 9B below; % BA is calculated compared comparing to IV administration. The formulations were shown to provide bioavailability to the gentamicin.

TABLE 9B

| Cargo | Formulation | ROA | N | % BA ± SD |
|---|---|---|---|---|
| Gentamicin | As Table 9A | jejunal | 6 | 12.9 ± 4.5 |
| | As Table 9A | rectal | 5 | 50.1 ± 5.8 |

Similarly, the RNA formulation of Table 9A is tested in the rat jejunal model and in the rat rectal model described above. The RNA is assayed and the formulation is expected to provide bioavailability to the RNA.

Example 18

Effect on Formulation Activity of the Surfactants in the Hydrophobic Medium

The effect on formulation activity of withdrawing surfactants from the hydrophobic medium was tested using formulations containing dextran (average MW=4.4 kDa, FITC labeled) as cargo (formulations A and H in Table 3A).

Table 10 presents data from a study in non-anesthetized rats following intra-jejunal administration of formulations with or without surfactants (e.g. Span40, lecithin, glyceryl monooleate) in the hydrophobic medium.

TABLE 10

| Cargo | Formulation | Surfactants in hydrophobic medium | N | % aBA ± SD |
|---|---|---|---|---|
| Dextran | A | + | 17 | 28.0 ± 6.8 |
| | H | − | 4 | 11.1 ± 8.2 |

Formulations with or without surfactants in the hydrophobic medium were administered directly to the jejunum of non-anesthetized rats and plasma dextran levels were measured at 3, 6, 10, 25, 60 and 90 minutes post formulation administration. The levels of dextran absorption from rat jejunum after administration of dextran in formulation were compared to the levels of dextran absorbed after intravenous administration.

Exposure values, AUC (0-90), were determined for jejunal and intravenous administration and the absolute bioavailability (aBA) was determined according to the following equation: aBA=(jejunal AUC(0-90))/(iv AUC(0-90))* (iv dose/jejunal dose). Data are presented as Mean aBA±SD.

Lower bioavailability was achieved when dextran was incorporated into a formulation not containing surfactants in the hydrophobic medium (formulation H) as compared to a formulation containing surfactants in the hydrophobic medium (formulation A). The results demonstrate that withdrawing surfactants from the hydrophobic medium adversely affects formulation activity.

Example 19

Effect on Formulation Activity of Withdrawing Medium Chain Fatty Acids from the Hydrophilic Fraction The effect on formulation activity of withdrawing medium chain fatty acids (MCFA) from the hydrophilic fraction was tested using formulations containing dextran (average MW=4.4 kDa, FITC labeled) as cargo.

Table 11 presents data from a study in non-anesthetized rats following intra-jejunal administration of formulations with or without sodium octanoate in the hydrophilic fraction (formulations A and D in Table 3A, respectively).

TABLE 11

| Cargo | Formulation | MCFA in hydrophilic fraction | N | % aBA ± SD |
|---|---|---|---|---|
| Dextran | A | + | 17 | 28.0 ± 6.8 |
|  | D | − | 5 | 0.6 ± 1.0 |

The formulations described above were administered directly to the jejunum of non-anesthetized rats and plasma dextran levels were measured at 3, 6, 10, 25, 60 and 90 minutes post formulation administration. The levels of dextran absorption from rat jejunum after administration of dextran in formulation were compared to the levels of dextran absorbed after intravenous administration. Exposure values, AUC (0-90), were determined for jejunal and intravenous administration and the absolute bioavailability (aBA) was determined according to the following equation:

$$aBA=(\text{jejunal } AUC(0\text{-}90))/(iv\ AUC(0\text{-}90))*(IV\ \text{dose}/\text{jejunal dose}).$$

Data are presented as Mean aBA±SD.

Negligible penetration of dextran was achieved when dextran was incorporated in a formulation lacking medium chain fatty acids in the hydrophilic fraction (formulation D, % aBA=0.6±1.0) as compared to a formulation containing sodium octanoate at 12% w/w in the hydrophilic fraction (formulation A, % aBA=28.0±6.8). The results demonstrate that a formulation without medium chain fatty acids in the hydrophilic fraction is not active.

A similar experiment was performed using octreotide as cargo in the improved formulation (see below). The rBA was 0.11% (CV=158%)

Example 20

Effect on Formulation Activity of Simplifying the Formulation

The effect on formulation activity of simplifying the formulation was tested using formulations containing dextran (average MW=4.4 kDa, FITC labeled) or octreotide (Novetide) as cargo. The basic formulation described in the above Examples (e.g. formulations designated A, I and P) was simplified by not adding $MgCl_2$, and MC 400 to the hydrophilic fraction and by not adding span40, lecithin and ethyl iso-valerate to the hydrophobic medium. There is a concomitant increase in the amounts of glyceryl monooleate (surfactant) and glyceryl tributyrate added to the hydrophobic medium. Such formulations are shown in Table 12A below. These simplified formulations show no precipitation visually although the particles are visible microscopically i.e. they are stable suspensions.

TABLE 12A

| | | Formulation, API | |
|---|---|---|---|
| | Ingredient | Dextran Simplified (% w/w) | Octreotide Simplified (% w/w) |
| Hydrophilic fraction | API | 0.545 | 0.058 |
| | NaOH | 0.001 | 0.000 |
| | $MgCl_2$ | 0.000 | 0.000 |
| | PVP-12 | 2.735 | 2.750 |
| | Sodium octanoate | 12.000 | 12.019 |
| | MC 400 | 0.000 | 0.000 |
| | Water | 0.611 | 0.593 |
| Hydrophobic medium | Span40 | 0.00 | 0.000 |
| | Lecithin | 0.00 | 0.000 |
| | Ethyl isovalerate | 0.00 | 0.000 |
| | Glyceryl monooleate | 5.91 | 5.947 |
| | Glyceryl tributyrate | 34.19 | 34.385 |
| | Castor oil | 44.00 | 44.248 |

The production process for these above simplified formulations is essentially as described in FIG. 1 and in Example 11 for the basic formulations.

The basic octreotide formulation is shown in Table 12B below.

TABLE 12B

| | Ingredient | Cargo Octreotide Basic Formulation M (% w/w) |
|---|---|---|
| Hydrophilic fraction (HFP) | Cargo | 0.058 |
| | NaOH | 0.000 |
| | $MgCl_2$ | 0.137 |
| | PVP-12 | 2.742 |
| | Sodium Octanoate | 12.003 |
| | MC 400 | 0.137 |
| | Water | 0.603 |
| Hydrophobic fraction (LFP) | Span40 | 1.215 |
| | Lecithin | 2.430 |
| | Ethyl-Iso-valerate | 10.522 |
| | Glyceryl | 2.284 |

TABLE 12B-continued

| Ingredient | Cargo Octreotide Basic Formulation M (% w/w) |
|---|---|
| Monooleate Glyceryl Tributyrate | 23.756 |
| Castor oil | 44.113 |

Table 13 presents data from a study in non-anesthetized rats following intra-jejunal administration of two different dextran formulations—formulation A of Table 3A and the simplified formulation shown in Table 12A.

TABLE 13

| Cargo | Formulation | N | AUC (0-60 min)/dose/kg b.w. ± SD |
|---|---|---|---|
| Dextran | A (basic) | 28 | 67062 ± 27368 |
|  | Simplified | 12 | 63897 ± 24210 |

The above results show that similar AUC values were achieved when dextran was incorporated into a formulation containing the basic formulation (formulation A) as compared to a simplified formulation.

Table 14 below presents data from a study in non-anesthetized rats following intra-jejunal administration of two different octreotide formulations—the basic formulation shown in Table 12B and the simplified formulation shown in Table 12A. The levels of octreotide absorption from rat jejunum after administration of octreotide in basic formulation and simplified formulation were obtained. Exposure values, AUC (0-25), were determined.

TABLE 14

| Cargo | Formulation | N | AUC (0-25 min)/dose/kg b.w. ± SD |
|---|---|---|---|
| Octreotide | Basic | 13 | 2.8 ± 1.4 |
|  | Simplified | 13 | 2.3 ± 0.8 |

The above results in Table 14 show that the AUC values were slightly less when octreotide was incorporated into a simplified formulation as compared to the full formulation.

Example 21

Effect on Formulation Activity of Replacing Castor Oil by Octanoic Acid

The effect on formulation activity of replacing castor oil (and glyceryl tributyrate and ethyl iso-valerate) by octanoic acid (Aldritch) was tested using a formulation containing dextran as cargo. This was done to maintain the C8 motif in the formulation i.e. it was considered it might be advantageous to have C8 acid in the hydrophobic medium in addition to the C8 salt in the hydrophilic fraction.

The effect of adding ricinoleic acid (Spectrum) was also tested by making a dextran formulation containing octanoic acid/ricinoleic acid. Ricinoleic acid was chosen since the main triglyceride component in castor oil is formed from ricinoleic acid. Three formulations of dextran were prepared as shown in Table 15A below. The basic dextran formulation was prepared essentially as described in the above Examples. The dextran octanoic formulation was prepared essentially as described in the above Examples but wherein castor oil, glyceryl tributyrate and ethyl iso-valerate were replaced by octanoic acid. This formulation was found to be a solution by visual analysis but true solubility analysis was not performed. It seems that the octanoic acid at high concentration (about 78% of this formulation) dissolves the solid hydrophilic fraction, with the PVP and sodium octanoate being soluble in octanoic acid at high concentration. The dextran ricinoleic/octanoic acid formulation was prepared essentially as described in the above Examples but wherein castor oil, glyceryl tributyrate and ethyl iso-valerate were replaced by a mixture of octanoic acid and ricinoleic acid. This formulation was a suspension as is usual for most of the formulations of this invention.

TABLE 15A

| | | Formulation, API | | |
|---|---|---|---|---|
| | Ingredient | Dextran basic (% w/w) | Dextran Octanoic acid (% w/w) | Dextran Ricinoleic/ Octanoic acid (% w/w) |
| Hydrophilic fraction | API | 0.545 | 0.545 | 0.545 |
|  | NaOH | 0.001 | 0.001 | 0.001 |
|  | $MgCl_2$ | 0.136 | 0.136 | 0.136 |
|  | PVP-12 | 2.726 | 2.726 | 2.726 |
|  | Sodium octanoate | 12.001 | 12.002 | 12.002 |
|  | MC 400 | 0.136 | 0.136 | 0.136 |
|  | Water | 0.622 | 0.622 | 0.622 |
| Hydrophobic medium | Span40 | 1.208 | 1.207 | 1.207 |
|  | Lecithin | 2.416 | 2.414 | 2.414 |
|  | Ethyl isovalerate | 10.46 | 0.00 | 0.00 |
|  | Glyceryl monooleate | 2.271 | 2.272 | 2.272 |
|  | Glyceryl tributyrate | 23.62 | 0.00 | 0.00 |
|  | Castor oil | 43.86 | 0.00 | 0.00 |
|  | Octanoic acid | 0.000 | 77.94 | 23.38 |
|  | Ricinoleic acid | 0.000 | 0.00 | 46.76 |
|  | Ethyl Octanoate | 0.000 | 0.00 | 7.80 |

The formulations described above in Table 15A were administered directly to the jejunum of non-anesthetized rats, and plasma dextran levels were measured post formulation administration. Exposure values, AUC, were determined for the different formulations. These results are shown below in Table 15B.

TABLE 15B

| Cargo | Formulation | N | AUC (0-60)/dose/kg b.w. ± SD |
|---|---|---|---|
| Dextran | Basic | 12 | 72385 ± 37827 |
|  | Octanoic acid | 11 | 180824 ± 32778 |
|  | Ricinoleic/Octanoic acid | 11 | 113204 ± 33057 |

The results shown above in Table 15B demonstrate that the absorption of dextran was much improved (over two-fold) in the formulation containing octanoic acid. Additionally, the shape of the graph was changed showing slower but longer release. This may be advantageous since this allows the API to be longer-acting in the body. The dextran ricinoleic/octanoic results showed less activity than the octanoic acid formulation, but was still improved over the basic formulation.

Since the octanoic acid and ricinoleic acid/octanoic acid formulations showed high activity, similar formulations were prepared with exenatide as cargo. Three formulations of exenatide were produced as shown in Table 16A below. The basic exenatide formulation was prepared essentially as described in the above Examples. The exenatide/octanoic formulation was prepared essentially as described in the above Examples but wherein castor oil, glyceryl tributyrate and ethyl iso-valerate were replaced by octanoic acid. This formulation containing about 78% octanoic acid was found to be a solution by visual analysis, as was the similar dextran formulation above. The exenatide ricinoleic/octanoic acid formulation was prepared essentially as described in the above Examples but wherein castor oil, glyceryl tributyrate and ethyl iso-valerate were replaced by a mixture of octanoic acid and ricinoleic acid.

TABLE 16A

|  | | Formulation, API | | |
|---|---|---|---|---|
|  | Ingredient | Exenatide basic (% w/w) | Exenatide Octanoic acid (% w/w) | Exenatide Ricinoleic/ Octanoic acid (% w/w) |
| Hydrophilic fraction | API | 0.055 | 0.055 | 0.055 |
|  | NaOH | 0.000 | 0.000 | 0.000 |
|  | MgCl$_2$ | 0.137 | 0.137 | 0.137 |
|  | PVP-12 | 2.742 | 2.742 | 2.742 |
|  | Sodium octanoate | 12.003 | 12.003 | 12.003 |
|  | MC 400 | 0.137 | 0.137 | 0.137 |
|  | Water | 0.603 | 0.603 | 0.603 |
| Hydrophobic medium | Span40 | 1.213 | 1.214 | 1.214 |
|  | Lecithin | 2.434 | 2.429 | 2.429 |
|  | Ethyl isovalerate | 10.522 | 0.000 | 0.000 |
|  | Glyceryl monooleate | 2.283 | 2.285 | 2.285 |
|  | Glyceryl tributyrate | 23.759 | 0.000 | 0.000 |
|  | Castor oil | 44.112 | 0.000 | 0.000 |
|  | Octanoic acid | 0.000 | 78.395 | 47.035 |
|  | Ricinoleic acid | 0.000 | 0.000 | 23.518 |
|  | Ethyl Octanoate | 0.000 | 0.000 | 7.842 |

The formulations described above in Table 16A were administered directly to the jejunum of non-anesthetized rats, and plasma exenatide levels were measured post formulation administration. Exposure values, AUC, were determined for the different formulations. These results are shown below in Table 16B.

TABLE 16B

| Cargo | Formulation | N | AUC (0-90) ± SD | % BA ± SD |
|---|---|---|---|---|
| Exenatide | Basic | 10 | 1961 ± 1791 | 8.8 ± 8.2 |
|  | Octanoic acid | 11 | 612 ± 350 | 3.1 ± 1.8 |
|  |  |  | [AUC (0-180) ± SD] |  |

TABLE 16B-continued

| Cargo | Formulation | N | AUC (0-90) ± SD | % BA ± SD |
|---|---|---|---|---|
|  | Ricinoleic/ Octanoic acid | 9 | 476 ± 321 | 2.2 ± 1.5 |

The results shown above in Table 16B demonstrate that the exenatide formulation containing octanoic acid showed bioavailability, but the absorption of exenatide was decreased compared to the basic formulation. The shape of the graph was changed showing slower but longer release as in the case of the dextran octanoic acid formulation above; this prolonged PK profile may be advantageous. Note that in the case of the octanoic acid formulation, AUC 0-180 min was used for BA calculations due to the prolonged PK profile. The exenatide ricinoleic/octanoic acid formulation had even lower bioavailability than the octanoic acid formulation.

Example 22

Dose Response for Octanoic Acid

A. Octreotide Formulations:

The effect on formulation activity of varying the amount of octanoic acid was tested using formulations containing octreotide as cargo. Four formulations of octreotide were prepared using 0%, 5%, 10% or 15% octanoic acid as shown in Table 17 below. The formulations are basic octreotide formulations prepared essentially as described above wherein the amount of octanoic acid varies as described and the amount of other ingredients in the hydrophobic medium. (ethyl isovalerate and glyceryl tributyrate) was concomitantly reduced. (In these formulations the hydrophilic fraction was simplified to omit MgCl$_2$ and MC400.)

TABLE 17

|  |  | Formulation, API | | | |
|---|---|---|---|---|---|
|  | Ingredient | Octreotide 0% Octanoic (% w/w) | Octreotide 5% Octanoic (% w/w) | Octreotide 10% Octanoic (% w/w) | Octreotide 15% Octanoic (% w/w) |
| Hydrophilic fraction | API | 0.058 | 0.057 | 0.057 | 0.057 |
|  | PVP-12 | 2.750 | 2.750 | 2.750 | 2.750 |
|  | Sodium octanoate | 12.019 | 12.034 | 12.034 | 12.034 |
|  | Water | 0.593 | 0.594 | 0.594 | 0.594 |
| Hydrophobic medium | Span40 | 1.217 | 1.219 | 1.219 | 1.219 |
|  | Lecithin | 2.441 | 2.437 | 2.437 | 2.437 |
|  | Ethyl isovalerate | 10.554 | 0 | 0 | 0 |
|  | Octanoic acid | 0 | 5.053 | 10.553 | 15.021 |
|  | Glyceryl monooleate | 2.290 | 2.291 | 2.291 | 2.291 |
|  | Glyceryl tributyrate | 23.832 | 29.325 | 23.825 | 19.357 |
|  | Castor oil | 44.246 | 44.241 | 44.241 | 44.241 |

B. Exenatide Formulations:

The effect on formulation activity of varying the amount of octanoic acid was tested using formulations containing exenatide as cargo. Five formulations of exenatide were prepared using 0%, 10%, 15%, 20% or 35% octanoic acid as shown in Table 18 below. The formulations are basic exenatide formulations prepared essentially as described above wherein the amount of octanoic acid varies as described and the amount of other ingredients in the hydrophobic medium (ethyl isovalerate and glyceryl tributyrate) was concomitantly reduced.

TABLE 18

| | Ingredient | Exenatide 0% Octanoic (% w/w) | Exenatide 10% Octanoic (% w/w) | Exenatide 15% Octanoic (% w/w) | Exenatide 20% Octanoic (% w/w) | Exenatide 35% Octanoic (% w/w) |
|---|---|---|---|---|---|---|
| Hydrophilic fraction | API | 0.055 | 0.055 | 0.055 | 0.055 | 0.055 |
| | MgCl$_2$ | 0.137 | 0.137 | 0.137 | 0.137 | 0.137 |
| | PVP-12 | 2.742 | 2.742 | 2.742 | 2.742 | 2.742 |
| | Sodium octanoate | 12.003 | 12.003 | 12.003 | 12.003 | 12.003 |
| | MC 400 | 0.137 | 0.137 | 0.137 | 0.137 | 0.137 |
| | Water | 0.603 | 0.603 | 0.603 | 0.603 | 0.603 |
| Hydrophobic medium | Span40 | 1.213 | 1.213 | 1.213 | 1.213 | 1.213 |
| | Lecithin | 2.434 | 2.434 | 2.434 | 2.434 | 2.434 |
| | Ethyl isovalerate | 10.522 | 0 | 0 | 0 | 0 |
| | Octanoic acid | 0 | 10.522 | 15.081 | 20.085 | 34.282 |
| | Glyceryl monooleate | 2.283 | 2.283 | 2.283 | 2.283 | 2.283 |
| | Glyceryl tributyrate | 23.759 | 23.759 | 19.201 | 14.197 | 0.000 |
| | Castor oil | 44.112 | 44.112 | 44.112 | 44.112 | 44.112 |

The formulations described above in Tables 17 and 18 above were administered directly to the jejunum of non-anesthetized rats, and plasma octreotide or exenatide levels were measured post formulation administration. Exposure values, AUC, were determined for the different formulations. These results are shown below in Table 19.

TABLE 19

| Cargo | Formulation | N | AUC (0-60)/dose/kg b.w. ± SD |
|---|---|---|---|
| Octreotide | Basic | 14 | 2.8 ± 1.0 |
| | Basic 5% Octanoic acid | 12 | 2.7 ± 1.2 |
| | Basic) 10% Octanoic acid | 12 | 3.2 ± 1.2 |
| | Basic 15% Octanoic acid | 12 | 4.5 ± 2.3 |
| Exenatide | Basic | 10 | 3.9 ± 3.8 |
| | Basic, 10% Octanoic acid | 15 | 4.6 ± 2.8 |
| | Basic, 15% Octanoic acid | 6 | 3.0 ± 1.8 |
| | Basic, 20% Octanoic acid | 5 | 2.2 ± 0.5 |
| | Basic, 35% Octanoic acid | 6 | 1.9 ± 0.7 |

The results shown above in Table 19 demonstrate that the octreotide formulation shows increased activity compared to the basic formulation as the amount of octanoic acid is increased to 15% (the maximum amount tested). Additionally, the results shown above in Table 19 demonstrate that the exenatide formulation shows increased activity compared to the basic formulation as the amount of octanoic acid is increased to 15% and the activity decreases at higher levels of octanoic acid.

Example 23

Effect of Different Medium Chain Fatty Acid Salts

A. Sodium Sebacate (Disodium Salt of Decanedioic Acid):

The effect on formulation activity of replacing sodium octanoate by sodium sebacate (disodium C10 salt) in a dextran formulation was tested. The sodium sebacate was prepared in situ from sebacic acid (Aldrich) and sodium hydroxide. The formulation produced is described in Table 20 below. The formulation was prepared essentially as described above but 12% sodium octanoate was replaced by sodium sebacate, at the same molar concentration as sodium octanoate i.e. an equimolar amount of sodium sebacate was used (viz., 0.72M).

TABLE 20

| | Ingredient | Formulation, API Dextran Na-Sebacate (% w/w) |
|---|---|---|
| Hydrophilic fraction | API | 0.545 |
| | NaOH | 0.000 |
| | MgCl$_2$ | 0.129 |
| | PVP-12 | 2.589 |
| | Sodium Sebacate | 16.190 |
| | MC 400 | 0.129 |
| | Water | 0.783 |
| Hydrophobic medium | Span40 | 1.147 |
| | Lecithin | 2.295 |
| | Ethyl isovalerate | 9.94 |
| | Glyceryl monooleate | 2.157 |
| | Glyceryl tributyrate | 22.44 |
| | Castor oil | 41.66 |

The formulation described above in Table 20 was administered directly to the jejunum of non-anesthetized rats, and plasma dextran levels were measured post formulation administration. Exposure value, AUC, was determined for the formulation and this is compared with a similar formulation prepared with sodium octanoate. These results are shown below in Table 21.

TABLE 21

| Cargo | Formulation | N | AUC (0-60)/dose/kg b.w. ± SD |
|---|---|---|---|
| Dextran | With Na-octanoate | 12 | 72385 ± 37827 |
| | With Na-Sebacate | 9 | 18691 ± 11887 |

The results shown in Table 21 demonstrate that the dextran formulation containing sodium sebacate showed activity, but the absorption of dextran was decreased compared to the formulation containing an equimolar amount of sodium octanoate.

B. Mono-Sodium Suberate or Di-Sodium Suberate

Octreotide-containing formulations were prepared wherein 12% sodium octanoate was replaced by an equimolar amount (0.72M) of mono-sodium suberate or of di-sodium suberate, which are C8 salts. These sodium salts were prepared in situ from suberic acid (Tokyo Chemical Industry Co.) and sodium hydroxide.

TABLE 22A

| | | Formulation, API | |
|---|---|---|---|
| | Ingredient | Octreotide mono-Sodium suberate (0.72M) (% w/w) | Octreotide di-Sodium suberate (0.72M) (% w/w) |
| Hydrophilic fraction | API | 0.058 | 0.059 |
| | PVP-12 | 2.650 | 2.620 |
| | mono-Sodium Suberate | 15.087 | 0 |
| | di-Sodium Suberate | 0 | 15.996 |
| | Water | 0.712 | 0.747 |
| Hydrophobic medium | Span40 | 1.173 | 1.159 |
| | Lecithin | 2.352 | 2.325 |
| | Ethyl isovalerate | 10.169 | 10.055 |
| | Glyceryl monooleate | 2.206 | 2.181 |
| | Glyceryl tributyrate | 22.962 | 22.704 |
| | Castor oil | 42.632 | 42.152 |

The formulations described above in Table 22 are administered directly to the jejunum of non-anesthetized rats, and plasma octreotide levels are measured post formulation administration. Exposure values, AUC, are determined for the formulations and this is compared with a similar formulation prepared with sodium octanoate.

C. Geranic Acid Salt

Two octreotide-containing formulations were prepared essentially as described above wherein 12% sodium octanoate was replaced by 18% geranic acid sodium salt (0.95M) and 14.6% (0.77M) geranic acid sodium salt, which is 3,7-dimethyl-2,6-octadienoic acid (obtained from SAFC). The formulations produced are described in Table 22B below.

TABLE 22B

| | | Formulation, API | |
|---|---|---|---|
| | Ingredient | Octreotide NaGeranate A (% w/w) | Octreotide NaGeranate B (% w/w) |
| Hydrophilic fraction | API | 0.057 | 0.057 |
| | NaOH | 0 | 0.543 |
| | PVP 12 | 10.006 | 9.833 |
| | Sodium Geranate | 18.053 | 14.625 |
| | Water | 1.183 | 1.084 |
| Hydrophobic medium | Tween 80 | 2.001 | 1.970 |
| | Glyceryl monocaprylate | 4.001 | 3.923 |
| | Glyceryl tricaprylate | 63.235 | 65.927 |
| | Castor oil | 0.000 | 0 |

The formulations described above in Table 22B were administered directly to the jejunum of non-anesthetized rats, and plasma octreotide levels were measured post formulation administration. Exposure values, AUC, were determined for the formulations and this was compared with a similar formulation prepared with sodium octanoate. The results are shown below in Table 22C and they demonstrate that the formulation with 18% sodium geranate had similar activity as the 12% sodium octanoate formulation, and the formulation with 14.6% sodium geranate had increased activity.

TABLE 22C

| Cargo | Formulation | N | AUC (0-60)/dose/kg b.w. ± SD |
|---|---|---|---|
| Octreotide | Sodium geranate A | 9 | 4.48 ± 1.79 |
| | Sodium geranate B | 9 | 6.33 ± 2.1 |
| | Improved | 9 | 4.38 ± 1.66 |

Example 24

Effect of PVP (Polyvinylpyrrolidone) on Formulation Activity

The effect on formulation activity of replacing PVP-12 by mannitol (Sigma) was tested using formulations containing exenatide as cargo. It was understood in the art that PVP-12 is a stabilizer and could be replaced in the formulation by another stabilizer such as mannitol. The formulation shown in Table 23 below was prepared. This formulation is a basic exenatide formulation prepared essentially as described above, but wherein PVP-12 is replaced by mannitol.

TABLE 23

| | Ingredient | Formulation, API Exenatide Mannitol (% w/w) |
|---|---|---|
| Hydrophilic fraction | API | 0.055 |
| | MgCl$_2$ | 0.137 |
| | Mannitol | 2.742 |
| | Sodium octanoate | 12.003 |
| | MC 400 | 0.137 |
| | Water | 0.603 |
| Hydrophobic medium | Span40 | 1.213 |
| | Lecithin | 2.434 |
| | Ethyl isovalerate | 10.522 |
| | Glyceryl monooleate | 2.283 |
| | Glyceryl tributyrate | 23.759 |
| | Castor oil | 44.112 |

The formulation described above in Table 23 was administered directly to the jejunum of non-anesthetized rats, and plasma exenatide levels were measured post-formulation administration. Exposure values, AUC, were determined for the formulation compared to the basic formulation. These results are shown below in Table 24.

TABLE 24

| Cargo | Formulation | N | AUC (0-60)/dose/kg b.w. ± SD |
|---|---|---|---|
| Exenatide | Basic | 10 | 3.9 ± 3.8 |
| | Mannitol instead of PVP-12 | 6 | 1.6 ± 1.7 |

The results shown above in Table 24 demonstrate the surprising and unexpected result that the exenatide formulation without PVP-12 had significantly decreased activity compared to the basic formulation. It was thus decided to investigate further the effect of PVP on bioavailability.

The effect on formulation activity of varying the molecular weight of PVP was tested using formulations containing exenatide as cargo. Three formulations of exenatide were prepared using either PVP-12, PVP-17 or PVP-25 (all obtained from BASF). PVP-12, PVP-17 and PVP-25 are all polyvinylpyrrolidone polymers; the average molecular weights are about 2500-3000, 10000 and 30000 respectively. The formulations are basic exenatide formulations prepared essentially as described above wherein the PVP varies as described and wherein the hydrophilic fraction has been simplified to omit $MgCl_2$ and MC400.

TABLE 25

| | Ingredient | Formulation, API Exenatide PVP- 12/17/25 (% w/w) |
|---|---|---|
| Hydrophilic fraction | API | 0.022 |
| | PVP 12/17/25 | 2.752 |
| | Sodium octanoate | 12.005 |
| | Water | 0.602 |
| Hydrophobic medium | Span40 | 1.218 |
| | Lecithin | 2.442 |
| | Ethyl isovalerate | 10.561 |
| | Glyceryl monooleate | 2.291 |

TABLE 25-continued

| Ingredient | Formulation, API Exenatide PVP- 12/17/25 (% w/w) |
|---|---|
| Glyceryl tributyrate | 23.846 |
| Castor oil | 44.272 |

The three formulations described above in Table 25 were administered directly to the jejunum of non-anesthetized rats, and plasma exenatide levels were measured post-formulation administration. Exposure values, AUC, were determined for the formulations. The results are shown below in Table 26.

TABLE 26

| Cargo | Formulation | N | AUC (0-60)/dose/kg b.w. ± SD |
|---|---|---|---|
| (a) | PVP- 12 | 11 | 8.0 ± 7.7 |
| Exenatide | PVP- 17 | 6 | 3.4 ± 2.9 |
| (b) | PVP- 25 | 5 | 2.6 ± 2.3 |

The results shown above in Table 26 demonstrate that the exenatide formulations containing PVP-12 showed much higher activity than the exenatide formulations containing PVP-17 and PVP-25. Thus the effect of PVP-12 only was investigated further, and it was decided to perform a dose—response study using PVP-12. The effect of increasing the amount of PVP-12 in the formulation on the activity of the formulation was tested using formulations containing octreotide as cargo compound and different doses of PVP-12 as shown in Table 27 below. The PVP-12 doses tested were 2.75% (the standard dose used in the above formulations) and 5.0%, 7.5% and 10.0% PVP-12; the hydrophilic fraction has been simplified to omit $MgCl_2$ and MC400. The formulation containing 10% PVP was semi-solid i.e. it was apparently a semi-solid suspension.

TABLE 27

| | | Formulation, API | | | |
|---|---|---|---|---|---|
| | Ingredient | Octreotide PVP 2.75% (% w/w) | Octreotide PVP 5.0% (% w/w) | Octreotide PVP 7.5% (% w/w) | Octreotide PVP 10.0% (% w/w) |
| Hydrophilic fraction | API | 0.058 | 0.057 | 0.057 | 0.057 |
| | PVP- 12 | 2.750 | 5.013 | 7.514 | 10.046 |
| | Sodium octanoate | 12.019 | 12.031 | 12.037 | 12.018 |
| | Water | 0.593 | 0.684 | 0.784 | 0.885 |
| Hydrophobic medium | Span40 | 1.217 | 1.183 | 1.145 | 1.108 |
| | Lecithin | 2.441 | 2.373 | 2.297 | 2.222 |
| | Ethyl isovalerate | 10.554 | 10.259 | 9.934 | 9.608 |
| | Glyceryl monooleate | 2.290 | 2.226 | 2.155 | 2.084 |
| | Glyceryl tributyrate | 23.832 | 23.166 | 22.431 | 21.694 |
| | Castor oil | 44.246 | 43.009 | 41.645 | 40.278 |

The formulations described above in Table 27 were administered directly to the jejunum of non-anesthetized rats, and plasma octreotide levels were measured post-formulation administration. Exposure values, AUC, were determined for the four different formulations. These results are shown below in Table 28A.

TABLE 28A

| Cargo | Formulation | N | AUC (0-60)/dose/kg b.w. ± SD |
|---|---|---|---|
| Octreotide | 2.75% PVP- 12 | 14 | 2.8 ± 1.0 |
| | 5.0% PVP- 12 | 12 | 3.7 ± 1.6 |
| | 7.5% PVP- 12 | 12 | 4.2 ± 1.5 |
| | 10.0% PVP- 12 | 11 | 4.7 ± 1.4 |

The results shown above in Table 28A demonstrate that the absorption of octreotide increased dramatically as the amount of PVP in the formulation increased. The formulation containing 10% PVP-12 had absorption of octreotide about 1.7 times greater that the formulation containing 2.75% PVP-12. An improved octreotide formulation in which there was 10% PVP-12 but no sodium octanoate showed virtually no activity. The rBA was 0.11% (CV=158%) n=5.

It appears that the medium chain fatty acid salt acts as a permeability enhancer (by facilitating or enhancing permeability and/or absorption of the therapeutic agent), and that the PVP serves to increase the effect of the permeability enhancer in a synergistic manner since the PVP alone has virtually no effect. See also Example 31.

A further experiment was performed to investigate if the 10% PVP-12 could be replaced by dextran and still maintain activity of the formulation. The dextran was manufactured by Fluka; the average molecular weight is ~6000. The formulations were prepared essentially as described above wherein the PVP and dextran varies as described and wherein the hydrophilic fraction has been simplified to omit $MgCl_2$ and MC400 and where the sodium octanoate was increased to 15%; see Example 26.

TABLE 28B

| | | Formulation, API | | |
|---|---|---|---|---|
| | Ingredient | Octreotide 10% PVP (% w/w) | Octreotide 10% Dextran no PVP (% w/w) | Octreotide 5% Dextran no PVP (% w/w) |
| Hydrophilic fraction | API | 0.058 | 0.058 | 0.058 |
| | PVP-12 | 10.011 | 0.0 | 0.0 |
| | Dextran | 0.0 | 10.011 | 5.011 |
| | Sodium octanoate | 15.008 | 15.008 | 15.015 |
| | Water | 1.003 | 1.003 | 0.803 |
| Hydrophobic medium | Tween 80 | 2.027 | 2.027 | 2.169 |
| | Glyceryl monocaprylate | 4.036 | 4.036 | 4.319 |
| | Glyceryl tricaprylate | 40.714 | 40.714 | 43.574 |
| | Castor oil | 27.143 | 27.143 | 29.049 |

The three formulations described above in Table 28B were administered directly to the jejunum of non-anesthetized rats, and plasma octreotide levels were measured post-formulation administration. Exposure values, AUC, were determined for the formulations. The results are shown below in Table 28C.

TABLE 28C

| Cargo | Formulation | N | AUC (0-25)/dose/kg b.w. ± SD |
|---|---|---|---|
| Octreotide | 10% PVP | 9 | 4.4 ± 1.7 |
| | 10% Dextran; no PVP | 5 | 3.3 ± 1.6 |
| | 5% Dextran; no PVP | 9 | 3.2 ± 1.5 |

The results shown above in Table 28C demonstrate that the absorption of octreotide decreased when PVP in the formulation was replaced by dextran but the activity was still significant. The formulation containing 10% dextran had absorption of octreotide about 75% of the formulation containing 10% PVP, and the formulation containing 5% dextran had absorption of octreotide about 73% of the formulation containing 10% PVP.

Example 25

A Comparative Study of C8, C9 and C10 Medium Chain Fatty Acid Salts viz., Sodium Octanoate, Sodium Nonanoate and Sodium Decanoate The effect on formulation activity of replacing sodium octanoate with other medium chain fatty acid sodium salts was tested using formulations containing octreotide as cargo. Three formulations of octreotide were prepared, as shown in Table 29 below. These are all basic formulations prepared essentially as described above where the hydrophilic fraction has been simplified to omit $MgCl_2$ and MC400 and wherein the medium chain fatty acid salt is an equimolar amount of sodium octanoate, sodium nonanoate or sodium decanoate.

TABLE 29

| | | Formulation, API | | |
|---|---|---|---|---|
| | Ingredient | Octreotide NaC8 12% (0.72M) (% w/w) | Octreotide NaC9 13% (0.72M) (% w/w) | Octreotide NaC10 14% (0.72M) (% w/w) |
| Hydrophilic fraction | API | 0.058 | 0.057 | 0.058 |
| | PVP-12 | 2.750 | 2.718 | 2.685 |
| | Sodium octanoate | 12.019 | 0 | 0 |
| | Sodium nonanoate | 0 | 13.023 | 0 |
| | Sodium decanoate | 0 | 0 | 14.019 |
| | Water | 0.593 | 0.632 | 0.670 |
| Hydrophobic medium | Span40 | 1.217 | 1.203 | 1.188 |
| | Lecithin | 2.441 | 2.412 | 2.383 |
| | Ethyl isovalerate | 10.554 | 10.428 | 10.303 |
| | Glyceryl monooleate | 2.290 | 2.262 | 2.235 |
| | Glyceryl tributyrate | 23.832 | 23.547 | 23.265 |
| | Castor oil | 44.246 | 43.718 | 43.194 |

The formulations described above in Table 29 were administered directly to the jejunum of non-anesthetized rats, and plasma octreotide levels were measured post-formulation administration. Exposure values, AUC, were determined for the formulations. The results are shown below in Table 30.

TABLE 30

| Cargo | Formulation | N | AUC (0-25)/dose/kg b.w. ± SD |
|---|---|---|---|
| Octreotide | sodium octanoate NaC8 | 9 | 2.1 ± 0.8 |
| | sodium nonanoate NaC9 | 10 | 2.5 ± 0.4 |
| | sodium decanoate NaC10 | 10 | 1.7 ± 0.4 |

The results shown above in Table 30 demonstrate that when sodium octanoate in the formulation is replaced by sodium nonanoate or by sodium decanoate there is similar activity. Based on statistical analysis, there is no difference in activity between all three formulations.

Example 26

Dose Response of Sodium Octanoate

The dose response of sodium octanoate at 12%, 15% and 18% was tested by making the formulations shown in Table 31. These are all basic formulations prepared essentially as described above where the hydrophilic fraction has been simplified to omit $MgCl_2$ and MC400 and the cargo compound was octreotide. Additionally the formulation was corrected for viscosity i.e. the same or similar viscosity was maintained for all three formulations; this was achieved by varying the amounts of castor oil and glyceryl tributyrate.

TABLE 31

|  |  | Formulation, API | | |
|---|---|---|---|---|
|  | Ingredient | Octreotide NaC8 12% (% w/w) | Octreotide NaC8 15% (% w/w) | Octreotide NaC8 18% (% w/w) |
| Hydrophilic fraction (simplified) | API | 0.058 | 0.058 | 0.058 |
|  | PVP- 12 | 2.750 | 2.652 | 2.554 |
|  | Sodium octanoate | 12.019 | 15.040 | 18.016 |
|  | Water | 0.593 | 0.710 | 0.825 |
| Hydrophobic medium | Span40 | 1.217 | 1.173 | 1.130 |
|  | Lecithin | 2.441 | 2.353 | 2.267 |
|  | Ethyl isovalerate | 10.554 | 10.175 | 9.802 |
|  | Glyceryl monooleate | 2.290 | 2.207 | 2.126 |
|  | Glyceryl tributyrate | 23.832 | 32.816 | 41.090 |
|  | Castor oil | 44.246 | 32.816 | 22.132 |

The formulations described above in Table 31 were administered directly to the jejunum of non-anesthetized rats, and plasma octreotide levels were measured post-formulation administration. Exposure values, AUC, were determined for the formulations. The results are shown below in Table 32.

TABLE 32

| Cargo | Formulation | N | AUC (0-60)/dose/kg b.w. ± SD |
|---|---|---|---|
| Octreotide | NaC8 12% | 14 | 2.8 ± 1.0 |
|  | NaC8 15% | 12 | 4.1 ± 1.9 |
|  | NaC8 18% | 12 | 3.6 ± 1.1 |

The results shown above in Table 32 demonstrate that when sodium octanoate in the formulation is increased from 12% to 15% there is an increase in activity but a further increase of sodium octanoate to 18% leads no higher activity than that obtained at 15%. Thus about 15% sodium octanoate appears to be the preferred amount.

Example 27

Investigation of the Effect of Varying the Hydrophilic/Lipophilic Balance of the Surfactants in the Formulation Table 33 below describes various octreotide formulations. The first column, formulation (a), is the basic formulation prepared essentially as described above where the hydrophilic fraction has been simplified to omit $MgCl_2$ and MC400, and the cargo compound is octreotide. The surfactants are Span 40, lecithin and glyceryl monooleate, and by calculation the HLB is approximately 5-6. In the other formulations (formulations b, c and d) the HLB was changed as indicated (to 3.5, 6.7 and 14) by replacing Span 40 and lecithin by differing amounts of Tween 80 and by varying the amount of glyceryl monooleate.

TABLE 33

|  |  | Formulation, API | | | |
|---|---|---|---|---|---|
|  | Ingredient | Octreotide HLB 5-6 [a] (% w/w) | Octreotide HLB 3.5[b] (% w/w) | Octreotide HLB 6.7[c] (% w/w) | Octreotide HLB 14[d] (% w/w) |
| Hydrophilic fraction | API | 0.058 | 0.057 | 0.057 | 0.057 |
|  | PVP-12 | 2.750 | 2.748 | 2.748 | 2.748 |
|  | Sodium octanoate | 12.019 | 12.027 | 12.027 | 12.027 |
|  | Water | 0.593 | 0.594 | 0.594 | 0.594 |
| Hydrophobic medium | Span40 | 1.217 | 0 | 0 | 0 |
|  | Lecithin | 2.441 | 0 | 0 | 0 |
|  | Ethyl isovalerate | 10.554 | 10.547 | 10.546 | 10.547 |
|  | Tween 80 | 0 | 0.502 | 2.003 | 5.500 |
|  | Glyceryl monooleate | 2.290 | 5.500 | 4.002 | 0.502 |
|  | Glyceryl tributyrate | 23.832 | 23.811 | 23.811 | 23.811 |
|  | Castor oil | 44.246 | 44.215 | 44.215 | 44.215 |

The formulations described above in Table 33 were administered directly to the jejunum of non-anesthetized rats, and plasma octreotide levels were measured post-formulation administration. Exposure values, AUC, were determined for the formulations. The results are shown below in Table 34.

TABLE 34

| Cargo | Formulation | N | AUC (0-25)/dose/kg b.w. ± SD |
|---|---|---|---|
| Octreotide | HLB 5-6 - [a] | 9 | 2.1 ± 0.8 |
|  | HLB 3.5 - [b] | 12 | 3.3 ± 0.9 |
|  | HLB 6.7 - [c] | 11 | 3.8 ± 0.9 |
|  | HLB 14 - [d] | 10 | 3.7 ± 0.9 |

The results shown above in Table 34 demonstrate that all the three new formulations replacing Span 40 and lecithin with Tween 80 [b, c and d] had much better activity than the basic formulation [a], even although the HLB in [b] was lower, in [c] was slightly higher and in [d] was much higher than the HLB of the surfactants in (a). Additionally, the activities of all the new formulations [(b, c, and d] were statistically very similar. Thus the HLB alone of the surfactants does not seem to affect activity but the characteristics of the surfactants appear to play an important role. In particular, replacing Span 40 and lecithin with Tween 80 is advantageous for activity in these octreotide formulations.

Example 28

Octreotide Formulations with Different Ratios of Glyceryl Tricaprylate to Castor Oil Based on the accumulation of results described above including the PVP-12 dose response results, the sodium octanoate dose response results and the surfactant results inter alia, a series of octreotide formulations were prepared using 10% PVP-12 and 15% sodium octanoate, and varying the ratio of glyceryl tricaprylate to castor oil. Additionally, glyceryl monooleate and glyceryl tributyrate were replaced (if used) by glyceryl monocaprylate and glyceryl tricaprylate (both supplied by Abitec). This is to maintain the C8 motif within the formulation. Thus the hydrophilic fraction contains a salt of a C8 acid (octanoate) and the hydrophobic medium contains monoglycerides and triglycerides incorporating the same C8 acid. The inventors believe that the use of C-8 compounds in both the hydrophilic fraction and in the hydrophobic medium may be advantageous for bioavailability. The amounts of Tween 80 and glyceryl monocaprylate were also varied in the formulations. The formulations were prepared are shown in Table 35A below. Formulations I, II, V and VI were semi-solid (apparently suspensions) and formulations III and IV were the usual liquid suspensions.

TABLE 35A

|  |  | Formulation, API | | | | | |
|---|---|---|---|---|---|---|---|
|  | Ingredient | Octreotide I (% w/w) | Octreotide II (% w/w) | Octreotide III (% w/w) | Octreotide IV (% w/w) | Octreotide V (% w/w) | Octreotide VI (% w/w) |
| Hydrophilic fraction | API | 0.058 | 0.058 | 0.058 | 0.058 | 0.058 | 0.058 |
|  | PVP-12 | 10.011 | 10.011 | 10.011 | 10.011 | 10.011 | 10.011 |
|  | Sodium octanoate | 15.008 | 15.008 | 15.008 | 15.008 | 15.008 | 15.008 |
|  | Water | 1.003 | 1.003 | 1.003 | 1.003 | 1.003 | 1.003 |
| Hydrophobic medium | Tween 80 | 2.027 | 2.027 | 2.027 | 2.027 | 6.063 | 6.062 |
|  | Glyceryl monocaprylate | 4.036 | 4.036 | 4.036 | 4.036 | 0 | 0 |
|  | Glyceryl tricaprylate | 40.714 | 13.571 | 61.071 | 67.857 | 40.714 | 0 |
|  | Castor oil | 27.143 | 54.286 | 6.786 | 0.000 | 27.143 | 67.857 |

The formulations described above in Table 35A were administered directly to the jejunum of non-anesthetized rats, and plasma octreotide levels were measured post-formulation administration. Exposure values, AUC, were determined for the formulations. The results are shown below in Table 35B.

TABLE 35B

| Cargo | Formulation | N | AUC (0-25)/dose/kg b.w. ± SD |
|---|---|---|---|
| Octreotide | Formulation I(GTC:castor oil 6:4) | 9 | 4.4 ± 1.7 |
|  | Formulation II(GTC:castor oil 2:8) | 8 | 3.0 ± 1.7 |
|  | Formulation III(GTC:castor oil 9:1) | 9 | 3.1 ± 0.5 |
|  | Formulation IV(GTC:castor oil 10:0) | 7 | 4.1 ± 2.1 |
|  | Formulation V -without GMC (GTC:castor oil 6:4) | 6 | 1.6 ± 1.0 |
|  | Formulation VI -without GMC>C (GTC:castor oil 0:10) | 7 | 1.1 ± 0.6 |

The results shown above in Table 35B demonstrate that formulations 1 and IV have greatest activity. Since castor oil is absent in formulation IV this demonstrates that castor oil is not essential for activity. It seems that a high GTC:castor oil ratio e.g. 6:4 is beneficial for activity. Additionally, since formulation V (which has low activity) has the same GTC: castor oil ratio as formulation I it appears that additionally GMC (or other monoglyceride) is desirable for activity. Additionally a formulation similar to formulation I of Table 36 was prepared but sodium octanoate was omitted. This formulation showed virtually no activity, rBA=0.1%.

Bulk drug product of formulation IV (improved, no castor oil) was milled with a 150 micron screen, and then particle size was determined using Malvern Laser Diffraction technology. Preliminary results indicated that 90% (v/v) of the particles were below 130 microns, and 50% (v/v) of the particles were below 45 microns.

Preliminary experiments using similar formulations to formulation I, but with varying increased amounts of octreotide all gave similar BA i.e. there was approximately linear exposure independent of API loading. A preliminary experiment using a similar formulation to formulation IV at even higher octreotide loading—1.5% (wt/wt)—also gave similar BA.

A similar improved formulation to formulation I above was prepared using FD4 as cargo instead of octreotide, and it was compared to a basic formulation. These formulations are described in Table 36A below.

TABLE 36A

|  | Ingredient | FD 4 Basic (no Mg, MC) (% w/w) | FD 4 Improved (% w/w) |
|---|---|---|---|
| Hydrophilic fraction | API | 0.545 | 0.545 |
|  | NaOH | 0.001 | 0 |
|  | PVP-12 | 2.734 | 10.012 |
|  | Sodium octanoate | 12.036 | 15.009 |
|  | Water | 0.613 | 1.023 |
| Hydrophobic medium | Tween 80 | 0 | 2.013 |
|  | Glyceryl monocaprylate | 0 | 4.008 |
|  | Glyceryl tricaprylate | 0 | 40.434 |
|  | Span40 | 1.21 | 0 |
|  | Lecithin | 2.42 | 0 |
|  | Ethyl-Iso-valerate | 10.49 | 0 |
|  | Glyceryl mono-oleate | 2.28 | 0 |
|  | Glyceryl tributyrate | 23.69 | 0 |
|  | Castor oil | 43.98 | 26.956 |

The formulations described above in Table 36A were administered directly to the jejunum of non-anesthetized rats, and plasma FD4 levels were measured post-formulation administration. Exposure values, AUC, were determined for the formulations. The results are shown below in Table 36B.

TABLE 36B

| Cargo | Formulation | N | AUC (0-90)/dose/kg b.w. ± SD |
|---|---|---|---|
| FD 4 (dextran) | Basic | 6 | 67448 ± 16977 |
|  | Improved | 6 | 95374 ± 47490 |

The results shown above in Table 36B demonstrate that the improved formulation has much greater activity than the basic formulation.

Example 29

Detailed Production Process for a Selected (Improved) Octreotide Formulation

The octreotide formulation in Example 28 (Table 6, first column) was prepared essentially as described in the above Examples. Below follows the detailed production process for this formulation.

Production of the Hydrophilic Fraction:

To 150 mL water the following ingredients were slowly added and mixed: 24.05 g of sodium octanoate, 16.04 g of PVP-12 and 92.4 g of 10 mg/mL aqueous octreotide solution. The resulting solution was lyophilized.

Production of the Hydrophobic Medium:

3.25 g Tween 80, 6.47 g of glyceryl monocaprylate, 65.25 g of glyceryl tricaprylate and 43.50 g of castor oil were mixed together.

Production of the Bulk Drug Product:

26.08 g of the hydrophilic fraction was slowly added to 73.92 g of the hydrophobic medium at 20±2° C. while mixing. After addition of the entire hydrophilic fraction, the mixing speed was increased. Degassing by vacuum was then applied and the resulting suspension was stored at 2-8° C.

To enable larger amounts of octreotide to be dissolved the following method was devised:

1. The amount of water of the hydrophilic fraction preparation was the same as the calculated volume of the final bulk drug product.
2. PVP-12 was dissolved in half of the above amount of water.
3. Sodium octanoate was dissolved in the second half amount of water.
4. Octreotide was dissolved in the PVP-12 solution (from paragraph 2).
5. The sodium octanoate solution was added to the octreotide and PVP-12 solution.

At this stage there was some precipitation, but it became soluble after mixing.

Example 30

Experiments in Pigs Using Capsules

In order to test the activity of the formulations of the invention when administrated in capsules, an animal model allowing capsule administration to pigs (domestic swine) was established. In order to bypass the stomach and allow direct administration of capsules to the small intestine of the pig, a well established model in dogs ("Nipple Valve model"; Wilsson-Rahmberg & O. Jonsson, Laboratory Animals (1997), 31, 231-240) was adapted to the commercial pig.

The two octreotide formulations shown below in Table 37 were prepared. The octreotide (x) formulation was prepared essentially as described above for the basic formulation wherein the hydrophilic fraction has been simplified to omit MgCl$_2$ and MC400. The octreotide (y) formulation was prepared essentially as described above for the improved octreotide formulation. The formulations were filled into gelatin capsules (from Capsugel), basic formulation (x) at 0.42 mL/capsule and improved formulation (y) at 0.44 mL/capsule, resulting in 5 mg net octreotide content in both types of filled capsules. The capsules were not enteric-coated i.e. they were uncoated.

TABLE 37

| | | Formulation, API | |
|---|---|---|---|
| | Ingredient | Octreotide (x) basic (% w/w) | Octreotide(y) improved (% w/w) |
| Hydrophilic fraction | API | 1.357 | 1.277 |
| | PVP-12 | 2.717 | 10.011 |
| | Sodium octanoate | 12.011 | 15.008 |
| | Water | 0.643 | 1.052 |
| Hydrophobic medium | Tween 80 | 0 | 1.992 |
| | Glyceryl monocaprylate | 0 | 3.967 |
| | Glyceryl tricaprylate | 0 | 40.016 |
| | Castor oil | 43.562 | 26.677 |
| | Span40 | 1.198 | 0 |
| | Lecithin | 2.403 | 0 |
| | Ethyl isovalerate | 10.391 | 0 |
| | Glyceryl monooleate | 2.254 | 0 |
| | Glyceryl tributyrate | 23.463 | 0 |

The formulations described above in Table 37 were administered directly to the small intestine of the non-anesthetized pigs via the gastric bypass described above, and plasma octreotide levels were measured post-administration. Exposure values, AUC were determined for the formulations. The % BA was calculated compared to the exposure to octreotide after subcutaneous administration. The results obtained are shown below in Table 38.

TABLE 38

| Cargo | Formulation | N | AUC (0-240) ± SD | % BA ± SD |
|---|---|---|---|---|
| Octreotide | Octreotide(x) | 4 | 896 ± 305 | 2.1 ± 0.7 |
| | Octreotide(y) | 4 | 2574 ± 889 | 6.2 ± 2.1 |

The above results in Table 38 show that there was bioavailability in the pig model for encapsulated formulations, for both the basic and improved formulations. Octreotide bioavailability of the improved formulation was about three times the level of bioavailability of the basic formulation.

The results given here for bioavailability are underestimated because sampling time was not sufficient for octreotide levels to go back to baseline (0 ng/mL). This was due to the unexpectedly longer exposure time in pigs as compared to what had been previously measured in rats. The shape of the graph was changed compared to the rat results showing longer time to reach maximal peak levels and extended time in which octreotide is resident in the blood. This may be advantageous since this allows the octreotide to be longer-acting in the body. Thus the actual bioavailability in pigs must be higher than the numbers given.

Based on the results in rats, the level of bioavailability in pigs of octreotide administered in aqueous solution is extrapolated to be about 0.1%. This level of bioavailability is below the level of sensitivity of the bioassay used for pigs.

Example 31

Dose-Response Results for PVP in the Improved Formulation

Further to the PVP results in Example 24, the effect on activity of increasing the amount of PVP-12 in the improved formulation was studied. The improved formulations, made essentially as described above, contained octreotide as cargo compound and different doses of PVP-12 as shown in Table 39 below. The PVP-12 doses tested were 7.5%, 10.0% and 15.0% PVP-12. The formulations containing 10% and 15.0% PVP were semi-solid i.e. they were apparently semi-solid suspensions- and the formulation containing 7.5% PVP was a viscous suspension.

TABLE 39

| | | Formulation, API | | |
|---|---|---|---|---|
| | Ingredient | Octreotide PVP 7.5% (% w/w) | Octreotide PVP 10.0% (% w/w) | Octreotide PVP 15.0% (% w/w) |
| Hydrophilic fraction | API | 0.058 | 0.058 | 0.058 |
| | PVP-12 | 7.506 | 10.011 | 15.009 |
| | Sodium octanoate | 15.012 | 15.008 | 15.009 |
| | Water | 0.903 | 1.003 | 1.203 |
| Hydrophobic medium | Tween 80 | 2.098 | 2.027 | 1.884 |
| | Glyceryl monocaprylate | 4.178 | 4.036 | 3.752 |
| | Glyceryl tricaprylate | 42.147 | 40.714 | 37.851 |
| | Castor oil | 28.098 | 27.143 | 22.234 |

The formulations described above in Table 39 were administered directly to the jejunum of non-anesthetized rats, and plasma octreotide levels were measured post-formulation administration. Exposure values, AUC, were determined for the three formulations. These results are shown below in Table 40.

TABLE 40

| | | | T |
|---|---|---|---|
| Cargo | Formulation | N | AUC (0-25)/dose/kg b.w. ± SD |
| Octreotide | 7.5% PVP-12 | 7 | 2.9 ± 2.2 |
| | 10.0% PVP-12 | 9 | 4.4 ± 1.7 |
| | 15% PVP-12 | 10 | 2.1 ± 1.2 |

The results shown above in Table 40 demonstrate that the absorption of octreotide was greatest when PVP in the formulation was 10%, and increasing the amount to 15% results in significant decrease in activity. This confirms the choice of 10% PVP in the improved formulation.

Experiment 32

Activity of API Packed in Formulation Compared to API Administered Concomitant to Formulation Three different basic formulations of three different cargo compounds were prepared (dextran, gentamicin and exenatide), essentially as described above (wherein the basic formulation is the basic non-simplified hydrophilic fraction). Each of these three formulations was administered directly to the jejunum of non-anesthetized rats, and plasma cargo levels were measured post-formulation administration. Exposure values, AUC, were determined for the formulations. Additionally, a similar formulation was prepared with a non-relevant cargo compound (a mock formulation). Separately, the mock formulation was administered concomitantly with dextran, gentamicin or exenatide in aqueous solution and exposure values, AUC, were determined. Concomitant administration was achieved by administrating cargo in aqueous solution immediately followed by mock formulation administration via a jejunal-implanted cannula (gastric bypass). For each compound, exposure after administration of the formulated cargo was compared to exposure after administration of the unformulated cargo (concomitant). The comparative results are shown below in Table 41. The results show that there is higher activity (bioavailability) when the cargo is formulated compared to unformulated (concomitant) in all three cases, and that exenatide showed by far the greatest increase in activity due to formulation. Note that dextran and gentamicin are compounds that are not sensitive to protease degradation, whereas exenatide being a peptide is subject to degradation by intestinal enzymes. The large difference in activity between the formulated exenatide compared to unformulated exenatide may be due to the protective effect of the formulation against degradation.

TABLE 41

| API/cargo | Formulated versus unformulated (fold activity) |
|---|---|
| Dextran | 1.7 |
| Gentamicin | 1.5 |
| Exenatide | 4.4 |

Example 33

Intestinal Hyperpermeability Evaluation

A. Size Limitation:

The technology and formulations described above are intended to enhance the permeability of the intestine, allowing specific delivery of proteins, peptides and other otherwise impermeable molecules across this barrier. A certain degree of non-specific penetration of intestinal content may result as a side-effect of this enhancement of specific permeability. The size of molecules which could possibly penetrate the intestine in a non-specific manner was evaluated using different molecular size markers.

In order to evaluate the molecular size limit of increased GI permeability, five different FITC-labeled dextrans of different molecular weight were chosen to serve as molecular markers to test increased intestinal permeability; the average molecular weight of the five dextrans was 4.4, 10, 20, 40 and 70 kDa, equivalent to a radius of 14, 23, 33, 45 and 60 Å respectively. These different size markers were administered directly to the jejunum of non-anaesthetized rats, through an intestinal implanted cannula, and showed virtually no basal intestinal penetration when tested alone. Each of these markers was then administered directly to the jejunum of non-anesthetized rats together with 300 μL of basic formulation, and the degree of its penetration was evaluated by testing dextran levels in blood.

Figure 7:
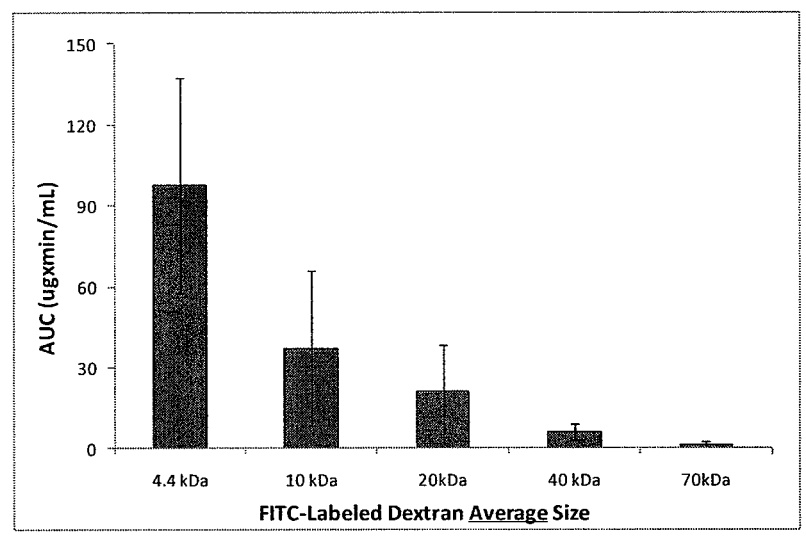
FIG. 7 presents molecular weight marker permeability data referenced in accompanying Example 33.

The plasma dextran levels were measured pre-dosing and at 3', 6', 10', 25', 60', 90' minutes post formulation administration. Exposure values, AUC (0-90), were determined and the results are shown in FIG. 7. Data is presented as MEAN±SD, n≥4.

The results show that while the smallest molecular marker tested (dextran of average MW=4.4 kDa), penetrates the intestine when administered concomitantly with a formulation, as the molecule size increases, penetration extent decreases: a marker molecule of 10 kDa penetrates to a smaller extent and a 20 kDa marker to an even smaller extent. A marker molecule of 40 kDa shows minimal penetration, while a marker molecule of 70 kDa shows no penetration at all (basal penetration). These results indicate that 40-70 kDa is a cutoff size for non-specific permeability enhancement by formulations of the invention. Thus administration of a large volume of formulation (300 μL) to the jejunum of rats resulted in permeability enhancement of the intestinal barrier, and this enhanced permeability is restricted by molecular size, showing a cutoff size of 40-70 kDa and minimal penetration at 40 kDa.

Published values of the size of hazardous molecules (molecular weight and radius) which could potentially be present in the intestine are shown below in Table 42.

TABLE 42

|  | MW (kDa) | Radius (Å) |
|---|---|---|
| Macromolecules | >4 | 14 or larger |
| LPS | >100 | Short - 100 |
|  |  | Long - 1000 |
| Enterobacterial Toxins | 70-900 | — |
| Viruses | — | 600-1000 |
| Bacteria | — | 10,000 or larger |

Table 42 demonstrates that potentially hazardous molecules present in the intestine are above the cutoff size of permeability enhancement by the tested formulations, as shown above. Thus these results suggest that the tested formulations will not facilitate penetration of hazardous molecules through the intestinal barrier and these formulations can therefore be considered as safe. Other formulations of the invention give similar results.

B. Formulation Repeated Dosing:

In order to investigate if repeated dosing of formulation affects intestinal permeability, the octreotide improved formulation (12% sodium octanoate with castor oil) was dosed to rats for 14 sequential days using the above in vivo model (rat implanted with two cannulas in the jejunum). At days 1, 7 and 14 of administration, a dextran permeability marker (FITC-dextran of 4.4 kDa MW; FD4), was administered 60 minutes post formulation administration. This was to assess the permeability of the intestine by the penetration of the FD4 from the intestine to blood. No significant difference in FD4 exposure following 14 days of formulation repeated dosing was found. These results suggest there is no increase in intestinal permeability following this period of repeated dosing of formulation, and intestinal enhanced permeability remains a reversible process during this period.

The results suggest that the formulation causes no damage to the intestinal tissue, but acts by specifically opening the intestinal barrier, showing no additive permeability enhancing effect.

Example 34

Intestinal Hyperpermeability Evaluation

Time-Course and Reversibility

Further to the study in the above Example, a study was designed in order to define the time-course of increased intestinal permeability due to the formulations of the invention, and the reversibility of this process, using dextran as a permeability marker.

Figure 8:
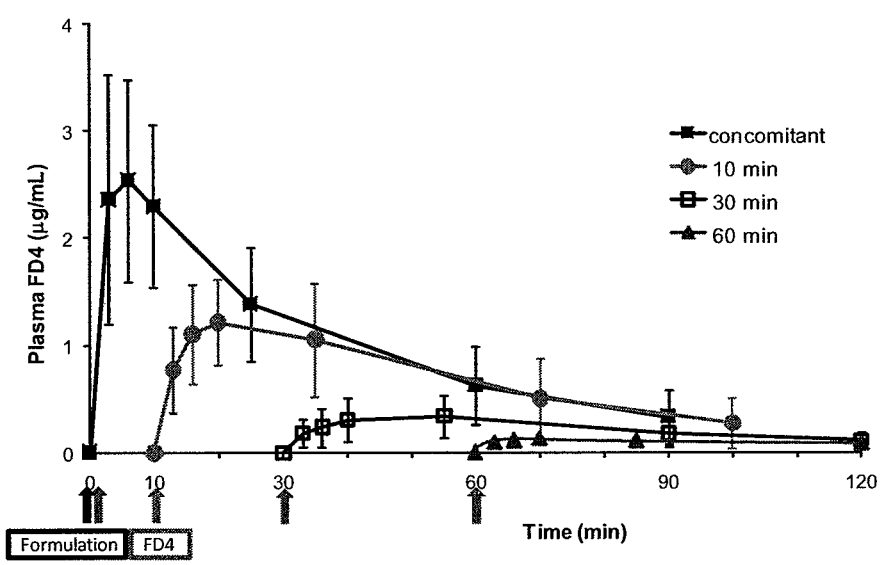
FIG. 8 presents time-course permeability data referenced in accompanying Example 34.

In order to define the time window of increased intestinal permeability, an in vivo model was developed in rats, in which one or two cannulas are implanted in the jejunum of the rats. FITC-labeled dextran (average molecular weight 4.4 kDa, FD4), which has virtually no basal intestinal penetration, served as a molecular marker to test intestinal permeability. An experiment was designed in which the dextran marker was administered concomitant to the formulation (by a jejunal implanted cannula), or at different time intervals from the formulation administration (by a second separate jejunal implanted cannula). Intestinal permeability was evaluated by testing FD4 penetration to blood. Rats were administered a basic formulation concomitant with the dextran marker, or the basic formulation and then the dextran marker at different intervals of time (10, 30 and 60 minutes). Blood samples were analyzed for dextran concentration pre-administration and at 3, 6, 10, 25, 60 and 90 min following dextran administration. The results are shown in FIG. 8. Data is presented as Mean±SD, n≥5.

FIG. 8 demonstrates that the dextran marker penetrates the intestine to the highest extent when administered together with the formulation. An interval of 10 minutes between administration of the formulation and administration of the dextran marker results in significantly decreased amount of marker penetration, and increasing the interval further results in exponential reduction of marker penetration.

These results show that while there is some degree of non-specific permeability enhancing by the formulation, it is restricted to a short period of time following administration of the formulation. The permeability of the intestine decreases sharply with time, and 60 minutes from administration of the formulation there is no more marker penetration. Thus administration of the formulation to the rat intestine results in a very short period of hyperpermeability of the intestinal barrier. Other formulations of the invention gave similar results.

Example 35

Oral Administration of Octreotide to Monkeys

In order to test the pharmacokinetics of octreotide following oral administration of formulated octreotide to monkeys, five Cynomologus monkeys were orally dosed with capsules containing an improved castor oil formulation of octreotide (similar to formulation I of Table 35—but with higher load of octreotide). The capsules used were size 1 gelatin capsules coated with 6.7% Acryl-EZE® enteric coating; this coating prevents capsule disintegration in the stomach and allows opening of the capsules in the small intestine of the dosed animals. The octreotide dose used was 5 mg/capsule.

Monkeys were fasted overnight prior to capsule administration. Following oral administration, blood samples were withdrawn over a period of 9.75 hours, processed for plasma and analyzed for octreotide content by the LC/MS/MS method: see FIG. 9. Similar experiments were performed with the improved no castor oil/GTC formulation (similar to formulation IV of Table 35 but with higher load of API) and similar results were obtained Similar experiments were also performed with several different enteric coatings and similar results were obtained.

In order to compare the pharmacokinetics of octreotide following administration of the improved octreotide formulation, to the pharmacokinetics of injected octreotide, octreotide acetate solution (0.1 mg/monkey) was administered subcutaneously to two monkeys from the above group to serve as a reference. Blood samples were withdrawn over a period of four hours, processed for plasma and analyzed for octreotide content by the LC/MS/MS method.

Figure 9:
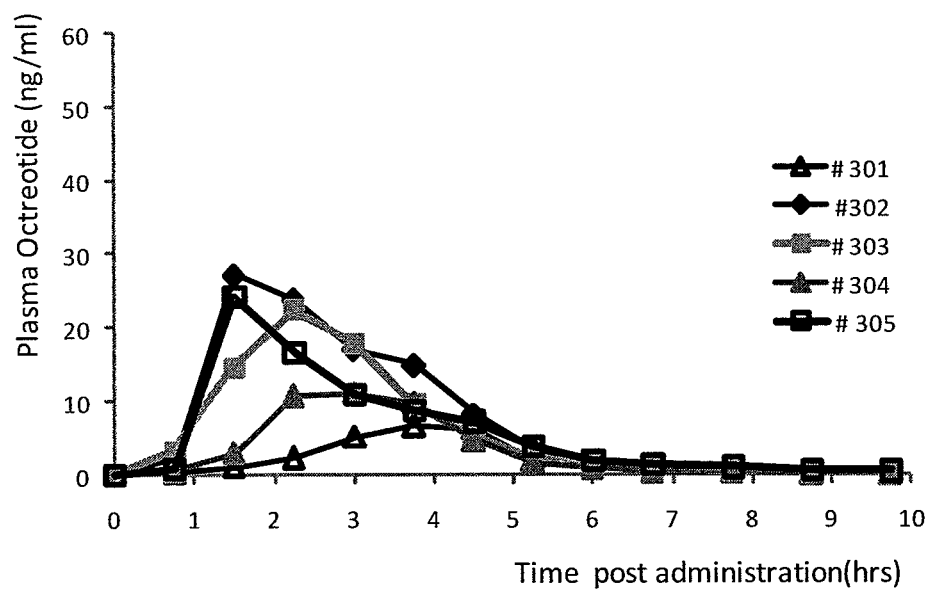
FIGS. 9 and 10 present data relating to administration of octreotide to monkeys referenced in accompanying Example 35.
Figure 10:
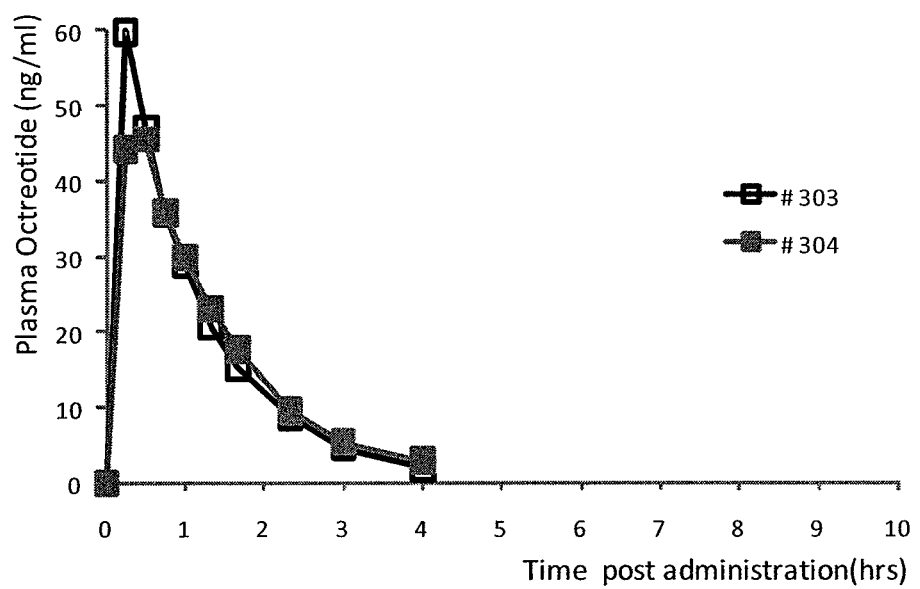

The pharmacokinetics of octreotide following oral octreotide and subcutaneous injected octreotide solution were compared (see FIGS. 9 and 10). The results of the oral formulation showed absorption over a period of a few hours. The shape of the graph was changed compared to subcutaneous, showing slower but longer release of octreotide into the blood. This may be advantageous since this allows the persistence of octreotide for a longer time in the blood potentially prolonging the activity window.

An approved dose for injected octreotide acetate in humans is 0.1 mg/patient. The above results in the monkeys suggest that the improved formulation containing about 10 mg octreotide per dose will generate therapeutic exposure in humans.

Example 36

Stability Data

Basic and improved octreotide formulations of the invention were maintained both at 4° C. and at 25° C. and were tested for octreotide content periodically. Both formulations were found to be stable.

Example 37

Formulations Incorporating Vancomycin, Interferon-Alfa and Terlipressin

A. Vancomycin:

Table 43 below describes a vancomycin improved formulation, containing 10% PVP and 15% sodium octanoate in the hydrophilic fraction, and containing glyceryl tricaprylate as the main constituent of the hydrophobic medium. The vancomycin was obtained from Gold Biotechnology.

TABLE 43

| | Ingredient | Formulation, API Vancomycin (% w/w) |
|---|---|---|
| Hydrophilic fraction | API | 6.267 |
| | NaOH | 0.082 |
| | PVP- 12 | 10.005 |
| | Sodium octanoate | 15.016 |
| | Water | 1.216 |
| Hydrophobic medium | Tween 80 | 2.004 |
| | Glyceryl monocaprylate | 4.008 |
| | Glyceryl tricaprylate | 61.400 |
| | Castor oil | 0.000 |

In a preliminary experiment, the formulation described above in Table 43 was administered directly to the jejunum of non-anesthetized rats, and plasma vancomycin levels were measured post-formulation administration. Exposure value, AUC, was determined for the formulation. The results are that the absolute BA is around 5% (comparative to IV, n=6). When vancomycin in saline solution was administered to the jejunum of non-anesthetized rats no BA was detected.

Interferon-Alfa:

Table 44 below describes an interferon-alfa improved formulation, containing 10% PVP and 15% sodium octanoate in the hydrophilic fraction, and containing glyceryl tricaprylate as the main constituent of the hydrophobic medium. The interferon-alfa is supplied in a buffer (from Intas Biopharmaceuticals) and the ingredients of the interferon-alfa buffer in the formulation are marked by an asterisk (*).

TABLE 44

| | Ingredient | Formulation, API IFN-α (% w/w) |
|---|---|---|
| Hydrophilic fraction | API | 0.050 |
| | *Na₂HPO₄ | 0.032 |
| | *NaH₂PO₄ | 0.030 |
| | *Polysorbate (Tween) 80 | 0.002 |
| | *Disodium EDTA | 0.002 |
| | PVP- 12 | 10.026 |
| | Sodium Octanoate | 14.997 |
| | Water | 1.006 |
| Hydrophobic medium | Tween 80 | 2.005 |
| | Glyceryl monocaprylate | 4.005 |
| | Glyceryl tricaprylate | 67.84 |
| | Castor oil | 0 |

The formulation described above in Table 44 is administered directly to the jejunum of non-anesthetized rats. Plasma interferon-alfa levels are measured post-formulation administration.

C. Terlipressin:

Table 45 below describes a terlipressin basic formulation and a terlipressin improved formulation containing 10% PVP and 15% sodium octanoate in the hydrophilic fraction, and containing glyceryl tricaprylate as the main constituent of the hydrophobic medium. The terlipressin was obtained from Bambio. The basic formulation was prepared essentially as described above and the improved formulation is also prepared essentially as described above.

TABLE 45

| | | Formulation, API | |
|---|---|---|---|
| | Ingredient | Terlipressin basic (% w/w) | Terlipressin improved (% w/w) |
| Hydrophilic fraction | API | 0.235 | 0.235 |
| | MgCl₂ | 0.137 | 0.000 |
| | PVP 12 | 2.736 | 10.004 |
| | Sodium octanoate | 12.004 | 15.015 |
| | MC 400 | 0.137 | 0.000 |
| | Water | 0.610 | 1.010 |
| Hydrophobic medium | Span40 | 1.211 | 0.000 |
| | Lecithin | 2.428 | 0.000 |
| | Ethyl isovalerate | 10.500 | 0.000 |
| | Glyceryl monooleate | 2.278 | 0.000 |
| | Glyceryl tributyrate | 23.708 | 0.000 |
| | Castor oil | 44.016 | 0.000 |
| | Tween 80 | 0.000 | 2.002 |
| | GMC | 0.000 | 4.004 |
| | GTC | 0.000 | 67.731 |

The formulations described above in Table 45 are administered directly to the jejunum of non-anesthetized rats. Plasma terlipressin levels are measured post-formulation administration.

Example 38

Inhibition of Growth Hormone In Vivo by Octreotide

One of the best characterized effects of octreotide is the inhibition of growth hormone release. In order to test for the efficacy of an octreotide formulation of the invention on growth hormone inhibition, a rat model was used in which endogenous rat growth hormone (rGH) levels were monitored following octreotide formulation administration to the jejunum of the non-anesthetized rat model (described above). Administration of a basic octreotide formulation (containing 12% sodium octanoate) to the jejunum of rats was shown to reduce rGH levels by 87.4% compared to administration of a saline control. This result demonstrates that the octreotide formulations described herein enable delivery of octreotide in its active form from the intestinal lumen into the blood stream.

Example 39

Toxicology Studies

A 28-day toxicity administration study of formulation control (excipients only, no cargo) was performed in Wistar rats. The animals in the test group were daily administered rectally with the maximal feasible dose of formulation (100 μL/animal/day) for 28 consecutive days. The test group was compared to two control groups: a naïve group (non-treated) and a saline administered group, (n=15/group).

General clinical observations were made twice daily, and detailed clinical observations were performed weekly. Body weight and food consumption were measured weekly. Clinical pathology and gross pathology were conducted one day after the last treatment. A histological examination was performed on rectum, colon, liver and kidneys, and no toxic effects were detected. There was clean histopathology with no local GI or systemic findings, no formulation related clinical findings, no changes in hematological and blood chemistry parameters, no macroscopic findings at necropsy and no mortality. In conclusion, this experiment demonstrated that there was no observed toxicity during a daily rectal dosing of formulation to rats for 28 consecutive days.

Having thus described several aspects of at least one embodiment, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

The invention claimed is:

1. An enteric-coated oral dosage form comprising a composition comprising a suspension which comprises an admixture of a hydrophobic medium and a solid form wherein the solid form comprises a therapeutically effective amount of a polypeptide, at least one salt of a medium chain fatty acid and polyvinylpyrrolidone (PVP), wherein the polyvinylpyrrolidone is present in the composition at an amount of 3% or more by weight, and wherein the at least one salt of a medium chain fatty acid salt is present in the composition at an amount of at least 12% or more by weight.

2. The enteric-coated oral dosage form of claim 1, wherein the medium chain fatty acid salt is present in the composition at an amount of 12% to 40% by weight.

3. The enteric-coated oral dosage form of claim 2 wherein the medium chain fatty acid salt is present in the composition at an amount of 12% to 18% by weight.

4. The enteric-coated oral dosage form of claim 1 where the polyvinylpyrrolidone is present in the composition at an amount of about 3% to about 20% by weight.

5. The enteric-coated oral dosage form of claim 4 where the polyvinylpyrrolidone is present in the composition at an amount of about 5% to about 15% by weight.

6. The enteric-coated oral dosage form of claim 1, wherein the hydrophobic medium comprises glyceryl tricaprylate and the solid form consists of a polypeptide polyvinylpyrrolidone with a molecular weight of about 3000, and sodium octanoate.

7. The enteric-coated oral dosage form of claim 1 wherein the hydrophobic medium additionally comprises castor oil or glyceryl monocaprylate or a combination thereof and a surfactant.

8. The enteric-coated oral dosage form of claim 1 wherein the hydrophobic medium consists of glyceryl tricaprylate, glyceryl monocaprylate, and polyoxyethylene sorbitan.

9. The enteric-coated oral dosage form of claim 1 wherein the solid form consists essentially of polypeptide, polyvinylpyrrolidone with a molecular weight of about 3000, and sodium octanoate.

10. The enteric-coated oral dosage form of claim 1 wherein the composition comprises about 41% of glyceryl tricaprylate, about 27% castor oil, about 4% glyceryl monocaprylate, about 2% polyoxyethylene sorbitan monooleate, about 15% sodium octanoate, about 10% polyvinylpyrrolidone with a molecular weight of about 3000 and a therapeutically effective amount of polypeptide.

11. The enteric-coated oral dosage form of claim 1 wherein the composition comprises about 68% glyceryl tricaprylate, about 4% glyceryl monocaprylate, about 2% polyoxyethylene sorbitan monooleate, about 15% sodium octanoate, about 10% polyvinylpyrrolidone with a molecular weight of about 3000 and a therapeutically effective amount of polypeptide.

12. The enteric-coated oral dosage form of claim 1, wherein the composition comprises a therapeutically effective amount of polypeptide, about 12-21% of sodium octanoate, about 5-10% of polyvinylpyrrolidone with a molecular weight of about 3000, about 20-80% of glyceryl tricaprylate, about 0-50% castor oil and about 3-10% surfactant.

13. The enteric-coated oral dosage form of claim 1, wherein the composition comprises a therapeutically effective amount of polypeptide, about 12-21% of sodium octanoate, about 5-10% of polyvinylpyrrolidone with a molecular weight of about 3000, about 20-80% of glyceryl tricaprylate and about 3-10% surfactant.

14. The enteric-coated oral dosage form of claim 13, wherein the polypeptide is present at an amount of less than 33%.

15. The enteric-coated oral dosage form of claim 14, wherein the composition comprises about 15% of sodium octanoate, about 10% of polyvinylpyrrolidone with a molecular weight of about 3000, about 30-70% glyceryl tricaprylate and about 6% of surfactant.

16. The enteric-coated oral dosage form of claim 15, wherein the surfactant is glyceryl monocaprylate or polyoxyethylene sorbitan monooleate.

17. The enteric-coated oral dosage form of claim 1, wherein the solid form comprises a particle or a plurality of particles.

18. The enteric-coated oral dosage form of claim 16, wherein the solid form further comprises a stabilizer.

19. The enteric-coated oral dosage form of claim 1, wherein the solid form further comprises a stabilizer.

20. The enteric-coated oral dosage form of claim 13, wherein the polypeptide is present at an amount of less than 25%.

21. The enteric-coated oral dosage form of claim 13, wherein the polypeptide is present at an amount of less than 10%.

22. The enteric-coated oral dosage form of claim 13, wherein the polypeptide is present at an amount of less than 1%.

23. The enteric-coated oral dosage form of claim 13, wherein the polypeptide is present at an amount of less than 0.1%.

24. The enteric-coated oral dosage form of claim 1, wherein the polyvinylpyrrolidone has a molecular weight of about 3000.

25. The enteric-coated oral dosage form of claim 1, wherein the medium chain fatty acid salt has a chain length from about 6 to about 14 carbon atoms.

26. The enteric-coated oral dosage form of claim 25, wherein the medium chain fatty acid salt is sodium hexanoate, sodium heptanoate, sodium octanoate, sodium nonanoate, sodium decanoate, sodium undecanoate, sodium dodecanoate, sodium tridecanoate or sodium tetradecanoate, or a corresponding potassium or lithium or ammonium salt or a combination thereof.

27. The enteric-coated oral dosage form of claim 26, wherein the medium chain fatty acid salt is sodium octanoate.

28. The enteric-coated oral dosage form of claim 1, wherein the hydrophobic medium comprises a mineral oil, a paraffin, a fatty acid a monoglyceride, a diglyceride, a triglyceride, an ether or an ester, or a combination thereof.

29. The enteric-coated oral dosage form of claim 1, wherein the hydrophobic medium comprises glyceryl tricaprylate.

30. The enteric-coated oral dosage form of claim 1, wherein the composition further comprises a surfactant.

* * * * *